(12) United States Patent
Bar-Or et al.

(10) Patent No.: US 7,449,338 B2
(45) Date of Patent: Nov. 11, 2008

(54) TESTS FOR THE RAPID EVALUATION OF ISCHEMIC STATES AND KITS

(75) Inventors: David Bar-Or, Englewood, CO (US); Edward Lau, Boulder, CO (US); James V. Winkler, Denver, CO (US); Gary Fagan, Broomfield, CO (US); Hollie Wayment, Elizabeth, CO (US)

(73) Assignee: Ischemia Technologies, Inc., Waltham, MA (US)

( * ) Notice: Subject to any disclaimer, the term of this patent is extended or adjusted under 35 U.S.C. 154(b) by 0 days.

(21) Appl. No.: 10/319,263

(22) Filed: Dec. 13, 2002

(65) Prior Publication Data

US 2003/0180820 A1 Sep. 25, 2003

Related U.S. Application Data

(60) Continuation-in-part of application No. 09/806,247, filed as application No. PCT/US99/22905 on Oct. 1, 1999, now abandoned, and a continuation-in-part of application No. 09/165,581, filed on Oct. 2, 1998, now Pat. No. 6,492,179, and a continuation-in-part of application No. 09/165,926, filed on Oct. 2, 1998, now Pat. No. 6,461,875, application No. 10/319,263, which is a continuation-in-part of application No. 10/232,341, filed on Aug. 30, 2002, which is a division of application No. 09/165,961, filed on Oct. 2, 1998, now Pat. No. 6,475,743, application No. 10/319,263, which is a continuation-in-part of application No. 09/820,416, filed on Mar. 29, 2001, now Pat. No. 7,070,937, which is a continuation-in-part of application No. 09/165, 961, filed on Oct. 2, 1998, now Pat. No. 6,475,743.

(60) Provisional application No. 60/115,392, filed on Jan. 11, 1999, now abandoned, provisional application No. 60/102,738, filed on Oct. 2, 1998, now abandoned.

(51) Int. Cl.
G01N 33/48 (2006.01)

(52) U.S. Cl. .......................................... 436/63; 436/182

(58) Field of Classification Search .................. 436/74, 436/536, 63, 1, 8; 422/61; 435/4
See application file for complete search history.

(56) References Cited

U.S. PATENT DOCUMENTS

| | | | |
|---|---|---|---|
| 3,955,926 A | 5/1976 | Fischer | |
| 4,230,601 A * | 10/1980 | Hill .............................. | 436/14 |
| 4,337,064 A | 6/1982 | Gindler | |
| 4,379,848 A | 4/1983 | Yeaw | |
| 4,434,234 A | 2/1984 | Adams et al. | |
| 4,468,466 A | 8/1984 | Morrissey | |
| 4,486,282 A | 12/1984 | Bier | |
| 4,492,753 A | 1/1985 | Shell et al. | |
| 4,510,383 A | 4/1985 | Ruppender | |
| 4,568,647 A | 2/1986 | Sanford | |
| 4,569,794 A | 2/1986 | Smith et al. | |
| 4,592,893 A | 6/1986 | Poppe et al. | |
| 4,713,327 A | 12/1987 | Findlay et al. | |
| 4,786,605 A | 11/1988 | Mauck et al. | |
| 4,960,710 A | 10/1990 | Lau | |
| 5,077,222 A | 12/1991 | Lau | |
| 5,141,855 A | 8/1992 | Schmittou | |
| 5,169,936 A | 12/1992 | Staples et al. | |
| 5,173,422 A | 12/1992 | Knowles et al. | |
| 5,173,431 A | 12/1992 | Pugia et al. | |
| 5,182,214 A | 1/1993 | Kessler et al. | |
| 5,183,809 A | 2/1993 | Weisz et al. | |
| 5,223,392 A | 6/1993 | Cohen et al. | |
| 5,225,354 A | 7/1993 | Knowles et al. | |

(Continued)

FOREIGN PATENT DOCUMENTS

| | | | |
|---|---|---|---|
| WO | WO0020840 | * | 10/1999 |
| WO | WO 00/20454 | | 4/2000 |
| WO | WO 00/20840 | | 4/2000 |
| WO | WO 00/52476 | | 9/2000 |
| WO | WO 2004/030522 | | 4/2004 |

OTHER PUBLICATIONS

Dorland's Illustrated Medical Dictionary, p. 911 and p. 1275, 2000.*
PCT/US99/22746, International Search Report, Filing Date Aug. 1, 1999.
Afanas'Ev, Superoxide Ion: Chemistry and Biological Implications, vol. I, pp. 26-27, 51, 147-148, 168-195, 248-266, CRC Press (1989).
Afanas'Ev, Superoxide Ion: Chemistry and Biological Implications, vol. II, Oxygen Radicals in Biology, CRC Pres, pp. 138,187.
Ames et al., (1993) Oxidants, Antioxidants, and the Degenerative Disease of Aging, Proc. Natl. Acad. Sci. USA 90:7915-7922.
Anderson et al., (1995) Effects of na+k+2cl Contransport Inhibition on Myocardial NA and CA During Ischemia and Reperfusion, http://www.tmc.edu/apstracts/1995/cells/september319c.html, p. 1.
Bar-Or et al., (2001) Characterization of the $Co^{2+}$ and $Ni^{2+}$ Binding Amino-Acid Residues of the N-terminus of Human Albumin, Eur. J. Biochemistry, 268:42-47.

(Continued)

Primary Examiner—Patricia A Duffy
(74) Attorney, Agent, or Firm—Swanson & Bratschun L.L.C.

(57) ABSTRACT

The present invention relates to rapid methods for the detection of ischemic states and to kits for use in such methods. Provided for is a rapid method of testing for and quantifying ischemia based upon methods of detecting and quantifying the existence of an alteration of the serum protein albumin which occurs following an ischemic event; methods for detecting and quantifying this alteration include evaluating and quantifying the cobalt binding capacity of circulating albumin, analysis and measurement of the ability of serum albumin to bind exogenous cobalt, detection and measurement of the presence of endogenous copper in a purified albumin sample and use of an immunological assay specific to the altered form of serum albumin which occurs following an ischemic event. Also taught by the present invention is the detection and measurement of an ischemic event by measuring albumin N-terminal derivatives that arise following an ischemic event, including truncated albumin species lacking one to four N-terminal amino acids or albumin with an acetylated N-terminal Asp residue.

28 Claims, 19 Drawing Sheets

U.S. PATENT DOCUMENTS

| | | | | |
|---|---|---|---|---|
| 5,227,307 | A | * | 7/1993 | Bar-Or et al. ............... 436/63 |
| 5,246,835 | A | | 9/1993 | Suzuki et al. |
| 5,290,519 | A | * | 3/1994 | Bar-Or et al. ............... 422/61 |
| 5,290,678 | A | | 3/1994 | Jackowski |
| 5,326,707 | A | | 7/1994 | Franke et al. |
| 5,503,987 | A | | 4/1996 | Wagner et al. |
| 5,532,136 | A | | 7/1996 | Carlson et al. |
| 5,569,608 | A | | 10/1996 | Sommer |
| 5,604,105 | A | | 2/1997 | Jackowski |
| 5,620,856 | A | | 4/1997 | Carlson et al. |
| 5,639,624 | A | | 6/1997 | Wagner et al. |
| 5,654,160 | A | | 8/1997 | Johnson |
| 5,656,729 | A | | 8/1997 | Fuluhata et al. |
| 5,670,627 | A | | 9/1997 | Johnson |
| 5,670,645 | A | | 9/1997 | Johnson |
| 5,683,907 | A | | 11/1997 | Johnson |
| 5,710,008 | A | | 1/1998 | Jackowski |
| 5,744,358 | A | | 4/1998 | Jackowski |
| 5,747,274 | A | | 5/1998 | Jackowski |
| 5,804,452 | A | | 9/1998 | Pronovost et al. |
| 5,876,969 | A | | 3/1999 | Fleer et al. |
| 5,994,339 | A | | 11/1999 | Crapo et al. |
| 6,020,204 | A | | 2/2000 | DerVartanian et al. |
| 6,083,758 | A | | 7/2000 | Imperiali et al. |
| 6,087,184 | A | | 7/2000 | Magginetti |
| 6,171,870 | B1 | | 1/2001 | Freitag |
| 6,235,489 | B1 | | 5/2001 | Jackowski |
| 6,268,223 | B1 | | 7/2001 | Cornell-Bell et al. |
| 6,274,305 | B1 | | 8/2001 | Sonnenschein et al. |
| 6,335,205 | B1 | | 1/2002 | Bausback |
| 6,375,930 | B2 | | 4/2002 | Young et al. |
| 6,410,341 | B1 | | 6/2002 | Freitag et al. |
| 6,444,432 | B1 | | 9/2002 | Kleinfeld |
| 6,461,875 | B1 | * | 10/2002 | Bar-Or et al. ............... 436/536 |
| 6,475,743 | B1 | | 11/2002 | Bar-Or et al. |
| 6,492,179 | B1 | * | 12/2002 | Bar-Or et al. ............... 436/74 |
| 6,767,708 | B1 | * | 7/2004 | Williams et al. ............ 435/7.1 |
| 2003/0190691 | A1 | | 10/2003 | Bar-Or et al. |
| 2003/0194813 | A1 | | 10/2003 | Bar-Or et al. |
| 2003/0215359 | A1 | | 11/2003 | Bar-Or et al. |
| 2003/0215952 | A1 | | 11/2003 | Bar-Or et al. |
| 2004/0175754 | A1 | | 9/2004 | Bar-Or et al. |
| 2004/0209379 | A1 | | 10/2004 | Bar-Or et al. |

OTHER PUBLICATIONS

Bar-Or et al., (2001) Reduced Albumin-Cobalt Binding with Transient Myocardial Ischemia After Elective Percutaneous Transluminal Coronary Angioplasty: A Preliminary Comparison to Creatine Kinase-MB, Myoglobin, and Troponin I, *American Heart Journal*, 141(6): 986-991.

Bautista and Mateos-Nevado (1998) Immunological Detection and Quantification of Oxidized Proteins by Labelling with Digoxigenin, Biosci. Biotechnol. Biochem. 62:419-423.

Biochemistry, Third Edition, Lubert Stryer, ed., W.H. Freemand and Company, New York, pp. 62-64, 895-897 (1988).

Boehringer Mannheim Catalog No. 15947 for 30-80 tests, p. 375.

Braughler (1987) Calcium and Lipid Peroxidatio, Central Nervous System Diseases Research Unit, p. 99, Upjohn Co., Kalamazoo, MI.

Brennan & Peach (1988) Characterisation of a Slow Component of Normal Human Serum Albumin, Clinica Chemica Acta, 176:179-184.

Chan et al. (1995) Site-Specific N-Terminal Auto-Degradation of Human Serum Albumin, Eur. J. of Biochem. 227:524-528.

Cobbe et al. (1980) The Time of Onset and Severity of Acidosis in Myocardial Ischaemia, J. of Mol/Cell Cardiology 12:745-760.

Cotelle et al. (1992) Redox Chemistry of Complexes of Ni II . . . J. of Inorg. Biochem. 46:7-15.

Das & Maulik (1994) Antioxidant Effectiveness in Ischemia-Reperfusion Tissue Injury, Methods in Enxymology 233:601-611.

Davies and Goldberg (1987) Oxygen Radicals Stimulate Intracellular Proteolysis and Lipid Peroxidation by Independent Mechanisms in Erythrocytes, J. of Bio. Chem. 262:8220-8225.

Davies (1987) Protein Damage and Degradation by Oxygen Radicals, J. of Biochem. 262:9895-9901, 9902-9907, 9908-9913, 9914-9920.

Davies (1986) Intracellular Proteolytic Systems . . . J. of Free Rad. In Bio. & Med. 2:155-161, 164-169.

DNA Damage Linked to Risk of Breast Cancer Spread, http://www/pslgroup.com/dg/6c2e.html.

Dolovich et al. (1984) Occupational Asthma from Ni Sensitivity, Brit. J. of Ind. Med. 41:51-55.

Fleming et al. (1986) Quantifiable Color Test, Anal. Biochem. 154:691-701.

Florence (1995) Role of Free Radicals in Disease, Aus. NZ J. of Opth. 23: 3-7.

Genest et al. (1990) Plasma Homocyst. Levels in Men with Premature Coronary Artery Disease, JACC 16:1114-1119.

Glutathione, Interconversion of . . . , pp. 733-739.

Gobel et al. (1998) Long-term Follow-up . . . Unstable *Angina pectoris*, Eur. Heart J. 19:1208-1213.

Gomez (1996) Ruling Out Ischemia Saves Time and Money, Clinician Reviews 6:148 or JACC 28:25-33.

Gutteridge & Wilkins (1983) Copper Salt-Dependent Hydroxyl Radical Formation Damage to Proteins Acting as Antioxidants, Biochimica et Biophysica Acta 759:38-41.

Halliwell (1988) Albumin . . . Extracellular Antioxidant?, Biochem. Pharmacol. 37:569-571.

Halliwell & Gutteridge (1986) Oxygen Free Radicals and Iron in Relation to Biology and Medicine: Some Problems and Concepts, Arch. of Biochem. and Biophys. 246:501-514.

Halliwell & Gutteridge (1989) Free Radicals in Bio. & Med., Second Edit., Oxford, pp. 1-21.

Halliwell (1987) Oxygen Radicals and Tissue Injury, Proceedings of Brook Lodge Symposium, pp. 100-104.

Halliwell & Gutteridge (1990) Antioxidants of Human Extracellular Fluids, Arch. of Biochem. and Biophys. 280:1-8.

Harlow et al., Antibodies: A Lab. Manual, 6:139-243.

Harlow et al., Antibodies: A Lab. Manual, 14:553-612.

Hayakawa (1997) Alteration of Redox State of Human Serum Albumin in Patients Under Anesthesia, J. of Chrom. 698:27-33.

Hedges et al. (1996) Prospective Assessment of Presenting Serum Markers for Cardiac Rsk Strat., Acad. Emerg. Med. 3:27-33.

Henderson's Dict. Of Biol. Terms, 10th ed., (1989) Eleanor Lawrence, edit., John Wiley & Sons, NY, p. 252.

Hisashi (1997) Atp-Sensitive k+ Channels in Pancreatic, Cardiac, and Vascular Smooth Muscle Cells, http://oac3.hsc.uth.tmc.edu/apstracts/1997/cell/October/291C.html, p. 1.

Huang (1995) Ischemia and Reperfusion-Sensitive Cardiac Sympathetic Afferents . . . http://www.uth.tmc.edu/apstracts/1995/heart/April/120h.html, p. 1.

Ishikawa et al. (1997) Reversible Myocardial Ischemic Injury Not Associated with Increased Creatine . . . Clin. Chem. 43:467-475.

Ishimoto (1996) Tole of Oxygen-Derived Free Radicals in Fetal Growth Retardation Induced by Ischemia-Repurfusion in Rats, http://oac3.hsc.uth.tmc.edu/apstracts/1996/heart/September/371h.html, p. 1.

Kadota et al. (1991) Decreased Sulfhydryl Groups of Serum Albumin in Coronary Artery Disease, Jap. Circ. J. 55:937-941.

Karck et al. (1992) TPEN, Transition Metal Chelator, Improves Myocardial Protection During Prolonged Ischemia, J. of Heart & Lung Transpl. 11:979-985.

Keller (1993) Immunochemical Det. Of Oxidized Proteins, Chem. Res. Toxicol. 6:430:433.

Kerr et al. (1996) Intro to Oxygen Free Rads., Heart & Lung 25:200-209.

Knight (1995) Diseases Related to Oxygen-Derived Free Rads., Ann. Of Clin. & Lab. Sci. 25:111-121.

Laussac et al. (1984) Char. Of Copper II-Trasp. Site of Human Serum Albumin . . . Biochem. 23:2832-2838.

Malins et al. (1996) Progression of Human Breast Cancers in the Metastatic State Linked to Hydroxyl Rad.-Induced DNA Damage, Proc. Natl. Acad. Sci.93:2557-2565.

Mangano et al. (1990) Associate of Periop. Myocardial Ischemia with Cardiac Morbidity and Mortality in Men Undergoing Noncardiac Surgery, NE J. of Med.323:1781-1788.

Manso (1992) Ischemia, Reperfusion and Oxygen Free Rads., Rev. Port. Cardiol.11:997-999.

Marx (1985) Site-Specific Mod. Of Albumin by Free Rads., Biochem. J. 236:397-400.

Masuoka et al. (1993) Intrinsic Stoichiometric Equil. Const. For Binding of Zinc II & Copper II to High Affinity Site of Serum Albumin, J. Biol. Chem. 268:21533-21537.

McCord (1985) Oxygen-Derived Free Rads. In Post-Ischemic Tissue Injury, NE J. of Med.312:159-163.

Metal Binding Groups of Proteins, 4:61-69.

Molecular Biol. Of the Cell, 2nd ed.(1989) Garland Publ., Inc., NY pp. 174-180.

New Marker for Exercise-Induced Ischemia, American Assoc. for Clin. Chem.(1997) http://www.aacc.org/cln/profiles/97profiles/05/diagpro9702.html.

Nieboer et al. (1984) Occupational Asthma from Nickel Sensitivity . . . Brit. J. of Indust. Med. 41:56-63.

Odea (1991) Role of Reperfusion-Induced Injury in the Pathogenesis of the Crush Synd., NE J. of Med. 324:1417-1422.

Pepine et al. (1994) Effects of Treatment on Outcome in Mildly Symptomatic Patients with Ischemia During Daily Life, Circ. AHA 90:762-768.

Pepine et al. (1994) J. Myocardial Ischemia, 6(3):8-9.

Peters (1996) All About Albumini, Biochemistry, Genetics & Medical Application, Academic Press p. 244.

Predki et al. (1992) Further Char. Of N-Terminal Copper II- and Nickel II- . . . , Biochem. J. 287:211-215.

Pratico et al. (1997) Localization of Distinct F2-Isoprostanes in Human Atherosclerotic Lesions, J. of Clin. Invest. 100:2028-2034.

QLT Phototherapeutics, Inc. (1996) Product Brochure: Photofrin, Lederly Parenterals, Inc.

Quinlan et al. (1992) Vanadium and Copper in Clinical Solutions of Albumin and Thier Potential to Damage Protein Structure, J. Pharmaceutical Sciences 81:611-614.

Reimer et al. (1992)Myocardial Ischemia, Hypoxia and Infarction, Heart and Cardiovascular Sys.75:1875-1951.

Reimer et al. (1977) Wavefront Phenom. Of Ischemic Cell Death, Circ. Dept. of Pathol., Duke Univ.56:786-794.

Roberts et al. (1997) Rapid MB CK Subform Assay and the Early Diag. Of Myocardial Infarction, Clins. In Lab. Med. 17:669-683.

Röth (1997) Oxygen Free Radicals and Their Clinical Implications, Acta Chirurgica Hungarica 35:302-305.

Sheat (1991) Rapid Detection and Init. Char. Of Genetic Variants of Human Serum Albumin, Clin. Chem. Ref. J. 37:1221-1224.

Shirakawa et al. (1988) Existence of Specific Antibodies to Cobalt in Hard Metal Asthma, Clin. & Exper. Allergy 18:451-460.

Shirakawa et al. (1990) Hard Metal Asthma: Cross Immunological and Resp. Reactivity Btwn Cobalt and Nickel, Thorax 45:267-271.

Shirakawa et al. (1992) Specific IgE Antibodies to Nickel in Workers with Known Reactivity to Cobalt, Clin. & Exper. Allergy22:213-218.

Smith et al. (1998) Cytochemical Demonstration of Oxidative Damage in Alzheimer Disease by Immunochemical Enhancement of Carbonyl Reaction . . . J. of Hitochem. & Cytochem.46:731-735.

Sogami (1984) Res. Of Human Mercapt- and Nonmercaptalbumin by High-Performance Liquid Chro., Int. J. of Pept. Prot. Res.24:96-103.

Stohs (1995) The Role of Free Radicals in Toxicity and Disease, J. Basic & Clin. Physiol. & Pharmacol.6:205-228.

Toxicity & Physiochemical Properties of Metals, Coordination and Chelation4:115-122.

Tucker (1994) Involvement of a Lysine Residue in the N-Terminal . . . Binding Site of Serum Albumins http://search19.proxy.aol.com:8000/post-query/MedLine/hrs1994/23450?albumin+n++p. 1 or Eur. J. of Biochem. (1994) 220:193-200.

Ueda et al. (1994) Activation of Hydrogen Peroxide by Copper II Complexes with Some Histidine-Containing Particles . . . , J. of Inorganic Biochem.55:123-130.

Ueda et al. (1995) Reactions of Copper(II)-Oligopeptide Complexes with Hydrogen Peroxide: Effects of Biological Reductants, Free Radical Biology & Medicine 18:929-933.

Veien et al. (1979) Antibodies Against Nickel-Albumin in Rabbits and Man, Contact Dermatitis5:378-382.

Venugopal et al. Metal Toxicity in Mammals vol. 2, Chem. Toxicity of Metals and Metalloids8:280-289.

Vogel et al. Quant. Chem. Analysis, pp. 198-202.

Witko-Sarsat (1996) Advanced Oxidation Protein Products as a Novel Marker of Oxidative Stress in Uremia, Kidney International 49:1304-1313.

Wysocki (1993) Peroxide Plasma Level in Patients with Coronary Heart Disease as a Possible Indicator of Ischemia During Exercise Test, Coronary Artery Disease 4:645-647.

Yoon et al., J. of Surgical Research, 46:163-165 (1989).

Apple et al. (2002) Clin Chem 48:1097.

Lakusta et al (1979) J Inorg Biochem 11:303.

Laussac et al (1984) Biochem 23:2832.

Masuoka et al (1993) J Biol Chem 268:21533.

Mohanakrishnan et al (1982) J Pharm Sci 71(10):1180.

Sadler et al (1994) Eur J Biochem 220:193.

Bar-Or et al. (1999) Ann Emerg Med 34(4 Suppl):S56.

Christenson et al. (2001) Clinical Chemistry 47(3):464-470.

Belch et al. (1989) Free Radic. Biol. Med. 6(4):375-378.

Berenshtein et al. (1997) J Mol Cell Cardiol. 29(11):3025-3034.

Bradshaw et al. (1968) J Biol. Chem. 243:3817-3825.

Bradshaw et al. (1969) J. Biol. Chem. 244:5582-5589.

Gryzunov et al. (2003) Arch Biochem. Biphys. 413(1):53-66.

Wu et al. (2001) Cardiovascular Toxicology 1:147-151.

Morris et al. (2001) Eur Heart J Abs Supp 22:608.

Gökhan et al. (1996) Int J Cardiology 53:237-244.

Lapresle (1988) Anal. Biochem. 174:308.

Herbert et al. eds. (1995) Dict. Of Immunol. p. 58.

U.S. Appl. No. 09/820,416, filed Mar. 29, 2001, Bar-Or et al.

Our Ref.: 4172-15-1-1, Bar-Or et al., Jan. 31, 2005.

U.S. Appl. No. 10/232,341, filed Aug. 30, 2002, Bar-Or et al.

Bar-Or et al. (2002) Free Rad. Biol.. & Med. 32(2):197.

Bar-Or et al. (2001) Am. Heart J. 141(6):985.

Bar-Or et al. (2000) J. Emerg. Med. 19(4):311.

Buranaprapuk et al. (1998) Biochimica et Biophysica Acta 1387:309-316.

Bal et al. (1998) Journal of Inorganic Biochemistry 70:30-39.

Ischemia Technologies, Inc. brochure for Ischemia Test (1999).

Ischemia Technologies, Inc. brochure for IMA (Sep. 2001).

Ischemia Technologies, Inc. Invoice No. 101, Nov. 30, 2001.

Hermo et al. (2005) Diabetes 54(Suppl. 1):A537.

Ersoz et al. (2005) Diabetologia 48(Suppl. 1):A409.

Janeway, C. et al. (4th ed. 1999) Immunobiology Elsevier Science Ltd./Garland Publishing, pp. 34, 39, 41, 42, 54.

Stryer, L. Biochemistry (3rd ed. 1988) W.H. Freeman & Co., pp. 62-63.

Lawrence, E., Henderson's Dictionary of Biological Terms (10th ed. 1989) John Wiley & Sons, pp. 418, 508.

Sinha MK, et al., *The Albumin Cobalt Binding (ACB) Test, Diagnoses Cardiac Ischaemia in Patients with Non ST-Elevation Chest Pain in the Emergency Department*. Presented at the 52nd American Heart Association Scientific Conference on Molecular, Integrative, and Clinical Approaches to Myocardial Ischemia, Aug. 2001.

Sinha MK, et al. *A Novel Assay for the Detection of Ischaemia in Percutaneous Coronary Intervention by Assessment of Albumin Cobalt Binding, the ACB Test*. Presented at the 52nd American Heart Association Scientific Conference on Molecular, Integrative, and Clinical Approaches to Myocardial Ischemia, Aug. 2001.

Heller GV, et al. *The Albumin Cobalt Binding (ACB) Test To Diagnose Ischemia in Patients with Symptoms of Coronary Artery Disease*. Clinical Chemistry, 2001, 47:6, A205.

Painter et al., *Analytical Studies of an Assay to Detect Myocardial Ischemia*, Clin. Chem. 46:6, A75, 2001.

Wu, AHB. *The Albumin Cobalt Binding Test as a Marker of Cardiac Ischemia*. Third Annual Joint Summit on Markers in Cardiology. Oct. 2000.

Wu AHB, et al. *Preliminary Evaluation of the Albumin Cobalt Binding Test (ACB Test) as a Marker of Myocardial Ischemia in Patients Suspected of Acute Coronary Syndrome*. Fourth National Congress of Chest Pain Centers. Oct. 2000.

Bost et al. (1988) "Antibodies Against a Peptide Sequence Within the HIV Envelope Protein Crossreacts with Human Interleukin-2", Immunol. Invest. 17:577-586.

Bendayan (1995) "Possibilities of False Immunocytochemical Results Generated by the Use of Monoclonal Antibodies: The Example of the Anti-proinsulin Antibody", J. Histochem. Cytochem. 43:881-886.

Coligan et al. (1995) "Production of Monoclonal Antibodies" 1(2.5.1-2.5.17) John Wiley & Sons.

* cited by examiner

SEQUENCE LISTING

<160> NUMBER OF SEQ ID NOS: 2

<210> SEQ ID NO 1
<211> LENGTH: 585
<212> TYPE: PRT
<213> ORGANISM: Homo sapiens

<400> SEQUENCE: 1

```
Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

```
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 2
<211> LENGTH: 585

<212> TYPE: PRT
<213> ORGANISM: Homo sapiens

<220> FEATURE:
<221> NAME/KEY: MOD_RES
<222> LOCATION: (1)..(585)
<223> OTHER INFORMATION: ACETYLATION

<400> SEQUENCE: 2
```

-continued

```
Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
 65                 70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
```

-continued

```
                420                 425                 430
Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
        580                 585
```

TESTS FOR THE RAPID EVALUATION OF ISCHEMIC STATES AND KITS

RELATEDNESS OF THE APPLICATION

The subject application is a continuation-in-part of copending U.S. Ser. No. 09/806,247, filed Mar. 27, 2001, which is a 35 USC § 371 national phase application of PCT/US99/22905, filed Oct. 1, 1999, which claims the benefit of priority from U.S. Ser. No. 60/115,392, filed Jan. 11, 1999, now abandoned; U.S. Ser. No. 60/102,738, filed Oct. 2, 1998, now abandoned; and is a continuation-in-part of U.S. Ser. No. 09/165,581, filed Oct. 2, 1998, now U.S. Pat. No. 6,492,179; and a continuation-in-part of U.S. Ser. No. 09/165,926, filed Oct. 2, 1998, now U.S. Pat. No. 6,461,875; and a continuation-in-part of copending U.S. Ser. No. 10/232,341, filed Aug. 30, 2002, which is a divisional of U.S. Ser. No. 09/165,961, filed Oct. 2, 1998, now U.S. Pat. No. 6,475,743; and a continuation-in-part of copending U.S. Ser. No. 09/820,416, filed Mar. 29, 2001, which is a continuation of U.S. Ser. No. 09/165,961, filed Oct. 2, 1998, now U.S. Pat. No. 6,475,743.

FIELD OF THE INVENTION

The present invention relates to rapid methods for the detection of ischemic states and to kits for use in such methods. More particularly, the invention relates to the measurement of a bound specific transition element to human serum albumin or the measurement of albumin N-terminal derivatives to determine the presence or absence of ischemia.

BACKGROUND OF THE INVENTION

Ischemia is the leading cause of illness and disability in the world. Ischemia is a deficiency of oxygen in a part of the body causing metabolic changes, usually temporary, which can be due to a constriction or an obstruction in the blood vessel supplying that part. The two most common forms of ischemia are cardiovascular and cerebrovascular. Cardiovascular ischemia, in which the body's capacity to provide oxygen to the heart is diminished, is the leading cause of illness and death in the United States. Cerebral ischemia is a precursor to cerebrovascular accident (stroke) which is the third leading cause of death in the United States.

The continuum of ischemic disease includes five conditions: (1) elevated blood levels of cholesterol and other blood lipids; (2) subsequent narrowing of the arteries; (3) reduced blood flow to a body organ (as a result of arterial narrowing); (4) cellular damage to an organ caused by a lack of oxygen; (5) death of organ tissue caused by sustained oxygen deprivation. Stages three through five are collectively referred to as "ischemic disease," while stages one and two are considered its precursors.

Together, cardiovascular and cerebrovascular disease accounted for 954,720 deaths in the U.S. in 1994. Furthermore, more than 20% of the population has some form of cardiovascular disease. In 1998, as many as 1.5 million Americans will have a new or recurrent heart attack, and about 33% of them will die. Additionally, as many as 3 to 4 million Americans suffer from what is referred to as "silent ischemia." This is a condition where no clinical symptoms of ischemic heart disease are present.

There is currently a pressing need for the development and utilization of blood tests able to detect injury to the heart muscle and coronary arteries. Successful treatment of cardiac events depends largely on detecting and reacting to the presence of cardiac ischemia in time to minimize damage. Cardiac enzymes, specifically the creatine kinase isoenzyme (CK-MB), and cardiac markers, specifically the Troponin I and T biochemical markers, are utilized for diagnosing heart muscle injury. However, these enzymes and markers are incapable of detecting the existence of an ischemic state in a patient prior to myocardial infarction and resulting cell necrosis (death of cell). Additionally, these enzymes and markers do not show a measurable increase until several hours after an ischemic event. For instance, CK-MB, the earlier evident of the two, does not shows a measurable increase above normal in a person's blood test until about four to six hours after the beginning of a heart attack and does not reach peak blood level until about 18 hours after such an event. Thus, the primary shortcoming of using cardiac markers for diagnosis of ischemic states is that these markers are only detectable after heart tissue has been irreversibly damaged.

There currently are no tests available which allow diagnosis of the existence of ischemia in patients prior to tissue necrosis. A pressing requirement for emergency medicine physicians who treat chest pain and stroke symptoms is for a diagnostic test that would enable them to definitively "rule out" myocardial infarction, stroke, and other emergent forms of ischemia. A need exists for a method for immediate and rapid distinction between ischemic and non-ischemic events, particularly in patients undergoing acute cardiac-type symptoms. The present invention provides such a means.

A broader array of diagnostic tests are available for diagnosis of ischemia in patients with non-acute symptoms. The EKG exercise stress test is commonly used as an initial screen for cardiac ischemia, but is limited by its accuracy rates of only 25-50%. Coronary angiography, an invasive procedure that detects narrowing in the arteries with 90-95% accuracy, is also utilized. Another commonly used diagnostic test is the thallium exercise stress test, which requires injection of radioactive dye and serial tests conducted four hours apart. The present invention, however, has the advantage over the known methods of diagnosis in that it provides equivalent or better accuracy at far lower costs and decreased risk and inconvenience to the patient. The present invention provides specificity and sensitivity levels of 75-95%, which are far more accurate than the EKG exercise stress test and comparable in accuracy to current diagnostic standards. Furthermore, the present invention presents a significant time advantage and is cheaper than competing methods of diagnosis by a factor of at least 15 to 1.

It is known that immediately following an ischemic event, proteins (enzymes) are released into the blood. Well known proteins released after an ischemic heart event include creatine kinase (CK), serum glutamic oxalacetic transaminase (SGOT) and lactic dehydrogenase (LDH). One well known method of evaluating the occurrence of past ischemic heart events is the detection of these proteins in a patient's blood. U.S. Pat. No. 4,492,753 relates to a similar method of assessing the risk of future ischemic heart events. However, injured heart tissue releases proteins to the bloodstream after both ischemic and non-ischemic events. For instance, patients undergoing non-cardiac surgery may experience perioperative ischemia. Electro-cardiograms of these patients show ST-segment shifts with an ischemic cause which are highly correlated with the incidence of postoperative adverse cardiac events. However, ST-segment shifts also occur in the absence of ischemia; therefore, electrocardiogram testing does not distinguish ischemic from non-ischemic events. The present invention provides a means for distinguishing perioperative ischemia from ischemia caused by, among other things, myocardial infarctions and progressive coronary artery disease.

SUMMARY OF THE INVENTION

The present need for rapid, immediate and continuous detection of ischemic states is met by the present invention. Specifically, the present invention provides for rapid methods of testing for the existence of and quantifying ischemia based upon methods of detecting and quantifying the existence of an alteration of the serum protein albumin which occurs following an ischemic event. Preferred methods of the present invention for detecting and quantifying this alteration include evaluating and quantifying the metal binding capacity of albumin, analysis and measurement of the ability of serum albumin to bind exogenous metal, detection and measurement of the presence of endogenous copper in a purified albumin sample, use of an immunological assay specific to albumin-metal complexes, and detection and measurement of albumin N-terminal derivatives that arise following an ischemic event. Also taught by the present invention is the use of the compound Asp-Ala-His-Lys-R, wherein R is any chemical group capable of being detected when bound to a metal ion that binds to the N-terminus of naturally occurring human albumin, for detection and quantitation of an ischemic event.

Advantages and embodiments of the invention include a method for ruling-out the existence of an ischemic state or event in a patient; a method for detecting the existence of asymptomatic ischemia; a method for evaluating patients with angina to rule-out the recent occurrence of an ischemic event; an immediate method for evaluation of patients suffering from chest pain to detect the recent occurrence of a myocardial infarction; a method for evaluation of patients suffering from stroke-like signs and symptoms to detect the occurrence of a stroke and to distinguish between the occurrence of an ischemic stroke and a hemorrhagic stroke; a rapid method for supplementing electrocardiographic results in determining the occurrence of true ischemic events; a method for detecting the occurrence of a true ischemic event in a patient undergoing surgery; a method for evaluating the progression of patients with known ischemic conditions; a method for comparing levels of ischemia in patients at rest and during exercise; a method for assessing the efficacy of an angioplasty procedure; a method for assessing the efficacy of thrombolytic drug therapy; a method for assessing the patency of an in-situ coronary stent; and, a method for detecting in a pregnant woman the occurrence of placental insufficiency.

Additional advantages, applications, embodiments and variants of the invention are included in the Detailed Description of the Invention and Examples sections.

As used herein, the term "ischemic event," and "ischemic state" mean that the patient has experienced a local and/or temporary ischemia due to partial or total obstruction of the blood circulation to an organ. Additionally, the following abbreviations are utilized herein to refer to the following amino acids:

| Amino acid | Three-letter abbreviation | Single-letter notation |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |

-continued

| Amino acid | Three-letter abbreviation | Single-letter notation |
|---|---|---|
| Glutamic acid | Glu | B |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A separate test method for ischemia was described by a common inventor in U.S. Pat. Nos. 5,227,307 and 5,290,519 to Bar-Or et al., herein incorporated by reference in their entirety. Also incorporated herein in their entireties by reference are the following commonly assigned patents and applications: U.S. Pat. Nos. 6,461,875 6,492,179; and U.S. Ser. No. 60/115,392, filed Jan. 11, 1999.

BRIEF DESCRIPTION OF THE FIGURES

FIG. 10A is Peptide 1 at pH 2.55, while 10B is at pH 7.33. FIG. 10C is the spectra at pH 7.30 with 0.3 equiv. $NiCl_2$, and FIG. 10D is pH 7.33 at about ~1 equiv. $NiCl_2$.

FIG. 11A is Peptide 1 at pH 2.56, while 11B is at pH 7.45.

FIG. 11C is the spectra at pH 7.11 with ~0.5 equiv. CoCl$_2$, and FIG. 11D is pH 7.68 at ~1 equiv. CoCl$_2$.

FIG. 12A is Peptide 1 at pH 2.56, while 12B is at pH 7.54. FIG. 12C is the spectra at pH 7.24 with ~0.5 equiv. CUSO$_4$, and FIG. 12D is pH 7.27 at ~1 equiv. CuSO$_4$.

FIG. 13A is Peptide 2 at pH 2.63. FIG. 13B is Peptide 2 at pH 7.36. FIG. 13C is Peptide 2 at pH 7.09 with about 0.5 equiv. NiCl$_2$. FIG. 13D is Peptide 2 at pH 7.20 with about 1 equiv. NiCl$_2$.

FIG. 14A is Peptide 3 at pH 2.83. FIG. 14B is Peptide 3 at pH 7.15. FIG. 14C is Peptide 3 at pH 7.28 with about 0.13 equiv. NiCl$_2$. FIG. 14D is Peptide 3 at pH 7.80 with about 0.25 equiv. NiCl$_2$. FIG. 14E is Peptide 3 at pH 8.30 with about 0.50 equiv. NiCl$_2$.

FIG. 15A is Peptide 4 at pH 2.72. FIG. 15B is Peptide 4 at pH 7.30. FIG. 15C is Peptide 4 at pH 8.30 with about 0.5 equiv. NiCl$_2$. FIG. 15D is Peptide 4 at pH 8.10 with about 1 equiv. NiCl$_2$.

FIG. 16A is Peptide 5 at pH 2.90. FIG. 16B is Peptide 5 at pH 7.19. FIG. 16C is Peptide 5 at pH 1.02 with about 0.3 equiv. NiCl$_2$. FIG. 16D is Peptide 5 at pH 7.02 with about 0.6 equiv. NiCl$_2$.

FIG. 17A is at pH 2.49. FIG. 17B is at pH 7.44. FIG. 17C is Peptide 3 pH 7.42 with about 0.8 equiv. NiCl$_2$. FIG. 17D is at pH 7.80 with about 1 equiv. NiCl$_2$.

FIG. 18A is at pH 7.44. FIG. 18B is at pH 7.23 with about 0.3 equiv. CoCl$_2$. FIG. 18C is at pH 7.33 with about 0.8 equiv. CoCl$_2$.

FIG. 19A is at pH 7.31. FIG. 19B is at pH 7.26 with about 0.5 equiv. CuSO$_4$. FIG. 19C is at pH 7.32 with about 1.0 equiv. CuSO$_4$.

DETAILED DESCRIPTION OF THE INVENTION

Figure 1:
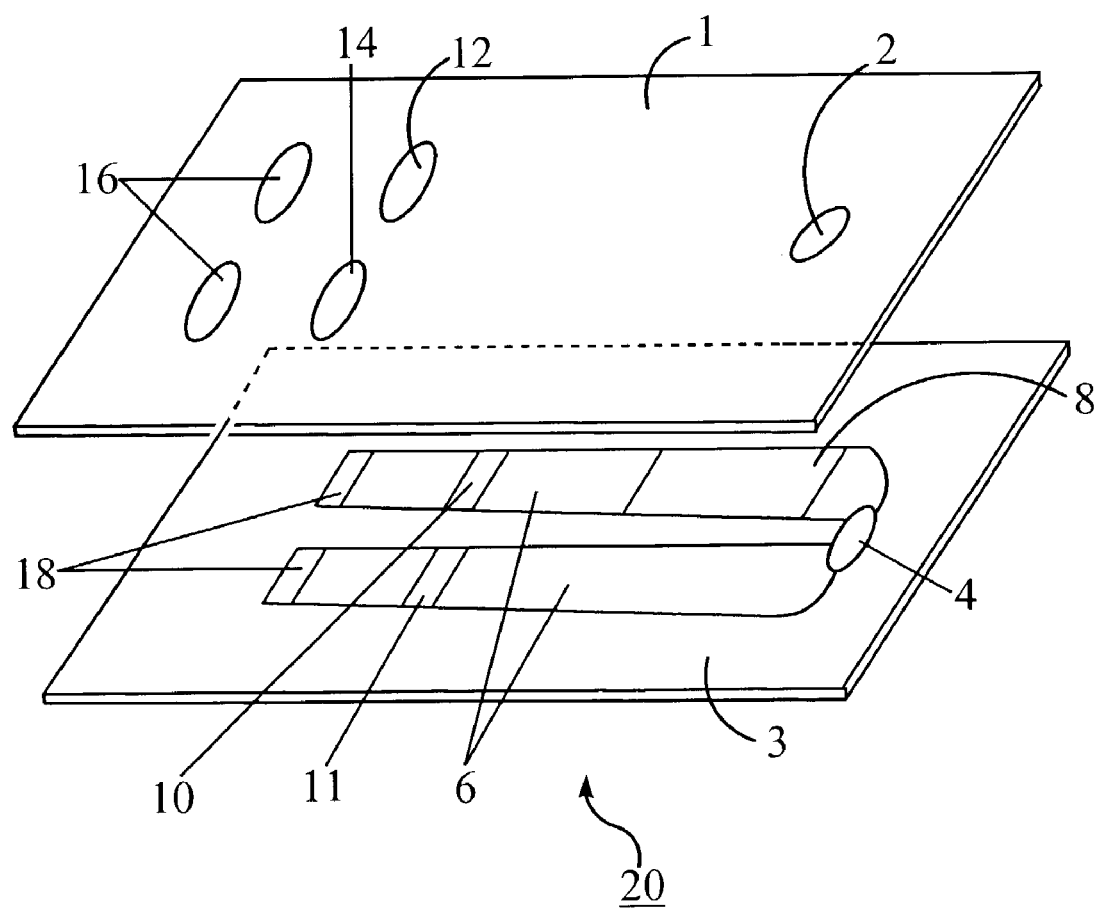
FIGS. 1-3 illustrate kits useful in carrying out the derivative embodiment of the subject invention.

A number of terms used herein have the following definitions.

"Albumin-metal complex" or "metal-albumin complex" means the complex of a divalent cation, including but not limited to copper, cobalt and nickel, to the N-terminus of naturally-occurring albumin.

"Albumin N-terminus" refers to that portion of naturally-occurring albumin constituting comprising at least the four N-terminal amino acids, i.e., Asp-Ala-His-Lys.

"Albumin N-terminal derivatives" refers to those species of albumin that are altered or truncated at the N-terminus as a result of an ischemic event. Specifically, the derivatives include those albumin species lacking 4, 3, 2 and 1 N-terminal amino acid, as well as a full-length albumin that is acetylated at its terminal Asp residue. Albumin-terminal derivatives cannot form albumin-metal complexes and may be found in the blood of ischemic patients. Full-length, naturally-occurring albumin is set forth is SEQ. ID. NO. 1. Acetylated-Asp albumin is set forth in SEQ. ID. NO. 2.

"Antibody to an albumin-metal complex" is an antibody to the epitope formed of the metal and surrounding amino acids and/or their side chains.

"Derivative N-terminus" refers to the 4-12 amino acids at the N-terminus of albumin N-terminal derivatives, which may serve as an epitope in the generation of a monoclonal antibody.

"Endogenous copper" refers to copper present in a patient sample of albumin, i.e., not exogenously added during the diagnostic procedure.

"Excess quantity" of metal ion or "excess metal ion" refers to addition of an amount of metal ion that will substantially exceed the stoichiometrically available albumin metal ion binding sites such that substantially all naturally-occurring albumin is bound to metal ion at its N-terminus.

"Known value" as used herein means a clinically-derived cut-off value or a normal range, to which a measured patient value is compared so as to determine the occurrence or non-occurrence of an ischemic event.

"Naturally-occurring albumin" refers to albumin with an intact N-terminus (Asp-Ala-His-Lys-) that has not been acetylated.

"Purified albumin" or "purified albumin sample" refers to albumin that has been partially purified or purified to homogeneity. "Partially purified" means with increasing preference, at least 70%, 80%, 90% or 95% pure.

"Treadmill test" means a stress test to increase myocardial O$_2$ demand, while observing if a mismatch occurs between demand and supply by observing symptoms such as shortness of breath, chest pain, EKG, low blood pressure and the like.

While not being bound by any particular theory, it is believed that the present method works by taking advantage of alterations which occur to the albumin molecule, affecting the N-terminus of albumin during an ischemic ("oxygen-depletion") event. (Ischemia occurs when human tissue is deprived of oxygen due to insufficient blood flow.) A combination of two separate phenomena are believed to explain the mechanism by which the ischemia test of the present invention works. First, it is believed that the localized acidosis which occurs during an ischemic event generates free radicals which alter albumin's N-terminus; thus, by detecting and quantifying the existence of altered albumin, ischemia can be detected and quantified. Second, the acidotic environment present during ischemia results in the release of bound copper (from ceruloplasmin and other copper-containing proteins) which is immediately taken up by albumin. The bound copper also alters the N-terminus of albumin. (Not only does the presence of the complexed copper effectively "alter" the N-terminus, the metal ion damages the protein structure on binding.) Thus, by detecting and quantifying the existence of altered albumin, and/or the copper-albumin complexes, ischemia can be detected and quantified.

The details of the first mechanism are believed to be as follows. In the event of an oxygen insufficiency, cells convert to anaerobic metabolism, which depletes ATP, resulting in localized acidosis and lowered pH, and causing a breakdown in the energy cycle (ATP cycle). Cellular pumps that keep calcium against the gradient are fueled by energy from the ATP cycle. With ATP depletion, the pumps cease to function and cause an influx of calcium into the cell. The excess intracellular calcium activates calcium-dependent proteases (calpain, calmodulin), which in turn cleave segments of xanthine dehydrogenase, transforming the segments into xanthine oxidase. The enzymes involved in this process are membrane-bound and exposed to the outside of the cell, and are thus in contact with circulating blood. Xanthine oxidase generates superoxide free radicals in the presence of hypoxanthine and oxygen. Superoxide dismutase dismutates the oxygen free radicals, turning them into hydrogen peroxide. In the presence of metals such as copper and iron which are found in blood, hydrogen peroxide causes hydroxyl free radicals to be formed. Hydroxyl free radicals in turn cause damage to cells and human tissue. One of the substances damaged by free radicals is the protein albumin, a circulating protein in human blood; specifically believed to be damaged is the N-terminus of albumin, resulting in the albumin N-terminal derivatives.

Human serum albumin is the most abundant protein in blood (40 g/l) and the major protein produced by the liver. Many other body fluids also contain albumin. The main biological function of albumin is believed to be regulation of the colloidal osmotic pressure of blood. The amino acid and structure of human albumin have been determined. Specifically, human albumin is a single polypeptide chain consisting of 585 amino acids folded into three homologous domains with one free sulfhydryl group on residue # 34. The specific amino acid content of human albumin is:

Residues: Asp Asn Thr Ser Glu Gln Pro Gly Ala Cys
Val Met Ile Leu Tyr Phe His Lys Trp Arg Number 39 15 30 22 60 23 25 12 63 35 39 6 8 61 18
30 16 58 1 23

In the first embodiment of the present invention, an excess of metal (e.g., cobalt) ions are introduced into a (purified) albumin sample obtained from a patient serum, plasma, fluid or tissue sample (this embodiment is hereafter referred to as the "excess metal embodiment"). In normal (non-ischemic) patients, cobalt will bind to one or more amino acid chains on the N-terminus of albumin. In ischemic patients, however, most likely due to the alteration of the binding site of the N-terminus, cobalt binding to albumin is reduced. Accordingly, the occurrence or non-occurrence of an ischemic state can be detected by the presence and quantity of bound or unbound cobalt. Measurement of cobalt can be conducted by atomic absorption, infrared spectroscopy, high-performance liquid chromatography ("HPLC") or other standard or nonstandard methods, including radioactive immunoassay techniques.

The details of the second mechanism are believed to be as follows. Ceruloplasmin is a circulating protein which binds copper; approximately ninety-percent of the in vivo copper (copper is abundant in blood, with concentrations comparable to iron) will be bound to ceruloplasmin. The remainder is in other bound forms; almost no free copper exists in circulating blood. In acidic conditions and reduced oxygen conditions, such as happens during ischemia, ceruloplasmin releases some of its bound copper. The released copper is taken up by albumin. Copper and cobalt both bind to albumin at the same site within the N-terminus. Thus, the bound endogenous copper, present during ischemia, blocks cobalt from binding to albumin. The decrease in cobalt binding capacity of circulating albumin can be measured and quantified as a means for detecting and quantifying the presence of an ischemic event.

The excess metal embodiment of the present invention comprises a method for detecting the occurrence or non-occurrence of an ischemic event in a patient comprising the steps of: (a) contacting a biological sample containing albumin of said patient with an excess quantity of a metal ion salt, said metal ion capable of binding to the N-terminus of naturally occurring human albumin, to form a mixture containing bound metal ions and unbound metal ions, (b) determining the amount of bound metal ions, and (c) correlating the amount of bound metal ions to a known value to determine the occurrence or non-occurrence of an ischemic event. In this method, said excess quantity of metal ion salt may comprise a predetermined quantity and the quantity of unbound metal ions may be detected to determine the amount of bound metal ions. Additionally, the compound selected from the group consisting of Asp-Ala-His-Lys-R, wherein R is any chemical group capable of being detected when bound to a metal capable of binding to the N-terminus of naturally occurring human albumin, may be utilized to facilitate detection.

This method uses samples of serum or plasma, or purified albumin. Preferred embodiments also include use of a metal ion salt comprising a salt of a transition metal ion of Groups 1b-7b or 8 of the Periodic Table of the elements, a metal selected from the group consisting of V, As, Co, Cu Sb, Cr, Mo, Mn, Ba, Zn, Ni, Hg, Cd, Fe, Pb, Au and Ag. Also preferred, is detection of the amount of bound metal ions (or, in the case where the excess quantity of metal ion salt is a predetermined quantity, detection of the quantity of unbound metal ions) by atomic absorption or atomic emission spectroscopy or immunological assay. These detection mechanisms are also preferred for determination of the quantity of the compound Asp-Ala-His-Lys-R which is complexed with the metal ion salt in order to detect the quantity of unbound metal ions. A preferred method for conducting said immunological assay is using an antibody specific to an antigen comprising the compound Asp-Ala-His-Lys-R, wherein R is said metal ion.

Where the metal employed in the above excess metal embodiment is nickel, another preferred detection method is nuclear magnetic resonance (NMR). It has been observed that addition of Ni ion gives a sharp diamagnetic $^1$H-NMR spectrum for the resonances of the first three amino acids (Asp-Ala-His) of the albumin N-terminus octapeptide. While Co ion can also induce changes in the NMR spectrum of the first three amino acids of albumin, it induces paramagnetism at the binding site, resulting in broadening of the resonances associated with the first three residues. Thus, the diamagnetic nature of the nickel complex makes it more amenable for NMR studies.

The excess metal embodiment of the present invention also includes a calorimetric method of detecting the occurrence or non-occurrence of an ischemic event in a patient comprising the steps of: (a) contacting a biological sample containing albumin of said patient with a predetermined excess quantity of a salt of a metal selected from the group consisting of V, As, Co, Cu, Sb, Cr, Mo, Mn, Ba, Zn, Ni, Hg, Cd, Fe, Pb, Au and Ag, to form a mixture containing bound metal ions and unbound metal ions, (b) contacting said mixture with an aqueous color forming compound solution to form a colored solution, wherein said compound is capable of forming color when bound to said unbound metal ion, (c) determining the color intensity of said colored solution to detect the presence of unbound metal ions to provide a measure of bound metal ions, and (d) correlating the amount of bound metal ions to a known value to determine the occurrence or non-occurrence of an ischemic event. Preferred embodiments of this method include the additional step of diluting said colored solution with an aqueous solution isosmotic with blood serum or plasma prior to step (c). Also preferred are: using ferrozine as the color forming compound, and, alternatively, using the compound Asp-Ala-His-Lys-R, wherein R is any group capable of forming color when bound to said metal ion as the aqueous color forming compound. Conducting steps (b) and (c) in a pH range of 7 to 9 is preferred. Further, conducting steps (b) and (c) using a spectrophotometer is preferred. Preferred samples in this method include serum, plasma, or purified albumin and a preferred metal ion salt is cobalt. The colorimetric method is used in the Albumin Cobalt Binding or ACB™ Test which is manufactured by Ischemia Technologies, Inc., Denver, Colo.

Another embodiment is based on the endogenous copper mechanism discussed above. This embodiment involves a method for detecting the occurrence or non-occurrence of an ischemic state in a patient comprising the steps of: (a) detecting the amount of endogenous copper ions present in a purified albumin sample of said patient, and (b) correlating the quantity of copper ions present with a known value to determine the occurrence or non-occurrence of an ischemic event. Preferred methods for detection of the amount of copper ions present in the purified albumin sample are by atomic absorption, atomic emission spectroscopy and immunological assay. A preferred method of conducting said immunological assay uses an antibody specific to an antigen comprising the compound Asp-Ala-His-Lys-R, wherein R is copper. This embodiment is referred to as the endogenous copper method.

Another embodiment of the subject invention is also based on the first mechanism described above. The free radicals released during an ischemic event damage the N-terminus of albumin by causing the cleavage of up to four N-terminal amino acid residues, and possibly may induce acetylation of the N-terminus. The resulting albumin derivatives lack the capacity to bind to metal ions such as cobalt ion. In the subject embodiment, an ischemic event is diagnosed by detecting the albumin derivatives that cannot bind metal ion. For this reason, the subject embodiment is referred to herein as the "derivative embodiment."

As is reported in the Examples, albumin having an acetylated terminal Asp or lacking four, three, two or even one N-terminal amino acid have been found to lack the capacity to bind to cobalt ion. It has been observed that albumin derivatives lacking four, three, two or one N-terminal amino acids are present in the serum or patients with ischemia.

The derivative embodiment of the subject invention comprises a method of detecting or measuring an ischemic event in a patient by: (a) contacting a patient sample comprising naturally-occurring albumin and optionally albumin N-terminal derivatives with an excess quantity of metal ion that binds to the N-terminus of naturally-occurring albumin, whereby albumin-metal complexes are formed; (b) partitioning the complexes from said derivatives, if any; (c) measuring at least one of said derivatives, if any; and (d) comparing said measured derivative to a known value, whereby the ischemic event may be detected or measured.

The derivative embodiment method can be practiced with a metal ion salt that is a salt of a transition metal ion of Groups 1 b-7b or 8 of the Periodic Table of the Element. Preferably, the metal ion salt is a salt of a metal selected from the group consisting of V, As, Co, Sb, Cr, Mo, Mn, Ba, Zn, Ni, Hg, Cd, Fe, Pb, Au and Ag. Most preferred is that the metal ion is Ni or Co. The minimum incubation period for metal ion and albumin is at least 4-5 minutes, and preferably 10 minutes, i.e., an amount of time sufficient for equilibrium to be reached. It is also preferred that heparin be added to the sample prior to the addition of the excess quantity of metal ion.

The partitioning step of the derivative embodiment method can be carried out in two ways. It can be effected by having the excess metal ion of step (a) bound to a solid support such that the resulting albumin-metal complexes are retained on the solid support, permitting the elution separation of the albumin N-terminal derivatives. Alternatively, a solution of excess metal ion can be added to the patient sample, permitting the albumin-metal complexes to form, and the partitioning can be effected by contacting the complexes with antibodies to the metal-albumin complex that are bound to a solid support.

Thus, in one aspect, the derivative embodiment involves a method comprising: (a) contacting a patient sample comprising naturally-occurring albumin and optionally albumin N-terminal derivatives with an excess quantity of a metal ion bound to a solid support, whereby the metal ion binds to the N-terminus of naturally-occurring albumin, forming metal-albumin complexes; (b) separating the complexes from said derivatives, if any; (c) measuring at least one of said derivatives, if any; and (d) comparing said measured derivative to a known value, whereby the ischemic event may be detected or measured. It is preferred that the solid support of step (a) be a diacetate or a phosphonate matrix. It is also preferred that the metal ion used in step (a) be nickel ion. It is further preferred that copper ion not be used in this method as it is likely to demonstrate non-specific binding to albumin thiol groups (located outside the N-terminus), possibly generating false negative results.

Metal affinity chromatography methods useful in this embodiment are within the skill in the art. For example, resins for separating proteins (including albumin) using metal affinity chromatography are described in U.S. Pat. Nos. 4,569,794; 5,169,936; and 5,656,729.

In another aspect, the derivative embodiment involves a method comprising: (a) contacting a patient sample comprising naturally-occurring albumin and optionally albumin N-terminal derivatives with an excess of a metal salt, whereby a metal-albumin complex is formed; (b) contacting the mixture of step (a) with an antibody to said complex, said antibody being bound to a solid support; (c) separating the complex from said N-terminal derivatives, if any; (d) measuring the amount of at least one N-terminal derivative, if any; and (e) comparing the measured N-terminal derivative to a known value, whereby an ischemic event may be detected or measured. In this aspect, it is preferred that the metal ion be cobalt ion.

The step of measuring the albumin N-terminal derivatives can be carried out using ligands known in the art such as antibodies (monoclonal or polyclonal) to the derivatives. The antibodies can be directed to one or more of the N-terminal epitopes for each derivative. Thus, one or more antibodies directed to one or more N-terminal epitopes may be used to measure the derivatives. Additionally, measuring can be accomplished by employing an antibody(ies) to albumin non-N-terminal epitopes. Because the partitioning step has removed all naturally-occurring albumin, any remaining albumin will be an N-terminal derivative. Antibodies used in the measuring step are labeled, preferably with an enzyme or a fluorescent label or by other methods known in the art.

The derivative embodiment methods can be carried out using kits having components adapted to provide the reactants or reagents and carry out the process steps. Where the derivative embodiment method involves excess metal ion bound to a solid support, the kit illustrated in FIG. 1 can be employed. Referring to FIG. 1, the diagnostic kit 20 is constructed of an upper plate 1 and lower plate 3. The lower plate 3 has 1-2 elongated solid supports 6 (e.g., nitrocellulose) with a sample application filter 4 upon which a patient sample is applied through sample port 2. The filter 4 and port 2 may be positioned such that the filter 4 is common or shared by both elongated solid supports 6. The filter 4 removes cells (red and white blood cells, platelets, etc.), permitting plasma to flow through to supports 6. The patient sample migrates from the filter at the first end of each of the elongated solid supports 6 to the second ends at the end of process indicators 18. The first solid support 6 provides a test function and the second provides a control function. The solid support providing a test function has an area 8 of immobilized metal ion to which naturally-occurring albumin binds. The albumin N-terminal derivatives continue to migrate down the solid support 6 to an area 10 containing ligand. In preferred embodiments, the ligands at area 10 are antibodies to albumin N-terminal derivatives and/or antibodies to naturally-occurring albumin. An antibody to naturally-occurring albumin may be used at area 10 provided it is directed to an epitope that is not located at the N-terminus of naturally-occurring albumin, so that it may bind to the derivatives. An antibody at area 10 to an albumin N-terminal derivative refers to an antibody directed to an N-terminal epitope of the derivative, such that the antibody is specific (i.e., recognizes only) the particular albumin N-terminal derivative. An advantage of including antibodies to albumin N-terminal derivatives at area 10 is that the amount of each or all N-terminal derivatives can be measured. Measurement of each derivative may permit a more accurate assessment of the degree and timing of the ischemic event. For example, a relatively higher concentration of the derivative lacking four N-terminal amino acids may reflect a greater degree or a longer duration of ischemia than a second sample where another derivative (e.g., albumin lacking only its N-terminal Asp residue) is more prevalent. Although the relative order of appearance of each derivative during the course of an ischemic event has not yet been determined, it will be possible to do so upon correlation of derivatives observed in patient samples with clinical observations of patients from whom the samples have been derived.

In the control (second) elongated solid support 6, an area 11 containing ligand to albumin is provided to detect all albumin, naturally-occurring or N-terminal derivatives, in the sample. Thus, the antibody at area 11 is directed to an albumin epitope that is not located at the N-terminus of albumin. The antibody or antibody mixture at areas 10 and 11 should be the same for control purposes.

The test and control results can be observed through ports 12 and 14, respectively. The binding of albumin or albumin N-terminal derivatives to antibody is detected by methods known in the art such as sandwich assays, enzyme assays or color indicators. For example, a labeled antibody may be added through ports 12 and 14 to bind to any albumin that is bound to antibody attached to areas 10 and 11. The label on the added antibody may be, for example, alkaline phosphatase, a commonly used reporter enzyme which reacts with synthetic substrates such as 1,2-doxetane or p-nitrophenylphosphate to yield detectable products. Alternatively, a protein coloring reagent such as bromo cresol purple or bromo cresol green may be present in areas 10 and 11 or added through ports 12 and 14.

Finally, an end of process indicator 18 at the second end of each elongated solid support 6 may be employed to assure completion of the test, i.e., that a sufficient volume of biological sample has passed down each elongated solid support 6 for the test to be completed. Suitable end of process indicators 18 include pH indicators and conductance indicators as is known in the art.

The kit illustrated in FIG. 1 can also be used where the derivative embodiment method employs a solid-support bound antibody to the albumin-metal complex. Referring again to FIG. 1, the patient sample is first mixed with excess metal ion aqueous solution, whereby naturally-occurring albumin-metal complexes are formed, and then applied to the filter 4 at the first end of the elongated solid supports 6. As the sample migrates down the test (first) elongated solid support 6, it encounters area 8 between the first and second ends which has immobilized antibody to the albumin-metal complex. The albumin-metal complex binds to area 8, and the N-terminal derivatives continue migration to area 10 containing ligand to albumin which is proximate the second end. The ligand at area 10 can be an antibody directed to an albumin epitope that is not located at the naturally-occurring N-terminus, or can be antibodies to derivative N-terminal epitopes. An end of process indicator 18 can also be present at the second end of the first elongated solid support. A second or control elongated solid support 6 can also be present in the kit 20 with an area 11 having immobilized antibody to the albumin located between the first and second ends.

Figure 2:
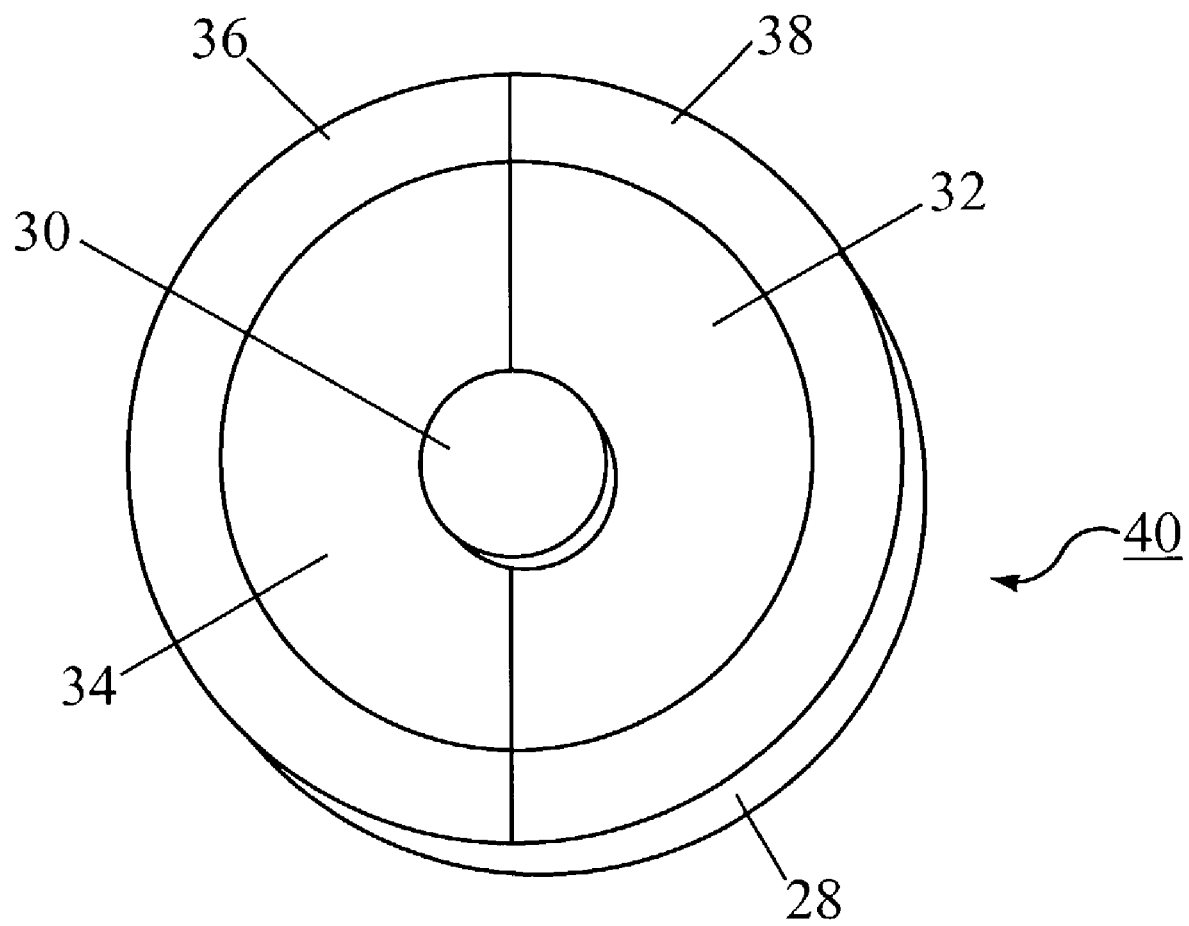

The subject invention provides additional kit embodiments suitable for the derivative embodiment method employing the solid support bound antibody to albumin-metal complex. Referring now to FIG. 2, a kit 40 is provided containing a solid support disk or circle 28 having a centrally located sample application filter 30 for application of a patient sample that has been mixed with excess metal ion, whereby naturally-occurring albumin-metal complexes have been formed. The circular filter is surrounded by an inner concentric ring divided into a test half 32 which contains ligand (e.g., a monoclonal antibody) to albumin-metal complexes, and a control half 34 which contain no ligand. Beyond the inner concentric ring is an outer concentric ring divided into a test half 38 and a control half 36, both of which contain ligand to albumin. In area 36, ligand is provided that detects all albumin, naturally-occurring or N-terminal derivatives, in the sample. Thus, the antibody at area 36 is directed to an albumin epitope that is not located at the N-terminus of naturally-occurring albumin. In area 38, ligand to naturally-occurring albumin and/or to albumin N-terminal derivatives is likewise provided. Again, for control purposes, the antibody or antibody mixture in areas 36 and 38 should be the same.

As the patient sample radiates from the filter 30, the albumin-metal complexes bind to antibody to complexes in area 32. Filtrate from area 32 passes into area 38, where albumin N-terminal derivatives bind to antibody. Likewise, as patient sample radiates through area 34 of the control half and into area 38, all albumin present (naturally-occurring and derivative) binds to antibody present in area 36. The amount of albumin or albumin derivatives bound in area 38 is compared to a known value to determine whether an ischemic event has occurred. The amount of albumin or derivatives in area 38 can also be compared to a scale of known values, such as a color scale, to determine the degree of the ischemic event. The amount of albumin or derivatives bound in area 38 is determined by methods known in the art including sandwich assays, enzyme assays or protein color reagents.

As can be appreciated by those skilled in the art, the embodiment in FIG. 2 can also be readily adapted to the derivative embodiment method in which metal ion is bound to the solid support. Specifically, the solid support area 32 would have metal ion bound thereto rather than antibody to albumin-metal complex.

Figure 3:
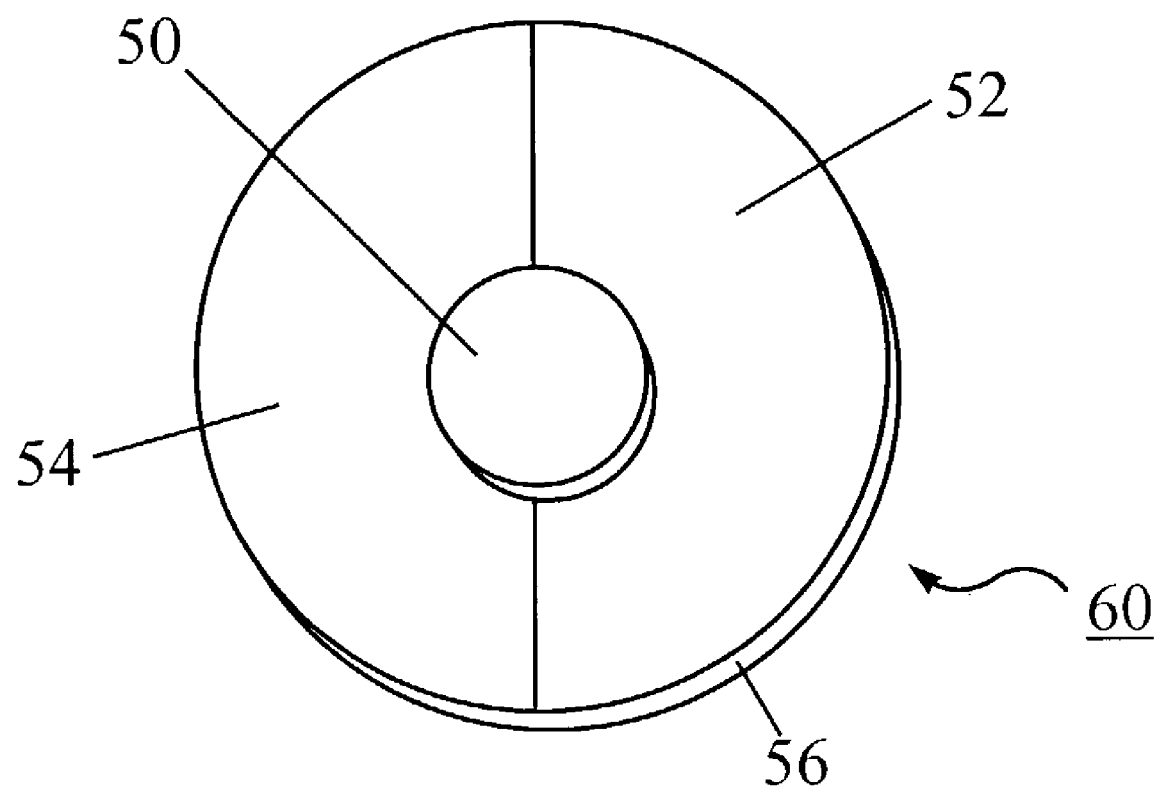

FIG. 3 illustrates another kit 60 suitable for the derivative embodiment method employing the solid support bound antibody to albumin-metal complex. The kit 60 comprises a circular solid support 56 with a centrally located sample application filter 50. The filter 50 is surrounded by a concentric ring which is divided into two semi-circles. The control semi-circle contains an area 54 containing ligand to naturally-occurring albumin and albumin derivatives, preferably an antibody directed to an albumin epitope not located at the N-terminus of naturally-occurring albumin. The test semi-circle contains an area 52 containing ligand to albumin-metal complex. Thus, after a patient sample is mixed with an excess metal ion solution, whereby albumin-metal complexes are formed, it is applied to filter 50 from which it radiates to area 52, where the albumin-metal complexes bind to the ligand. In the control semi-circle, the patient sample radiates and the naturally-occurring albumin (complexes) and derivatives bind to the ligand in area 54. The ligand in area 54 is preferably a monoclonal or polyclonal antibody directed to a non-N-terminal epitope of naturally-occurring albumin. By comparing the amount of total albumin and derivatives bound to area 54 to the amount of albumin-metal complexes bound to area 52, the amount of albumin derivatives can be calculated or estimated, and an ischemic event detected or measured. The albumin or derivatives bound to antibodies on each area (52 or 54) can be detected or measured by methods known in the art including sandwich assays, enzyme assays and protein color assays.

FIG. 3 can likewise be adapted to be useful in the derivative embodiment method in which metal ion is bound to the solid support, i.e., where metal ion is immobilized in area 52.

As is discussed above, a variety of antibodies are employed in the various embodiments of the subject invention. In the excess metal, endogenous copper and derivative embodiments, antibodies to albumin-metal complexes are employed. Patient antibodies specific to the albumin-metal (cobalt and nickel) complexes (including the N-terminal epitope) have been identified in occupational studies (Nieboer et al. (1984) Br. J. Ind. Med. 41:56-63; Shirakawa et al. (1992) Clin. Exp. Allergy 22:213-218; Shirakawa et al. (1990) Thorax 45:267-271; Shirakawa et al. (1988) Clin. Allergy 18:451-460; and Dolovich et al. (1984) Br. J. Ind. Med. 41:51-55). Additionally, rabbit antibodies to human albumin-metal complexes have also been generated (Veien et al. (1979) Contact Dermatitis 5:378-382). Therefore, antibodies to albumin-metal complexes for use in the subject methods either already exist in the art or would be readily obtainable using known methods.

In addition to the foregoing antibodies, the derivative embodiment may also use antibodies to one or more of the albumin N-terminal derivatives. As is set forth in the Examples, it has been found that the albumin derivatives that lack four, three, two and even one N-terminal amino acid have lost the capacity to bind to cobalt. Additionally, full-length albumin that has been acetylated at its Asp residue also cannot bind to cobalt. As is appreciated by the skilled artisan, antibodies that are specific to (i.e., recognize only) each of these derivatives can be obtained using known monoclonal antibody technology. Adjuvants such as KLH may be used to enhance immunogenicity.

Applications, embodiments and methods of the present invention comprising one or more of the aforementioned methods of the present invention include: A method for ruling-out the existence of ischemia in a patient, comprising application of any of the aforementioned methods, including application of any of the subject methods wherein said patient possesses one or more cardiac risk factors, said cardiac risk factors being selected from the group consisting of: age greater than 50, history of smoking, diabetes mellitus, obesity, high blood pressure, high cholesterol, and strong family history of cardiac disease. A variant thereof, comprises using the subject methods to detect ischemia in an individual during, before and/or after an exercise stress test (e.g., treadmill test) or a pharmacological stress test (e.g., dobutamine or other drugs known in the art). The patient samples obtained before, during or after application of stress are compared. Comparison of the before and after ischemia diagnostic tests will reveal whether the ischemic event is induced only under the elevated metabolic conditions of stress. This method may be used to detect the existence of ischemia provoked by exercise or pharmacological stress in an otherwise asymptomatic patient. The procedure can be repeated at desired intervals (e.g., 3 months, 6 months, etc.) for patient monitoring.

Other embodiments, applications and variants of the present invention include a method for ruling-out the occurrence of an temporally-limited ischemic event in a patient comprising application of any of the subject diagnostic methods; a method of detecting the existence of ischemia in an asymptomatic patient comprising application of any of the subject diagnostic methods; a method for the evaluation of patients suffering from stroke-like signs to determine the occurrence or non-occurrence of a stroke, comprising application of any of the subject diagnostic methods; a method for distinguishing between the occurrence of an ischemic stroke and a hemorrhagic stroke, comprising application of any of the subject diagnostic methods; and a method for assessing the efficacy of an angioplasty procedure, comprising application of any of the subject diagnostic methods.

The present invention also provides a method for evaluation of a patient presenting with angina or angina-like symptoms to detect the occurrence or non-occurrence of a myocardial infarction, comprising application of any of the subject diagnostic methods and application of an electrocardiographic test, followed by correlation of the results of the application of the diagnostic method with the results of the electrocardiographic test to determine the occurrence or non-occurrence of a myocardial infarction. Preferred electrocardiographic tests are E.C.G., E.K.G. and S.A.E.C.G. tests.

Another method of the present invention is a method for supplementing electrocardiographic results to determine the occurrence or non-occurrence of an ischemic event, comprising application of any of the subject diagnostic methods and application of an electrocardiographic test, followed by correlation of the results of application of the diagnostic method with the results of said electrocardiographic test to determine the occurrence or non-occurrence of an ischemic event. A variant thereof, comprises application of the method wherein said patient is undergoing surgery.

A further method of the present invention is a method for comparing levels of ischemia in patients at rest and during exercise is also taught by the present invention. Generally, ischemia can be measured in a patient during any suitable exercise, and at rest before and/or after exercise. Specifically, the method may comprise application of the following steps at designated times: (a) application of any of the subject diagnostic methods at a first designated time, (b) administration of an exercise treadmill test followed by a second application of the same diagnostic method employed in step (a), (c) comparing the results of the application of the diagnostic method prior to administration of the exercise treadmill test with the results of the application of the diagnostic method after administration of the exercise treadmill test, and (d) repeating steps (a) through (c) at additional designated times wherein, results obtained at designated time are compared. This embodiment may be used to evaluate patients with known or suspected ischemic conditions, to assess the patency of an in-situ coronary stent and to assess the efficacy of an angioplasty procedure. Preferred designated time intervals are three months, six months or one year.

The present invention also teaches a method for assessing the efficacy of thrombolytic or other drug therapy (i.e., drugs to attenuate an ischemic event by conditioning ischemic myocardium), comprising the application of any of the subject diagnostic methods; and a method for detecting in a pregnant woman the occurrence of placental insufficiency, comprising application of any of the subject diagnostic methods.

The subject invention also includes calibration standards which are useful in calibrating analyzers or kits that employ the subject methods. In a clinical diagnostics setting it is necessary to develop an assay calibration system to quantify the analyte, standardize the test values across different instruments, and to control for drift in test reagents as the assay components age. A number of calibration schemes have been developed for use with the subject diagnostic methods.

In one embodiment, the calibrator compositions are standards to be used to generate standard curves for calibration of clinical chemistry analyzers such as the Beckman CX-5™, Roche Cobas Mira™ and Dimension XL™. These analyzers can each detect or measure ischemic events based on the calorimetric version of the excess metal embodiment described herein. The calibrator compositions can also be used to calibrate analyzers such as atomic absorbance or atomic emission spectrophotometers.

In one embodiment, the calibrator compositions have preselected or predetermined ratios of naturally-occurring albumin and metal ion. In preferred embodiments, the albumin is human, the solution is buffered (e.g., Tris or HEPES), the pH is about 7-8, and the metal is divalent and is selected from the group consisting of cobalt, nickel and copper. Aliquots of these calibrators, under specific conditions, produce a defined absorbance at 470-500 nm, i.e., a standard curve.

The albumin that is used in the foregoing albumin/metal calibrators is substantially all naturally-occurring. By "substantially all," it is meant that at least 70%, and with increasing preference, at least 80%, 90%, 95%, 99% by weight, and optimally 100% by weight of the albumin is full length. Without wishing to be bound by theory, it is believed that when the albumin/metal calibrator compositions are placed in, solution, the metal ion becomes primarily bound to the N-terminus of the albumin, although it is possible that a minor amount of metal ion can be bound to thiol or other groups located on the albumin.

The albumin/metal calibrators are typically manufactured by starting with initial concentrated solutions of pure albumin and metal-saturated albumin, and then mixing these concentrates in defined ratios to obtain desired molar ratios of albumin and metal concentrations in the resulting calibrator solutions.

To generate the standard curve for the colorimetry-type analyzers, each of the calibrator solutions is mixed with a known, constant amount of excess metal salt and excess coloring reagent as described herein. Thereafter, absorbance is measured at 500 nm and blocked albumin is plotted against absorbance. Because the amount of metal originally present in the calibrator solution and the excess metal salt added are both known, the absorbance, which is associated with the excess metal ion that did not bind to albumin, can be correlated with degree of N-terminal blockage of albumin originally present in the calibrator solution. As the degree of N-terminal blockage, i.e., percentage of original metal concentration, in the calibrator solution increases, the absorbance due to excess metal ion that does not bind to albumin also increases. The relationship is linear.

To generate the standard curve for the atomic absorbance or atomic emission spectrophotometer, the calibrator solutions are applied to the analyzer. The absorbance is plotted against the original metal concentration present in each calibrator to generate the standard curve.

Thus, the albumin/metal calibrator solutions are designed and intended to mimic ischemic patient samples in reflecting a range of albumin that is already bound to metal ion and is unavailable for binding to exogenously added metal ion. For example, a calibrator solution that has 75% of its albumin blocked with Cu at its N-terminus has only 25% of its albumin available for binding to exogenous, excess Co. After addition of coloring reagent to react with unreacted Co, absorbance at 500 nm will be much greater than that which would be observed for a calibrator solution that is only 25% blocked with Cu at its N-terminus.

For quality control purposes, the characteristics of the albumin/metal calibrators can be verified by:

1. measuring their metal to albumin ratio; metal can be measured by atomic absorption, and albumin can be measured by bromo cresol green (BCG) assay;

2. using radioactive $Co^{57}$ albumin binding assay employing a Sepharose column;

3. measuring the absorbance of the calibrators at the appropriate wavelength over time; and 4. measuring the absorbance of mixtures of calibrator solutions and excess cobalt plus coloring reagent, such as dithiothreitol (DTT).

To improve the range of the calibration curve, i.e., to encompass the total normal and ischemic patient range, the foregoing albumin/metal calibrator strategy can be modified to provide both increased and decreased numbers of albumin metal binding sites. Greater calibration range is achieved by adding higher concentrations of full length albumin to increase metal binding capacity and by adding diluted concentrations of albumin to lower binding capacity. This is an important issue in selecting a calibrator material because the calibration curve range should ideally encompass the total normal and ischemic patient range.

In a variation of the albumin/metals calibrator embodiments, various dilutions of pooled patient serum can be used in place of purified albumin to produce the standard curve.

In another embodiment, the calibrators comprise synthetic albumin N-terminal peptides and varying concentrations of metals, e.g., copper or cobalt. Thus, calibrator solutions containing different molar ratios of peptide and metal are obtained by mixing different ratios of peptide-metal concentrate and peptide concentrate. This embodiment provides an improvement because increasing the peptide concentration increases the metal binding capacity of the metal saturated calibrator, thereby increasing the standard curve range. Use of synthetic peptides has the further advantage of providing a more consistent product, employing a more stable bio-molecule than purified intact albumin and the preparation contains no human source material capable of transmitting disease.

Albumin N-terminal peptide concentrate can also be used in place of full length albumin concentrate to obtain increased metal binding capacity in full-length albumin calibrator solutions discussed above.

In another embodiment, the calibration strategy employs dilutions of full-length albumin in predetermined concentrations. Metal ion solution of constant concentration is mixed with the various dilutions of albumin. As the albumin concentration decreases, less metal ion binding sites are available, and more metal ion remains unbound. DTT or other coloring compound is added and absorption is measured, whereby a standard curve can be generated.

Likewise, the calibration scheme can employ dilutions of albumin N-terminal peptides in predetermined concentrations, to which metal ion solution of constant concentration is added. Coloring compound is added, absorption measured, and a standard curve generated.

In another embodiment, the calibration scheme uses different concentrations of cobalt rather than different concentrations of a cobalt binding materials. Specifically, no sequestering agent such as albumin is used and the calibrator reaction is simply reaction of non-sequestered cobalt with the colored detection agent, e.g., DTT. This procedure is the simplest and the most economical. Moreover, addition of more or less cobalt can easily expand the calibration concentration range.

In a further embodiment, the calibration scheme uses metal chelating agents such as EDTA (ethanolamine diamine tetracetic acid) in place of albumin or albumin N-terminal peptides. Other chelating agents that bind to cobalt and copper are known in the art and may include oxalate and citrate. This method, unlike using the simple cobalt calibrators, can be readily adapted to automated clinical chemistry analyzers where the assay protocol for generating a calibration curve must be the same sequence of steps used for measuring controls and patient samples. Dilutions of EDTA or other chelator calibrators in predetermined molar concentrations are mixed with metal ion (cobalt), and function like and in place of albumin, to sequester metal ion. When the metal ion (cobalt) solution of constant, predetermined concentration is added to the chelator calibrators, the cobalt is prevented to varying degrees from reacting with DTT (or other colored indicator) to form a detectable calorimetric product. In this manner, a standard curve is generated. Chelators such as EDTA are very stable, are simple and consistent raw material for producing calibrators, are cost effective, and, as non-human source materials, are free from biohazard. As is discussed in the Examples, it has been found that the EDTA calibrators produce a linear curve that successfully spans the ACBTM Test (Ischemia Technologies, Inc., Denver, Colo.) dynamic range allowing normal and ischemic patients to be measured. The ability to titrate EDTA levels to adjust calibrators allows for more consistent manufacturing and less lot to lot variability.

In another embodiment, the calibrators comprise mixtures of different molar ratios of N-terminal albumin derivatives. Specifically, the calibrators are made by mixing in varying ratios, concentrated solutions of full length albumin and one or more N-terminal derivatives. These derivatives can be −1 to −4 derivatives and/or the acetylated N-terminal derivative. These calibrators can be used in the ischemic diagnostic assay described herein in which albumin derivatives are detected and/or measured. The molar ratio of full-length to derivative albumin is preferably between 0.1:1 and 1:0.1. Additionally preferred ratios are 3:1, 1:1 and 1:3.

A greater understanding of the present invention and of its many advantages may be had from the following examples, given by way of illustration. The following examples are illustrative of some of the methods, applications, embodiments and variants of the present invention. They are, of course, not to be considered in any way limitative of the invention. Numerous changes and modification can be made with respect to the invention.

EXAMPLES

Example 1

Sample Handling Procedures for Ischemia Testing

The samples which were used in the present invention were obtained from a variety of tissues or fluid samples taken from a patient, or from commercial vendor sources. Appropriate fluid samples included whole blood, venous blood, arterial blood, blood serum, plasma, as well as other body fluids such as amniotic fluid, lymph, cerebrospinal fluid, saliva, etc. The samples were obtained by well known conventional biopsy and fluid sampling techniques. Preferred samples were blood plasma and serum and purified albumin. Purified albumin was isolated from the serum by any of the known techniques, including electrophoresis, ion exchange, affinity chromatography, gel filtration, etc.

Blood samples were taken using Universal Precautions. Peripheral venipuncture was performed with the tourniquet on less than 30 seconds (contralateral arm from any IV fluids). Blood is drawn directly into two 10 cc Becton Dickinson Vacutainer® Sodium-Heparinized tubes and was gently inverted once to mix. If an IV port was in use, the blood was collected (after a discard sample was drawn equivalent to the dead space of usually 5 cc) into a plain syringe and dripped gently down the side of two 10 cc Becton Dickinson Vacutaine® brand tubes and gently inverted once to mix. Blood was also collected directly from the Vacutainer® tubes with special administration sets with a reservoir system that does not require a discard sample. These systems allow a draw to be taken proximal to the reservoir.

Plasma tubes were centrifuged within 2 hours of the draw. (Note, collected serum was clotted between 30-120 minutes at room temperature (RT) before centrifugation. The inside of the serum tube was ringed with a wooden applicator to release the clot from the glass before centrifugation. If the subject was taking anti-coagulants or had a blood clotting dysfunction, the sample was allowed to clot longer than 60 minutes, between 90-120 minutes was best.) The tubes were centrifuged for 10 minutes at RT at 1100 g (<1300 g). Collected samples were pooled in a plastic conical tube and inverted once to mix.

If the sample was not used within 4 hours of centrifugation, the sample was frozen. Alternatively, separated serum was refrigerated at 4° C. until tested, but was tested within 8 hours (storage over 24 hours may have resulted in degradation of the sample). "Stat" results (obtained within 1 hour of completion of centrifugation step) were preferred. The following percent differences for the ischemia test were measured using plasma and serum samples ≦8 hours and ≦24 hours after collection. Delayed test results were compared to stat test results on the same patient sample and the mean percent differences (and standard deviations) were as given below:

| Storage and Delayed Testing Data for the Ischemia Test | | | | |
| --- | --- | --- | --- | --- |
| | ≦8 hrs. vs. stat | | ≦24 hr. vs. stat* | |
| Plasma (stored at | n % diff | 20 −5.3% | n % diff | 23 −4.8% |

-continued

Storage and Delayed Testing Data for the Ischemia Test

|  |  | ≦8 hrs. vs. stat |  | ≦24 hr. vs. stat* |
|---|---|---|---|---|
| room temp) | S.D. | .094 | S.D. | .090 |
| Plasma | n | 18 | n | 40 |
| (stored at | % diff | 1.7% | % diff | 1.0% |
| 4° C.) | S.D. | .070 | S.D. | .094 |
| Serum | n | 16 |  |  |
| (stored at | % diff | −12.8% | (not enough |  |
| room temp) | S.D. | .157 | samples) |  |
| Serum | n | 14 | n | 24 |
| (stored at | % diff | −7.3% | % diff | −2.7% |
| 4° C.) | S.D. | .040 | S.D. | .210 |

*≦24 hr. test results given here are a total that include the ≦8 hr. test sample results.

Example 2

Test Method for Detecting Occurrence of Ischemic Event Using Cobalt Binding

The ischemia test (cobalt version) was run as follows: 200 µl of patient sera was added to each of two tubes each containing 50 µl 0.1% $CoCl_2.6H_2O$. The mixture was allowed to react at room temperature (18-25° C.), or higher, for 5 or more minutes. Thereafter 50 µl 0.01 M dithiothreitol (DTT) was added to one of the two tubes (the "test tube") and 50 µl 0.9% NaCl was added to the second tube (the "background tube"). After two minutes, 1 ml 0.9% NaCl was added to both tubes. A470 spectroscopy measurements were taken of the two tubes. The ischemia test was considered positive if the optical density was greater than or equal to 0.400 OD (or alternatively a clinically derived cut-off) using a spectrophotometer at OD 470 nm.

Equivalent materials which may be used as alternatives include any of the transition metals. Ferrozine or other compounds with an affinity to cobalt can be substituted for DTT and/or any cobalt or metal coloring reagent. $CoCl_2.6H_2O$, for instance, can be utilized. The optimal range for cobalt binding to albumin is from pH 7 to pH 9, with a range of pH 7.4-8.9 being most preferred; pH 9 is optimal for cobalt interaction with the color reagent. The amount of serum sample can also vary, as can the amounts of $CoCl_2.6H_2O$ and DTT and ferrozine. Critical, however, is that the amount of cobalt used be in excess of the amount of albumin and that the DTT or ferrozine be in excess of the cobalt.

Example 3

Test Method for Detecting Occurrence of Ischemic Event Using Measurement of Copper Albumin was purified from 0.2 cc of human serum or plasma using an ion exchange method to produce approximately 8 mg of purified albumin. A buffer having a pH in the range of 7 to 9 was added. The amount of copper present in the sample was then measured by direct spectrophotometric and potentiometric methods, or by any of several other known methods, including atomic absorption, infrared spectroscopy, HPLC and other standard or non-standard methods, including radioactive tracer techniques. The proportion of copper to albumin can be then used as a measure of ischemia, the greater the proportion, the higher the ischemia value.

Example 4

Test Method for Ruling-Out the Existence of Ischemia in a Patient

The following protocol is designed to rule out ischemic conditions in healthy appearing patients who describe prior symptoms of occasional chest pain or shortness of breath.

First, a medical history (including a detailed history of the present and past medical problems and risk factors for ischemic heart disease), physical exam, and vital signs are obtained. If the patient has any cardiac risk factor for ischemic heart disease (age>50, smoking, diabetes mellitus, obesity, high blood pressure, elevated low density lipoproteins, high cholesterol, and strong family history of cardiac disease), the physician is instructed to order a resting twelve-lead EKG and a chest x-ray. If the twelve-lead EKG shows evidence of an acute myocardial infarction (AMI), the patient is immediately transported to a hospital for intensive cardiac treatment. If the twelve-lead EKG does not show evidence of (AMI), the patient will be scheduled for an outpatient twelve-lead EKG exercise treadmill within the next few days. A blood sample should be drawn immediately before and again after the exercise treadmill test and the ischemia test run on each sample.

If the exercise treadmill test shows definite evidence of cardiac ischemia, usually seen by characteristic changes of the ST segments, dramatic abnormalities of pulse or blood pressure, or anginal chest pain, the patient should be treated for cardiac ischemia and referred to a cardiologist for possible coronary angiogram and angioplasty. If the exercise treadmill test does not show any evidence of cardiac ischemia, or the findings are equivocal, but the ischemia test is abnormal, the patient similarly should be treated for cardiac ischemia and referred to a cardiologist for possible coronary angiogram and angioplasty. (Absent the present invention, such patients with moderate to high cardiac risk factors would be referred to a cardiologist for further (typically invasive) cardiac testing).

If the exercise treadmill test does not show any evidence of ischemic heart disease, or the findings are equivocal, and the ischemia test is normal, the patient may be sent home with no evidence of cardiac ischemia. In comparison, prior to the present invention, in the case where the exercise treadmill test does not show any evidence of cardiac ischemia, or the findings are equivocal, patients with low risk for cardiac ischemia typically would not have any other tests ordered. In such cases, the physician is taking a calculated risk. It is well documented in the medical literature that at least 25 to 55 percent of patients (higher in females) will have some ischemic heart disease which is not found with routine exercise treadmill testing.

Example 5

Test Method for Evaluating Patients with Angina to Rule-Out the Occurrence of an Ischemic Event In this study, clinical criteria (EKG changes, elevated cardiac enzymes or markers, positive thallium treadmill or positive angiogram) were used to determine the presence or absence of ischemia in patients presenting with chest pain. Ischemic patients were those with at least one clinical finding positive for ischemia. Normal patients were those for whom clinical findings were negative, as well as normal volunteers with no history or symptoms of cardiac or cerebral ischemia.

Blood samples were taken from 139 subjects who either presented to emergency departments of several hospitals with chest pain or normal volunteers. Blood was drawn into plain red top tubes and, after ten minutes, the clotted blood was centrifuged to separate the serum. Serum was refrigerated at 4° C. until tested. If the sample would not be used within 4 hours of centrifugation, it was frozen, but in no case was testing delayed more than 3 days.

Samples were centrifuged for 5-10 minutes in an analytical centrifuge immediately before testing. 200 µl off each sample was aliquoted in triplicate with an additional tube to be used as a Blank (no DTT) control into borosilicate glass tubes. Also aliquoted was 200 µl of a Standard, such as Accutrol or HSA, in triplicate plus a Blank control. At 10 second intervals, 50.0 µl of 0.10% $CoCl_2$ (store working stock and stock at 4° C.) was added to each tube. Solution was added to the sample, not glass, and tubes were "flicked" to mix.

After 10.0 minutes (starting with the first tube to which cobalt solution was added) an additional 50.0 µl of 0.9% NaCl was added to the two Blank tubes using the appropriate 10 second intervals. 50.0 µl of 0.01 M DTT was additionally added to the Plasma (not Blank) tubes in their appropriate 10 second intervals. Of note, it is preferred that DTT be made fresh weekly (6 mg per 4 ml $H_2O$) and stored at 4° C.

After 2 minutes (starting with the first tube to which cobalt solution was added) 1.0 ml of 0.9% NaCl solution was added to each tube, using the appropriate 10 second intervals. Tubes were agitated to mix. In the event that there were too many tubes to finish the test tubes in 10 second intervals, reagents were added to the "Blank" tubes without timing.

The optical density of each sample set was read using the set's Blank to read absorbance at 470 nm. The cuvette was checked for air bubbles before reading and washed with $H_2O$ between sets. The ischemia test was considered positive if the optical density was greater than or equal to 0.400 using the spectrophotometer at OD 470 nm.

The results of the ischemia test compared to the diagnosis determined by clinical criteria are as described in the chart below. Four false negatives and three false positives were reported.

|  |  | Ischemia Test | |
| --- | --- | --- | --- |
| Clinical Diagnosis |  | + | − |
| + | 99 | 95 | 4 |
| − | 40 | 3 | 37 |

Study results demonstrated that the ischemia test marker has a higher value in patients with clinically diagnosed ischemia. The diagnostic accuracy of the ischemia test for the chest pain study was above 90 percent (sensitivity, 96.0%; specificity, 92.5%; predictive value, (+)96.9%; predictive value, (−) 90.2%).

Example 6

Test Method For Evaluation of Patients Suffering from Chest Pain to Determine the Occurrence or Non-Occurrence of a Myocardial Infarction The following study is proposed to test the ability of the present invention to detect ischemia in the initial hours following the onset of chest discomfort suspicious for cardiac ischemia. The cobalt version of the test is used.

The patient population is limited to male or female persons, 30 years or older, who present to the Emergency Department with complaints of chest discomfort of less than four hours in duration for reasons independent of the study. Patients will be excluded from the study if they meet any of the following criteria: (1) known concurrent non-cardiac ischemic disease(s), including but not limited to transient ischemic attacks, cerebral vascular accident, peripheral vascular disease, intermittent claudication, bowel ischemia, and severe renal failure; (2) definite radiological evidence of a cause of chest discomfort that is other than cardiac ischemia, such as, but not limited to, pneumonia, pneumothorax, and pulmonary embolus; or (3) chest discomfort temporally related to local trauma.

All standard evaluation and treatment appropriate for emergency department patients with suspected cardiac ischemia will be followed at all times. The drawing of blood for the study will not in any manner modify the standard treatment protocol. Within these parameters, a pre-treatment evaluation will be conducted, which will include documentation of all current medications, documentation of previous medical history, EKG, laboratory and radiographic test results, and documentation of most recent vital signs and a physical examination.

The study consists of drawing an extra blood sample at the time of admission to the emergency department. Samples are collected from a catheter that is already in place for intravenous access or alternatively by venipuncture. Collection and administration of the ischemia test is as described in Example 5 herein.

Example 7

Test Method for Detection of Ischemia in Patient at Rest and During Exercise

The primary objective of this trial was to employ and test the sensitivity of the ischemia test at various time points, before, during and after an exercise thallium treadmill test. Preliminary data has shown that the blood level of the ischemia test (i.e., absorbance, cobalt excess metal embodiment) rises immediately after an ischemic event. The purpose of this pilot investigation is to determine the magnitude of this rise in level of the ischemia test during a test to define the presence or absence of a cardiac ischemic event, said test being the exercise thallium treadmill test. While it is possible that patients scheduled for exercise thallium treadmill test may have already experienced an ischemic event, preliminary data indicates that a further, significant decline in cobalt binding (and an increase in the serum absorbance or unbound metal ion) will occur if tissue ischemia is induced during the exercise thallium treadmill test.

Patients already scheduled for an exercise thallium treadmill test were asked to give their consent for participation which required two tubes of blood (20 cc's) to be drawn up to 5 (five) times before, during and after the exercise thallium treadmill test. Eligible patients consisted of patients who met all of the following criteria: (1) Age: 18 years or older; (2) Male or female; (3) able to provide written informed consent; and (4) referred for exercise thallium treadmill test for reasons independent of this investigation. Patients were excluded from participation in the study if they met any of the following criteria: (1) known concurrent non-cardiac ischemic disease including, but not limited to: transient ischemic attacks, cerebral vascular accident, acute myocardial infarction and intermittent claudication; (2) inability to complete the standard protocol for the exercise portion of the exercise thallium treadmill test; or (3) cardiac arrest during the exercise portion of the exercise thallium treadmill test.

Prior to administration of the exercise thallium treadmill test, a pretreatment evaluation was conducted which included documentation of all current medications, documentation of previous medical history, EKG, laboratory and radiographic test results, and documentation of most recent vital signs and physical examination.

The standard exercise thallium treadmill test procedure was followed at all times. In no instance was the drawing of the additional blood samples for the purpose of the study permitted to subject the patient to additional risk (beyond the drawing of blood), or to in any manner modify the treatment of the patient.

The "standard" exercise thallium treadmill test procedure comprised generally the following: The patient was brought to the exercise test room in a recently fasting state. After initial vital signs and recent history was recorded, the patient was connected to a twelve-lead EKG monitor, an intravenous line was established and the patient was instructed in the use of a treadmill. With the cardiologist in attendance, the patient walked on the treadmill according to the standard Bruce protocol: starting at a slow pace (approx. 1.7 mph) and gradually increasing both the percent grade (slope) of the treadmill and the walking speed at three minute intervals up to a maximum of 5.5 mph at 20° grade. Termination of the exercise portion on the exercise thallium treadmill test occurred at the discretion of the cardiologist based on patient symptoms, EKG abnormalities, or the attainment of about 85% maximal heart rate.

With the patient near maximal effort on the treadmill, approximately 3 mCi of thallium$^{201}$ was injected intravenously while the patient continued to exercise for approximately one more minute. At the end of exercise, single photon emission computerized tomography (SPECT) was used to scan the patient's myocardium for any perfusion defects. Following recovery, between 2 and 4 hours after exercise, a smaller amount of thallium$^{201}$ (approximately 1.5 mCi) was re-injected for repeat SPECT scan. EKG's and SPECT scans were analyzed for ischemic criteria. The SPECT scans may show fixed and reversible perfusion defects. The reversible perfusion defects indicate ischemia and the fixed defects indicate myocardial scarring.

The study consisted of drawing blood samples on 3 occasions during the exercise thallium treadmill procedure. Two tubes of blood (approximately 4 teaspoons) were collected before the exercise test, immediately after exercise, and between 1 and 4 hours after exercise. Blood samples were collected from the catheter already in place for the exercise thallium treadmill procedure or alternatively by venipuncture. Note: Radiation Protection/Safety Considerations— Blood drawn following thallium$^{201}$ injection was routinely considered safe because the amount injected was approximately 3 mCi and, for all practical purposes, the dilution into the systemic circulation reduces the sample level to less than 0.67 nanoCi per cc.

Standard patient follow-up was conducted according to clinical practice. Patients who had subsequent coronary angiograms after being enrolled in this exercise thallium treadmill test study had all resultant coronary angiogram information obtained recorded to verify the exercise thallium treadmill test results.

All clinical and research laboratory testing procedures were performed in a blinded fashion.

Of the 59 patients enrolled (plasma and serum samples tested by the ischemia test method), 11 patients were deleted because of one of the following reasons: a chronically occluded coronary artery and no sample collected later than one hour after exercise, a clinical history of exercise leg pain (claudication), hemolyzed baseline blood samples, patient did not continue with the exercise study or did not agree to further blood tests, patient received an exercycle thallium test instead of a treadmill thallium test and one patient whose chest pain was later determined to be due to pneumonia.

Of the remaining 48 patients, 23 had no history of known ischemic heart disease, 23 had prior ischemic heart disease requiring angioplasty or coronary artery bypass grafts and 2 had prior myocardial infarctions but did not receive angioplasty or coronary artery bypass grafts. In the subgroup of 23 patients with no prior history of ischemic heart disease (using a total outcome score of $\geq 9$ and a $\geq 4.7\%$ increase in Ischemia Test values (i.e., absorbance associated with unbound excess metal ion) either one or three hours after exercise as positive for ischemia) there were 2 true positives, 15 true negatives, 6 false positives and 0 false negatives for a sensitivity of 100% and a specificity of 72%.

Using the same criteria for positive exercise thallium treadmill and Ischemia Test results, the entire 48 patients (including patients with and without a prior history of ischemic heart disease) had 6 true positives, 29 true negatives, 11 false positives and 2 false negatives for a sensitivity of 75% and a specificity of 73%.

Changing the positive criteria to a total thallium treadmill outcome score of $\geq 10$ and a $\geq 5.4\%$ increase in Ischemia Test values one hour after exercise for the entire 48 patients (including patients with and without a prior history of ischemic heart disease) gave 3 true positives, 37 true negatives, 7 false positives and 1 false negative for a sensitivity of 75% and a specificity of 88%.

Example 8

Assessing Efficacy of an Angioplasty Procedure

Percutaneous transluminal coronary angioplasty ("PTCA"), also referred to as coronary artery balloon dilation or balloon angioplasty, is an established and effective therapy for some patients with coronary artery disease. PTCA is an invasive procedure in which a coronary artery is totally occluded for several minutes by inflation of a balloon. The inflated balloon creates transient but significant ischemia in the coronary artery distal to the balloon. The result, however, is a widening of a narrowed artery.

PTCA is regarded as a less traumatic and less expensive alternative to bypass surgery for some patients with coronary artery disease. However, in 25 to 30 percent of patients, the dilated segment of the artery renarrows within six months after the procedure. In these cases, either repeat PTCA or coronary artery bypass surgery is required. Additionally, complications from angioplasty occur in a small percentage of patients. Approximately, 1 to 3 percent of PTCA patients require emergency coronary bypass surgery following a complicated angioplasty procedure.

The present invention addresses both problems by providing a means for monitoring on-going angioplasty procedures and by providing a mechanism for monitoring the post-angioplasty status of patients.

Twenty-eight patients already scheduled for emergent or elective angioplasty had blood samples (20 ml) drawn just prior to undergoing PTCA ("baseline") at 6, 12 and 24 hours after the last balloon deflation, and three tubes (25 ml) at 1 minute and 6 minutes after the last balloon deflation. Collection and administration of the test was as described in Example 5 herein. A detailed description of the angioplasty procedure was also recorded so the magnitude of 'downstream' ischemia could be estimated. This included catheter size, number of inflations, inflation pressure, duration of inflation, number of vessels involved and location.

The eligible patient population consisted of male or female patients who met all of the following criteria: (1) 18 years or older; (2) referred for PTCA for reasons independent of the study; (3) able to give written, informed consent; and (4) and did not possess any of the exclusionary criteria. Patients were excluded if they met any of the following criteria: (1) patients who were to have PTCA performed with a perfusion catheter; (2) patients with known, concurrent ischemic disease including, but not limited to transient ischemic attacks, cerebral vascular accident, acute myocardial infarction and intermittent claudication. Prior to PTCA, a pretreatment evaluation was conducted which included documentation of all concurrent medications and the taking of a blood sample for ischemia test administration and baseline (this occurred after the patient had been heparinized and the sheath placed).

The standard PTCA protocol was followed at all times. In no instance was the drawing of the additional tubes of blood permitted to subject the patient to additional risk (beyond the drawing of the blood), or modify the standard protocol.

The "standard" PTCA protocol generally comprised the following: The patient was transported to the cardiac catheterization laboratory in the fasting state. The right groin draped and prepped in the usual sterile fashion. Local anesthesia was administered consisting of 2% lidocaine injected subcutaneously and the right femoral artery entered using an 18 gauge needle, and an 8 French arterial sheath inserted over a guide wire using the modified Seldinger technique. Heparin, 3000 units, was administered I.V. Left coronary cineangiography was performed using Judkins left 4 and right 4 catheters, and left ventricular cineangiography performed using the automated injection of 30 cc of radiocontrast material in the RAO projection. After review of the coronary angiography, PTCA was performed.

The diagnostic cardiac catheter was then removed from the femoral sheath and exchanged for a PTCA guiding catheter which was then positioned in the right or left coronary ostia. An additional bolus of intravenous heparin, 10,000 units, was administered. A coronary guidewire, usually a 0.014 inch flexible tipped wire, was then advanced across the obstruction and positioned distally in the coronary artery. Over this guidewire, the balloon inflation system was inserted, usually consisting of a "monorail" type balloon dilation catheter. Sequential balloon inflations were made, with angiographic monitoring between inflations. The duration of the inflations varied among operators, but averaged approximately 45-60 seconds; occasionally prolonged inflations between 3 and 15 minutes were performed.

When it was determined that adequate opening of the coronary stenosis had been achieved, the balloon catheter was fully withdrawn and coronary angiograms performed with and without the guidewire in position. If no further intervention was believed to be necessary, the sheath was then sewn into position and the patient transported to either the intensive care unit or observation unit. The sheath was removed after approximately 6 hours and firm pressure applied with a C clamp or manual pressure. The patient remained at bed rest for approximately 6 hours after sheath removal.

Standard patient follow up was conducted according to clinical practice.

As stated, sample collection and administration of the ischemia test occurred essentially as described in Example 5 herein. The test technician was masked to the time the PTCA sample was taken.

Compared to baseline, 26 of the 28 tested patients demonstrated increased ischemia values after balloon inflation. The remaining two patients registered false negatives, both of which started with baseline values above 0.400. The mean increase in the ischemia test value from baseline to balloon inflation was 15.2%. Of the 21 patients that had 5 hour samples tested, all but three demonstrated a decreased ischemia test value compared to that measured during balloon inflation. Study results demonstrated that the ischemia test marker rises almost immediately following controlled onset of ischemia during the angioplasty procedure. The rapid rise of the marker during balloon inflation and its descent over a five hour period correlated with the controlled start and stop of ischemia. The diagnostic accuracy of the study was 96 percent.

Example 9

Evaluation of Post-Myocardial Infarction Patients

In a second study, three subsets of patients—patients without acute myocardial infarction (NonAMI), patients with acute myocardial infarction (AMI), and patients without AMI with significant collateral circulation (NonAMI collateral)—all of whom were undergoing emergent or elective angioplasty had blood samples collected prior to PTCA, immediately after balloon deflation, 6 hours after the procedure, and 24 hours after the procedure. A total of 63 patients were tested. The standard PTCA protocol (as described in Example 8) was followed.

During PTCA, blood was drawn into a syringe and then transferred to sodium-heparinized tubes. Post PTCA samples were drawn into green top sodium-heparinized tubes. In all other regards, sample collection and administration of the ischemia test occurred essentially as described in Example 5 herein. The test technician was masked to the time the PTCA sample was taken.

The ischemia test was considered positive if it increased between baseline and immediately after balloon angioplasty. The results of the study showed a statistically significant rise (p=0.0001) in the ischemia test marker following balloon angioplasty and a return to baseline within 24 hours. The mean percent increase for all patients in the study was 9.4%.

| TIME POINT | N | MEAN | SD | MEAN DIFF FROM BASELINE | SD | MEAN % DIFF FROM BASELINE | SD | P-VALUE |
|---|---|---|---|---|---|---|---|---|
| Baseline | 62 | .354 | .0424 | — | — | — | — | — |
| Immed. post PTCA | 63 | .385 | .0411 | .0310 | .0382 | 9.4% | .1178 | .0001 |
| 6 hours post PTCA | 57 | .368 | .0513 | .0150 | .0505 | 5.0% | .1507 | .0167 |

-continued

| TIME POINT | N | MEAN | SD | MEAN DIFF FROM BASELINE | SD | MEAN % DIFF FROM BASELINE | SD | P-VALUE |
|---|---|---|---|---|---|---|---|---|
| 24 hours post PTCA | 43 | .363 | .0474 | .0090 | .0444 | 3.2% | .1312 | .1221 |

| % CHANGE FROM BASELINE | WITH AMI | | | WITHOUT AMI | | | T-TEST |
|---|---|---|---|---|---|---|---|
| | N | MEAN | SD | N | MEAN | SD | P |
| Immed Post PTCA | 19 | .083 | .137 | 41 | .101 | .111 | .0001 |
| 6 hrs Post PTCA | 15 | .091 | .137 | 39 | .027 | .153 | .2676 |
| 24 hrs Post PTCA | 14 | .130 | .158 | 27 | .019 | .081 | .2240 |

A side branch occlusion ("SBO") occurs when, as a result of balloon inflation, a side artery becomes obstructed, causing loss of blood flow and ischemia distal to the occlusion. Patients with side branch occlusion (SBO) were predicted to have more ischemia than those without. Patients were assigned to the SBO subset if their cardiologist indicated they had significant SBO.

Study results showed significantly higher ischemia test values immediately after and 6 hours after PTCA in patients with SBO. The following data includes patients in all study subsets. The number of patients varies because investigators were not always able to obtain blood samples at all four draw times.

| % CHANGE FROM BASELINE | WITH SBO | | | WITHOUT SBO | | | T-TEST |
|---|---|---|---|---|---|---|---|
| | N | MEAN | SD | N | MEAN | SD | P |
| Immed Post PTCA | 8 | .228 | .144 | 51 | .076 | .102 | .0005 |
| 6 hrs Post PTCA | 8 | .150 | .156 | 45 | .033 | .149 | .0480 |
| 24 hrs Post PTCA | 8 | .168 | .222 | 33 | .013 | .098 | .1500 |

Example 10

Assessment of the Patency of in-situ Coronary Stent

Coronary stents may be inserted during angioplasty and left in place on a permanent basis in order to hold open the artery and thus improve blood flow to the heart muscle and relieve angina symptoms. Stent insertion consists of the insertion of a wire mesh tube (a stent) to prop open an artery that has recently been cleared using angioplasty. The stent is collapsed to a small diameter, placed over an angioplasty balloon catheter and moved into the area of the blockage. When the balloon is inflated, the stent expands, locks in place and forms a rigid support to hold the artery open.

Stent use has increased significantly in just the past year, and is now used in the vast majority of patients, sometimes as an alternative to coronary artery bypass surgery. A stent may be used as an alternative or in combination with angioplasty. Certain features of the artery blockage make it suitable for using a stent, such as the size of the artery and location of the blockage. It is usually reserved for lesions that do not respond to angioplasty alone due to the reclosure of the expanded artery.

In certain selected patients, stents have been shown to reduce the renarrowing that occurs in 30-40 percent of patients following balloon angioplasty or other procedures using catheters. Stents are also useful to restore normal blood flow and keep an artery open if it has been torn or injured by the balloon catheter.

However, reclosure (referred to as restenosis) is a common problem with the stent procedure. In recent years doctors have used stents covered with drugs that interfere with changes in the blood vessel that encourage reclosure. These new stents have shown some promise for improving the long-term success of this procedure. Additionally, after a stent procedure has been done, patients are often placed on one or more blood thinning agents such as aspirin, Ticlopidine and/or Coumadin in order to prevent or prolong reclosure. Whereas aspirin may be used indefinitely; the other two drugs are used only for four to six weeks.

The present invention provides a mechanism for monitoring the functioning and patency of an in silt stent.

Stent patency was tested in the same study and same patient group in which post-myocardial infarction patients were studied (see Example 9). The study results showed significantly lower ischemia test values immediately after and 6 hours after PTCA for those patients with stents. The following data includes patients in the NonAMI subset only. The number of patients varies because investigators were not always able to obtain blood samples at all four draw times.

| % CHANGE FROM BASELINE | WITH STENT | | | WITHOUT STENT | | | T-TEST |
|---|---|---|---|---|---|---|---|
| | N | MEAN | SD | N | MEAN | SD | P |
| Immed Post PTCA | 37 | .089 | .105 | 4 | .210 | .117 | .0373 |
| 6 hrs Post PTCA | 36 | .009 | .139 | 3 | .243 | .153 | .0087 |
| 24 hrs Post PTCA | 26 | .022 | .080 | 1 | .071 | NA | NA |

Example 11

Diagnosis and Assessment of Arrhythmic/Dysrhythmic Patients

The present invention provides a rapid method for assessing arrhythmias and diagnosing and measuring dysrhythmias.

Rapid assessment and treatment of arrhythmias is key to a successful outcome: if treated in time, ventricular tachycardia and ventricular fibrillation can be converted into normal rhythm by administration of an electrical shock; alternatively, rapid heart beating can be controlled with medications which identify and destroy the focus of the rhythm disturbances. If an arrhythmia is not promptly diagnosed and treated, a stroke may be the likely result. Arrhythmia prevents the heart from fully pumping blood out of the heart chambers; the undisgorged blood remaining in the heart chamber will pool and clot. If a piece of the blood clot in the atria becomes lodged in an artery in the brain, a stroke results. About 15 percent of strokes occur in people with atrial fibrillation.

Traditionally, electrocardiography, also called ECG or EKG, is used to diagnosis the occurrence of an arrhythmia. (Also utilized are the "12 lead EKG" and signal-averaged electrocardiogram (S.A.E.C.G.), the S.A.E.C.G. to identify people who have the potential to experience a dangerous ventricular arrhythmia and the "12 lead EKG" primarily in people undergoing arrhythmias.) However, all of the electrocardiographic tests yield frequent false positive and false negative results. The present invention provides a method for supplementing all of the aforementioned electrocardiographic tests in order to reduce, if not avoid entirely, the frequency of false positive and false negative diagnoses.

Other diagnostics techniques typically used are invasive and thus possess greater risk. For instance, transesophageal echocardiography (T.E.E.) is an imaging procedure, in which a tube with a transducer on the end of it is passed down a person's throat and into the esophagus; images from TEE can give very clear pictures of the heart and its structures. Cardiac catheterization is another invasive procedure which allows for measurement and viewing of the pumping ability of the heart muscle, the heart valves and the coronary arteries. The shortcoming of these procedures, however, lies in their invasive nature.

The present invention provides a non-invasive method for diagnosis and measurement of dysrhythmias which can be used in lieu of, or in supplementation of, the aforementioned invasive procedures.

Patients with dysrhythmias undergoing PTCA were predicted to have more ischemia than those without. (Dysrhythmia is cited in the medical literature as a good indicator of ischemia.) In the 63 patient study detailed in Examples 9 and 10, patients were additionally assigned to a dysrhythmia subset if their medical record showed significant dysrhythmia during PTCA. Study results showed significantly higher ischemia test values immediately after and 6 hours after PTCA in patients with significant dysrhythmias. The following data includes patients in all study subsets. The number of patients varies because investigators were not always able to obtain blood samples at all four draw times.

| % CHANGE FROM BASELINE | WITH DYSRHYTHMIA | | | W/O DYSRHYTHMIA | | | T-TEST |
|---|---|---|---|---|---|---|---|
| | N | MEAN | SD | N | MEAN | SD | P |
| Immed Post PTCA | 5 | .265 | .151 | 57 | .079 | .103 | .0004 |
| 6 hrs Post PTCA | 5 | .204 | .175 | 51 | .035 | .141 | .0150 |
| 24 hrs Post PTCA | 5 | .144 | .236 | 37 | .017 | .107 | .3000 |

Examples 12-23

Use of N-terminus Peptide Probe in the Evaluation of Ischemia

Under the present invention, an amino acid sequence found within the N-terminus sequence of albumin is required for cobalt binding. This sequence has been identified as Asp-Ala-His-Lys (abbreviated "DAHK", residues 1-4 of SEQ. ID. NO. 1). The binding characteristics of this tetrapeptide have been extensively studied and it has been determined that this tetrapeptide may be used to detect the presence of ischemia.

Specifically, a biological sample containing albumin is contacted with $CoCl_2.6H_2O$. Some of this cobalt will bind to albumin. The remaining free cobalt is then reacted with a known amount of D-A-H-K•R (residues 1-4 of SEQ. ID. NO. 1) added to the biological sample, wherein R is any chemical group or enzyme, including no group at all or a fluorescent group, capable of being detected. Because D-A-H-K•R (residues 1-4 of SEQ. ID. NO. 1) has a great affinity to cobalt (association constant about $10^{15}$) the free cobalt will attach to it. The D-A-H-K•R (residues 1-4 of SEQ. ID. NO. 1) differs from Co-D-A-H-K•R (residues 1-4 of SEQ. ID. NO. 1) spectroscopically. One distinction is that Co-D-A-H-K•R (residues 1-4 of SEQ. ID. NO. 1) has an extinction coefficient that is 1.5 to 2 times the peptide alone. This phenomenon can be used to determine that the peptide has bound to the cobalt (an increase in absorption at about 214 nm using HPLC or other methods).

Example 12

To a 0.2 ml sample of blood or plasma was added 50 μL 0.1% $CoCl_2$. The mixture was incubated for 5 to 10 minutes. Thereafter, 50 μL of 1 mg/ml of D-A-H-K•R was added to the sample. (R was a polymer or other substance having chemical and physical characteristics that changed when the cobalt binds to the peptide—causing a small current change or any other change that was detected.) The sample was then centrifuged (Centricon 10 or 3) for 5 minutes, followed by HPLC analysis of the filtrate using a ultrahydrogel 120, 5μ column at 60° C.; isocratic run, mobile phase acetonitrile: ammonium acetate buffer 3OmM pH 8.0, 2:98; at 1 ml/minute and U.V. detection at 214 nm. The peptide peak appeared at ~5.88 minutes.

The same procedure was run with a peptide control (no cobalt). The difference in peak size between test (with cobalt) and control (no cobalt) was proportional to the amount of free cobalt and hence ischemia.

The following preliminary experiments illustrate the properties and critical characteristics of the peptide probe.

Example 13

Measurement of Cobalt Binding to HSA and Octapeptide Using Cold Cobalt Binding Assay OBJECTIVE: To investigate cobalt binding to the octapeptide and human serum albumin using cold cobalt binding assay.

EXPERIMENTAL: Octapeptide synthesized at the Inorganic Chemistry Department (BAM 1, Pat Ingrey, Cambridge): $NH_2$-Asp-Ala-His$^+$-Lys$^+$-Ser-Glu-Val-Ala-$CONH_2$, residues 1-8 of SEQ. ID. NO. 1) Molecular weight: 855.4 Da.

SOLUTIONS: $CoCl_2$ 0.1% (w/v)=4.2 mM; HSA 3% (w/v) (in 75 mM HEPES pH 7.4)=0.45 mM; Octapeptide 0.965 mM (in 75 mM HEPES pH 7.4); HEPES 75 mM pH 7.4; DTT 0.15% (w/v); NaCl 0.85% (w/v).

METHOD: Fifty μL 0.1% $CoCl_2$ was added to tubes each containing 200 μL of 75 mM HEPES pH 7.4 or 0.45 mM HSA in HEPES or 0.965 mM Peptide in HEPES; the tubes were allowed to stand at room temperature for 10 minutes; 50 μL DTT 0.15% was added to one tube (test tube) and distilled $H_2O$ to the other (control tube); the tubes were maintained for 2 minutes at room temperature; 1 ml NaCl 0.85% was then added; the absorbance at A470 nm of the test tube versus the blank was measured.

RESULTS:

| ID | A470 nm | | mean A470 | % bound |
|---|---|---|---|---|
| 75 mM HEPES pH 7.4 | 1.087 | 1.083 | 1.085 | 0.0 |
| 0.45 mM HSA in HEPES pH 7.4 | 0.668 | 0.643 | 0.656 | 39.5 |
| 0.965 mM Peptide in HEPES pH 7.4 | 0.638 | 0.655 | 0.647 | 40.4 |

CONCLUSIONS: Under the conditions used for the binding measurements, this experiment showed that: 1. Cobalt binds to the "octapeptide" (N-Asp-Ala-His$^+$-Lys$^+$-Ser-Glu-Val-Ala, residues 1-8 of SEQ. ID. NO. 1); 2. However, the octapeptide (0.965 mM) binds cobalt with a stoichiometry of 1:2.3.

Example 14

Mass Spectrometry of Octapeptide After the Addition of Cobalt

OBJECTIVE: To investigate whether mass spectral study would provide molecular weight information for the octapeptide and its corresponding cobalt complex.

SOLUTIONS: Ammonium acetate 20 mM-pH 7.4 (with dilute ammonia solution); $CoCl_2$ 20 µM (in HPLC grade $H_2O$); Octapeptide 9.5 µM (in HPLC grade $H_2O$).

METHOD: 20 µM $CoCl_2$ (100 µl) was added to 9.5 µM octapeptide (100 µl) and mass spectrometry carried out.

RESULTS: The main molecular ion peak was observed at 855.4 Da, with minor peaks at 877.4 and 893.4 Da probably as a result of sodium and potassium cluster ions. After the addition of cobalt, an extra molecular ion peak was observed at 912.3 Da.

CONCLUSIONS: Octapeptide showed a molecular ion at 855 Da consistent with the expected molecular weight of the peptide moiety. Octapeptide plus cobalt complex showed a molecular ion at 912 Da suggesting that at least two protons are removed during the complex formation.

Example 15

Spectrophotometric Analysis of the Octapeptide and Octapeptide-Cobalt Complex

OBJECTIVE: It is clear from the previous mass spectrometry evidence that cobalt forms a complex with the octapeptide with a concomitant loss of two possible protons. Metal complexes in general show distinct absorption in the UV range and in many cases these complexes show either a hypochromic or a bathochromic shift in the spectra. These shifts can be correlated to provide the energy of binding. It was therefore anticipated that the octapeptide-cobalt complexation would provide such information.

METHOD: The quartz cuvette contained 800 µl octapeptide+200 µl $H_2O$(control) or $CoCl_2$ (complex). Spectra were run from 180 to 800 nm on a single beam spectrophotometer.

CONCLUSIONS: Cobalt and octapeptide individually have peak absorbances at <200 and 225 nm respectively with little overlap. Following addition of a $CoCl_2$ solution to octapeptide (1.1:1) there was no significant shift in the $K_{max}$ (220 nm). The absorption band at this region broadened indicating complex formation, but the result could not be used to determine the binding energy (constant).

Example 16

Mass Spectrometry of Octapeptide After the Addition of Cobalt

OBJECTIVE: To investigate whether mass spectral study would provide molecular weight information for the peptide and its corresponding cobalt complex.

METHOD: 20 or 200 µM $CoCl_2$ (100 µl) was added to 22.9 µM octapeptide (100 µl) to give ratios of cobalt: octapeptide of 1:1.1 and 8.7:1 respectively. Mass spectra for the two samples were carried out as per conditions detailed in the previous experiment.

RESULTS: One major molecular ion peak was observed at 855.4 Da representing the octapeptide alone. After the addition of 20 µM cobalt to the octapeptide, two peaks were observed, a major peak at 855.3 representing octapeptide only plus a minor peak at 912.2 Da representing octapeptide-cobalt complex. Peak ratio of free octapeptide to octapeptide-cobalt complex was 1:0.15. A similar profile was observed following the addition of 200 µM cobalt to the octapeptide. Peak ratio of free octapeptide to octapeptide-cobalt complex was 1:0.9.

CONCLUSIONS: On addition of cobalt (59 Da) to the octapeptide, the molecular ion peak should have occurred at 914 Da. The actual peak occurred at 912 Da, representing the loss of two protons. On addition of increasing concentrations of cobalt the peak ratio of free octapeptide to octapeptide-cobalt complex increased.

Example 17

The Effect of Oxygen on the Binding Capacity of Octapeptide for Cobalt

OBJECTIVE: Previous experiments have highlighted the requirement of oxygen in promoting cobalt binding to HSA. It may be anticipated that similar effects could be observed in the manner of cobalt binding to the octapeptide.

METHOD: Octapeptide-cobalt complex (no oxygen): HPLC grade $H_2O$ was bubbled with 100% helium for 10 minutes prior to use and used to prepare the above solutions. These were further deoxygenated for 10 minutes before adding 200 µM $CoCl_2$ (2 ml) to 22.9 µM octapeptide (2 ml). This mixture was again deoxygenated for 10 minutes prior to analysis by HPLC.

Octapeptide-cobalt complex (with oxygen): HPLC grade $H_2O$ was bubbled with 100% oxygen for 10 minutes prior to use and used to prepare the above solutions. These were further oxygenated for 10 minutes before adding 200 µM $CoCl_2$,(2 ml) to 22. µM octapeptide (2 ml). This mixture was again oxygenated for 10 minutes prior to analysis by HPLC.

HPLC Analysis: Chromatography was carried out on a KS437 styrene/DVB polymer column (4.6 mm×150 mm, pore diameter 100-150 Å, BioDynamics) under isocratic conditions of 2% acetonitrile in 30 mM Ammonium acetate pH 8.0 at a flow rate of 2 ml/min. Peaks were detected at 230 nm. Chromatography gave two distinct peaks at 230 nm, the first peak representing octapeptide-cobalt complex and the second peak representing free octapeptide. Octapeptide-$Co^{2+}$ complex formed in the presence of oxygen gave a higher ratio of complex over free peptide, as indicated by the first peak being the larger of the two. Octapeptide-Co2$^+$ complex formed in the absence of oxygen again gave two peaks but the second peak was now the larger of the two, indicating less complex formation.

Example 18

The Effect of pH on the Octapeptide

OBJECTIVE: To optimize chromatography conditions for analysis of octapeptide by HPLC.

METHOD: The octapeptide was analyzed by HPLC using a KS437 styrene/DVB Polymer column (4.6 mm×150 mm, pore diameter 100-150 Å, BioDynamics) under isocratic conditions of 2% acetonitrile in 30 mM Ammonium acetate at pH 6.2, 7.5 and 8.0 at a flow rate of 2 ml/min. Peaks were detected at 230 nm.

RESULTS: At pH 6.2, the octapeptide eluted after 1.6 min. At pH 8.0 the retention time had increased to 2.1 min. When the octapeptide was run at pH 7.5, two peaks were observed at 1.6 and 2.1 min.

CONCLUSIONS: The octapeptide exists in two forms depending on pH. The protonated form elutes at pH 6.2, and the deprotonated form at pH 8.0.

Example 19

The Effect of pH on the Binding of Cobalt to the Octapeptide

OBJECTIVE: It was reported that the peptide peak 'shifted' when a solution of cobalt chloride was added to the octapeptide. It was decided to investigate this phenomenon fully as this would provide a direct tool for the determination of several parameters of cobalt binding to the octapeptide.

METHOD: 200 mM $CoCl_2$ (30 µl) was added to 2.3 mM octapeptide (270 µl), incubated at room temperature for 10 minutes and analyzed by HPLC. HPLC analysis: The octapeptide-cobalt complex was analyzed by HPLC using a KS437 styrene/DVB polymer column (4.6 mm×150 mm, pore diameter 100-150 Å, BioDynamics) under isocratic conditions of 2% acetonitrile in 30 mM Ammonium acetate at pH 6.2 and 8.0 at a flow rate of 2 ml/min. Peaks were detected at 230 nm.

RESULTS: At pH 6.2, a single peak eluted after 1.6 min in the presence and absence of cobalt. At pH 8.0 however a single peak eluted after 1.2 min in the presence of cobalt and at 2.1 min in the absence of cobalt.

CONCLUSIONS: The octapeptide exists in two forms depending on pH. The protonated form that elutes at pH 6.2 is unable to bind cobalt and therefore its elution profile is unchanged. In contrast, the deprotonated form which exists at pH 8.0 is able to bind cobalt, resulting in an increased UV absorption and a decreased retention time, 1.2 min as opposed to 2.1 min for the free octapeptide.

Example 20

The Titration of Octapeptide with Increasing Concentrations of Cobalt

OBJECTIVE: To determine whether increasing concentrations of cobalt resulted in a corresponding increase in octapeptide-cobalt complex formation.

METHOD: Octapeptide was used at a final concentration of 2.1 mM throughout, with increasing concentrations of $CoCl_2$, as shown in the Table below:

| [$CoCl_2$] (mM) | Vol $CoCl_2$ added (µl) | [Octapeptide] (mM) | Vol octapeptide added (µl) | Ratio of octapeptide: $CoCl_2$ |
|---|---|---|---|---|
| 0 | 0 | 2.3 | 27 | 1:0 |
| 1 | 3 | 2.3 | 27 | 21:1 |
| 1.25 | 3 | 2.3 | 27 | 16.8:1 |
| 2.25 | 3 | 2.3 | 27 | 9.3:1 |
| 4.5 | 3 | 2.3 | 27 | 4.7:1 |
| 10 | 3 | 2.3 | 27 | 2.1:1 |
| 18 | 3 | 2.3 | 27 | 1.2:1 |
| 36 | 3 | 2.3 | 27 | 1:1.7 |
| 72 | 3 | 2.3 | 27 | 1:3.4 |
| 200 | 3 | 2.3 | 27 | 1:9.5 |

HPLC analysis: The octapeptide-cobalt complex was analyzed by HPLC using a KS437 styrene/DVB polymer column (4.6 mm×150 mm, pore diameter 100-150 Å, BioDynamics) under isocratic conditions of 2% acetonitrile in 30 mM Ammonium acetate at pH 8.0 at a flow rate of 2 ml/min. Peaks were detected at 230 nm.

RESULTS: Mean % Peak Height:

| Final [$CoCl_2$] (mM) | Peak 1 (Octapeptide- Co complex) | Peak 2 (unknown) | Peak 3 (Octapeptide) |
|---|---|---|---|
| 0 | — | 3.72 | 96.28 |
| 0.1 | 7.44 | 7.08 | 85.49 |
| 0.125 | 9.79 | 7.55 | 82.66 |
| 0.225 | 15.65 | 15.66 | 68.52 |
| 0.45 | 25.36 | 19.67 | 54.98 |
| 1.0 | 58.66 | — | 50.42 |
| 1.8 | 61.19 | 14.97 | 23.85 |
| 3.6 | 69.55 | 13.69 | 16.76 |
| 7.2 | 71.49 | 14.47 | 14.05 |
| 20.0 | 82.17 | 10.27 | 7.56 |

From the table immediately preceding, a plot of Log cobalt concentration versus % peak height for peak 3 was produced using Prism software. The 50% binding constant as deduced from the exponential graph had a value of 0.6461 mM.

CONCLUSIONS: For 50% binding, 0.6461 mM $Co^{2+}$ binds to 2.1 mM octapeptide. Therefore for 100% binding, 1.2922 mM $Co^{2+}$ binds to 2.1 mM octapeptide. The stoichiometry of cobalt binding to octapeptide is 0.615 cobalt to 1 octapeptide.

Example 21

Liquid Chromatography-Mass Spectrometry of Octapeptide After the Addition of Cobalt OBJECTIVE: To investigate whether mass spectral study would provide molecular weight information for the peptide and its corresponding cobalt complex.

METHOD: 200 mM $CoCl_2$ or $H_2O$ (3 µl) was added to 2.3 mM octapeptide (27 µl) and incubated at room temperature for 10 minutes. LC-MS analysis: Liquid chromatography was performed using a KS437 styrene/DVB polymer column (4.6 mm×150 mm, pore diameter 100-150 Å, BioDynamics) under isocratic conditions of 2% acetonitrile in 30 mM Ammonium acetate at pH 8,0 at a flow rate of 0.5 ml/min. Peaks were detected at 230 nm, and analyzed by on line mass spectrometry.

RESULTS: In the control sample, two molecular ion peaks were observed at 855.2 Da, representing the octapeptide alone, and at 877.2 Da, representing an octapeptide-sodium cluster. After the addition of 200 mM cobalt, one major peak was observed at 911.1 Da.

CONCLUSIONS: On addition of cobalt (59 Da) to the octapeptide, the molecular ion peak should occur at 914 Da. The actual peak occurs at 911 Da, representing the loss of protons.

Example 22

Endprotease Lys-C Digest of Octapeptide and its Subsequent Incubation with Cobalt OBJECTIVE: Previous experiments confirm that $CoCl_2$ forms a stable complex with the octapeptide. In order to elucidate the site of attachment, the octapeptide was cleaved stereoselectively with the endoprotease Lys-C. The resultant tetrapeptides upon incubation with $CoCl_2$ would allow elucidation of the probable binding site.

METHOD: Octapeptide 1.97 mg/ml (250 μl) was incubated with the endoprotease Lys-C 100 μg/ml (50 μl) at a substrate:enzyme ratio of 100:1 (w/w) in 8.3 mM Tricine, 1.6 mM EDTA pH 8.0 at 37° C. for 24 h. After digestion, 27 μl of the product was incubated with 200 mM $CoCl_2$ (3 μl) at 20° C. for 10 minutes prior to analysis by HPLC. HPLC Analysis: The products from the Lys-C digest were analyzed by HPLC using an amino column (4.6 mm×250 mm, pore diameter 100 Å, BioDynamics-73) under isocratic conditions of 30 mM Ammonium acetate at pH 8.0 at a flow rate of 1.5 ml/min. Peaks were detected at 230 nm.

RESULTS: When the digested Lys-C products were run on HPLC, two peaks were observed at 2.6 and 8.9 min, designated tetrapeptides 1 and 2 respectively. Similarly after addition of cobalt to the digested products two peaks were again observed. However, tetrapeptide 1 exhibited an increased UV absorption and decreased retention time, eluting at 1.7 min as opposed to 2.6 min.

CONCLUSIONS: The octapeptide was digested at the C terminus of the lysine residue by the endoprotease yielding two tetrapeptides. On addition of cobalt to the endoprotease digested octapeptide, a single tetrapeptide-cobalt complex was formed with tetrapeptide 1. There appeared to be no effect on tetrapeptide 2.

Example 23

Mass Spectrometry Analysis of the Tetrapeptide 1-Cobalt Complex

OBJECTIVE: To determine the identity of tetrapeptide 1.

EXPERIMENTAL: Tetrapeptides 1 and 2 were fractionated by HPLC and collected. $CoCl_2$ 1.2 mM (3 μl) was added to tetrapeptide 1 (27 μl) and incubated at room temperature for 10 minutes. Samples were subsequently run on MS as described previously.

RESULTS: Tetrapeptide 1 gave two molecular ion peaks at 470.1 and 477.1 Da. Tetrapeptide 2 gave a single peak at 404.0 Da. Tetrapeptide 1-cobalt complex gave two peaks at 477.1 and 526 Da.

CONCLUSIONS: Tetrapeptide 1 is determined to be Asp-Ala-His-Lys (residues 1-4 of SEQ. ID. NO. 1) with a molecular weight of 469 Da. Tetrapeptide 2 is determined to be Ser-Glu-Val-Ala (404 Da, residues 5-8 of SEQ. ID. NO. 1). Cobalt binds to Asp-Ala-His-Lys (residues 1-4 of SEQ. ID. NO. 1) forming a complex of 526 Da with a loss of 3 protons. The molecular ion peak observed at 477.1 Da is a contaminant from the Lys-C preparation.

Example 24

Manufacture of Albumin/Metal Calibrator Solutions

Human albumin solutions of 35 mg/ml containing cobalt of molar ratios of 0, 0.4, 0.625, 0.83, 1.25 and 2.5 to 1, cobalt:albumin, were made according to the following protocol.

An albumin solution of 35 mg/ml, Solution A, was made by initially dissolving 40 g solid human albumin (Fraction V, Sigma Chemical Co., St. Louis) in 900 ml 50 mM Tris-Cl, pH 7.2, 0.15 NaCl, and assessing albumin concentration with bromo cresol green (BCG) assay (Sigma Chemical Co.). Additional buffer was added to produce an albumin concentration of 35 mg/ml. This solution was allowed to sit at 4° C. for at least 24 hours prior to use.

To 500 ml of Solution A, 1.27 ml 0.32M $Co(OAc)_2.6H_2O$ (160 mg Co salt/2 ml $H_2O$) (Sigma Chemical Co.) was added drop-wise with gentle swirling to produce a cobalt:albumin molar ratio of 1.25:1, Solution B. This solution was allowed to sit at room temperature for one hour prior to storage at 4° C. until use.

Different volumes of Solutions A and B were mixed to produce additional calibrator solutions:

| Cobalt:Albumin ratio | Solution A, ml | Solution B, ml |
| --- | --- | --- |
| 0 | 200 | 0 |
| 0.4 | 133 | 67 |
| 0.625 | 100 | 100 |
| 0.83 | 67 | 133 |
| 1.25 | 0 | 200 |

To make a cobalt:albumin calibrator solution of 2.5:1, 0.94 ml of 0.32M $Co(OAc)_2$ was added to 229 ml of Solution A. This solution was permitted to sit at room temperature for one hour and then stored at 4° C. until use.

Example 25

Quality Control Characterization of Calibrator Solutions

To obtain a cobalt:albumin ratio, one ml aliquots of each of the five calibrator solutions (each of which had been in storage for 24 hours prior to testing) was placed individually in dialysis bags and dialyzed against 400 ml 50 mM Tris-Cl, pH 7.2, 0.15M NaCl, with three changes of buffer at room temperature. Three to 5 μl of the dialyzates were withdrawn and analyzed for albumin using 1 ml of the BCG dye from Sigma Chemical Co. Absorbance was read at 628 nm after 30 seconds.

Cobalt was assessed by atomic absorption by Galbraith Laboratories, Inc., Knoxville, Tenn.

The cobalt:albumin ratios were found to conform to expected values for all five calibrator solutions.

| Added Cobalt, Co:albumin | At equilibrium, Co:albumin |
| --- | --- |
| 0.4 | 0.16 |
| 0.625 | 0.26 |
| 0.83 | 0.31 |
| 1.25 | 0.46 |
| 2.50 | 0.74 |

These results indicate that the amount of cobalt bound per albumin molecule following dialysis remained proportional to the original metal concentration in the calibrator solution, indicating that the metal-cobalt complex is stable.

Example 26

Generating a Standard Curve Using Calibrator Solutions

Aliquots of 200 µl were withdrawn from each calibrator solution stored at 4° C. into 12×75 mm borosilicate tubes and allowed to equilibrate to room temperature for at least 15 minutes.

A standard solution of 0.8% $CoCl_2.6H_2O$ in $H_2O$ had been made by dissolving 0.4 g solid in 500 ml deionized $H_2O$ in a 500 ml polystyrene bottle; cobalt concentration was confirmed by atomic absorption by Galbraith Laboratories, Inc. Fifty µl of 0.8% $CoCl_2$ solution was added to each calibrator solution and gently mixed.

A 10 mM DTT standard solution had been made by equilibrating the bottle of DTT (DL-dithiothreitol, Sigma Chemical Co.) to room temperature, weighing 12 mg and dissolving same in 8 ml deionized water. The sulfhydryl content of this solution was assessed using Ellman's Reagent, 5,5'-thio-bis (2-nitrobenzoic acid), Sigma Chemical Co. Exactly 10 minutes after addition of $CoCl_2$ solution to the calibrator solutions, 50 µl of the 10 mM DTT solution was added, mixed and allowed to react for 2 minutes. Substitution of DTT with 50 µl 0.9% NaCl was used as the blank. The reaction was quenched by the addition of 1.0 ml 0.9% NaCl. Absorbance at 470 nm on day 1 was read as soon as practicable. Absorbance was read again on days 12, 20 and 23:

| Calibrator Co:albumin | A470 Day 1 | A470 Day 12 | A470 Day 20 | A470 Day 23 |
| --- | --- | --- | --- | --- |
| 0 | 0.26 | 0.26 | 0.23 | 0.27 |
| 0.4 | 0.32 | 0.30 | 0.28 | 0.29 |
| 0.625 | 0.33 | 0.33 | 0.31 | 0.31 |
| 1.25 | 0.39 | 0.40 | 0.37 | 0.37 |
| 2.5 | 0.64 | 0.60 | 0.60 | 0.57 |

Absorbance was plotted against metal concentration originally present in the calibrator solution. The plot was found to be substantially linear over the period studied.

Example 27

Improving the Calibration Range for Albumin/Cobalt Calibrators Standard Curve

Figure 20:
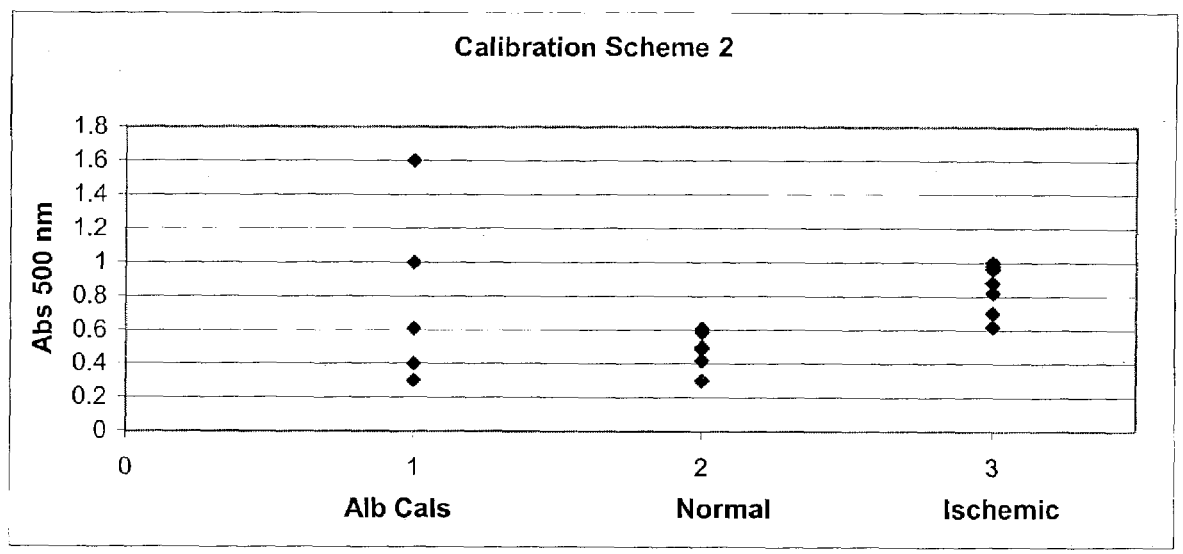
FIG. 20 illustrates the calibrator strategy of using albumin solutions of higher or lower concentrations to increase calibration range to span normal and ischemic absorbance values.

Greater calibration range can be achieved by increasing metal capacity, i.e., by simply adding higher concentrations of albumin. Likewise, lower binding capacity is achieved by further dilution of the albumin solution. An example of this calibrator strategy is shown in FIG. 20.

Example 28

Chelator/Metal Calibrators

Chelators such as EDTA can bind cobalt ions and provide the sequestering function of albumin. This calibration strategy has the advantage of having the same sequence of steps used for measuring controls and patient samples. An EDTA/cobalt standard curve was generated by using dilutions of EDTA in the same method used for the samples: as is done with the patient sample or control, the EDTA calibrators are mixed with a cobalt solution such as ACB Test reagent 1, $CoCl_2$, which is then incubated for several minutes to allow the binding of cobalt to EDTA; DTT is then added and incubated for about two more minutes to allow DTT to complex with non-EDTA sequestered cobalt and form an optically detectable product.

Figure 21:
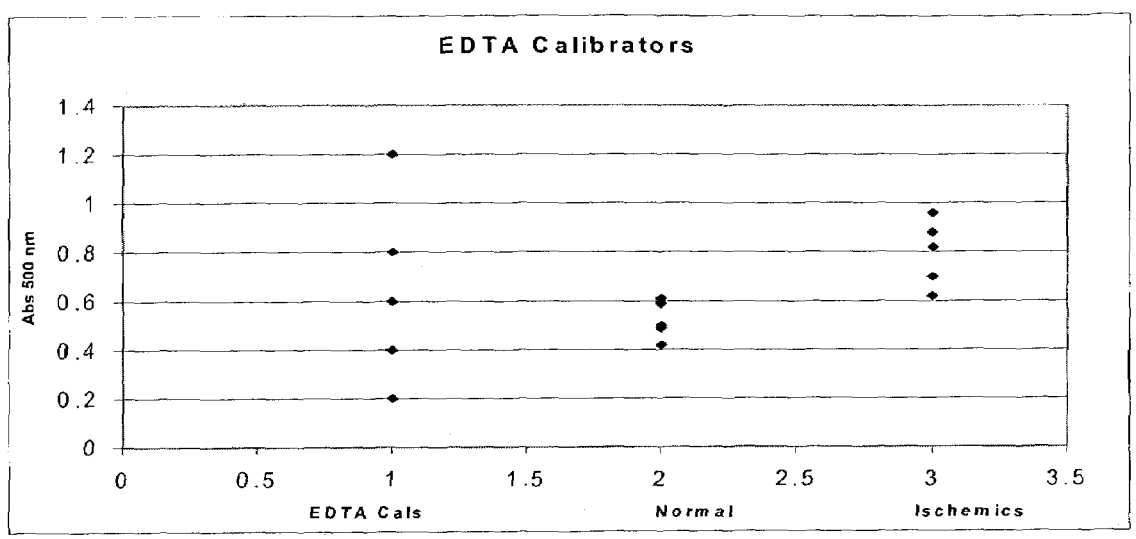
FIG. 21 illustrates that the absorbance range of the EDTA calibrators spans the normal and ischemic patient range.

EDTA calibrators produce a linear curve that successfully spans the ACB assay dynamic range allowing normal and ischemic patients to be measured (FIG. 21). The ability to titrate EDTA levels to adjust calibrators allows for more consistent manufacturing and less lot to lot variability.

Table 2 provides an example of an EDTA calibrator sequence. ACB units of U/mL refers to concentration of ischemia modified albumin and is synonymous with ACB dose.

| Calibrator | EDTA [c] | ACB U/mL | Absorbance 500 nm |
| --- | --- | --- | --- |
| Cal 1 | 1.43 mM | 0 | 0.1029 |
| Cal 2 | 1.22 mM | 34 | 0.2089 |
| Ca 3 | 1.05 mM | 64 | 0.3070 |
| Cal 4 | 0.67 mM | 121 | 0.4795 |
| Cal 5 | 0.00 mM | 212 | 0.7523 |

Figure 22:
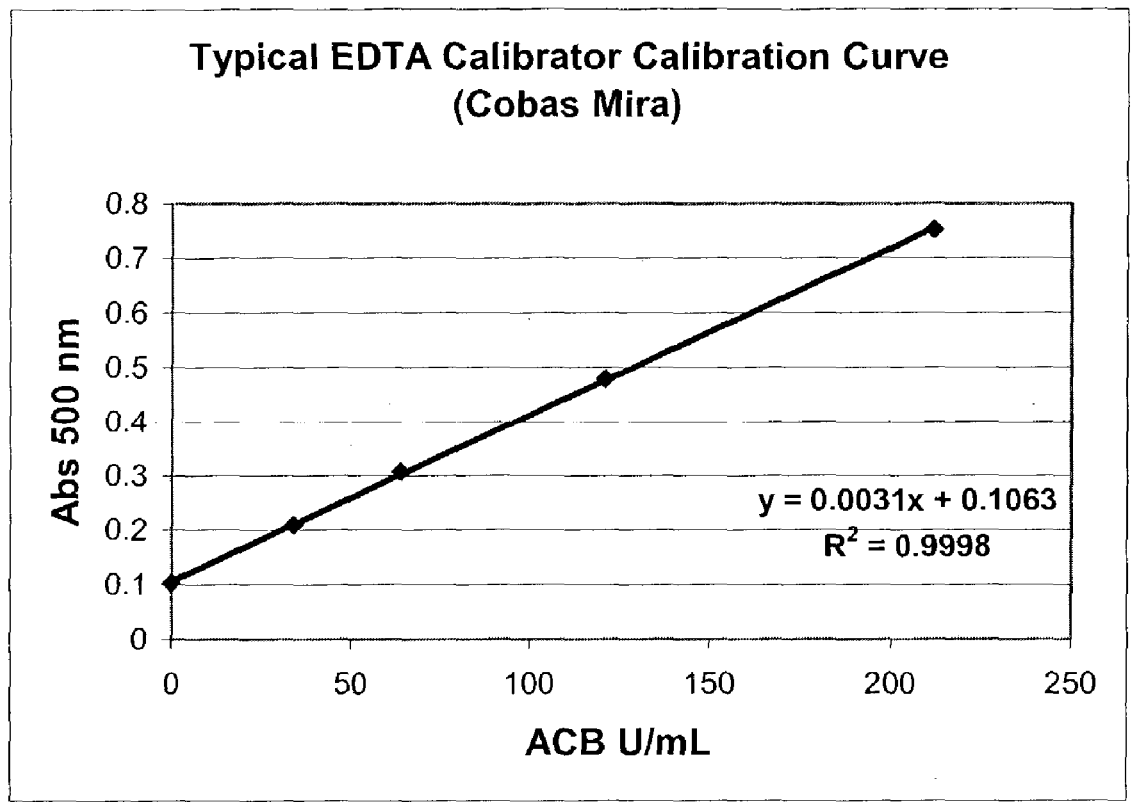
FIG. 22 plots absorbance data reported in Example 28 for the Roche Cobas Mira™ instrument, and shows that absorbance of EDTA calibrators increases as EDTA concentration decreases.

In FIG. 22, absorbance was measured on the Roche Cobas Mira™ clinical chemistry instrument. EDTA calibrators were made using the concentrations listed in Table 2. Linear regression analysis of the calibrator points give and $R^2=0.9998$ with a slope of 0.0031 and a y intercept of 0.1063. Table 2 data is plotted in FIG. 22.

Figure 23:
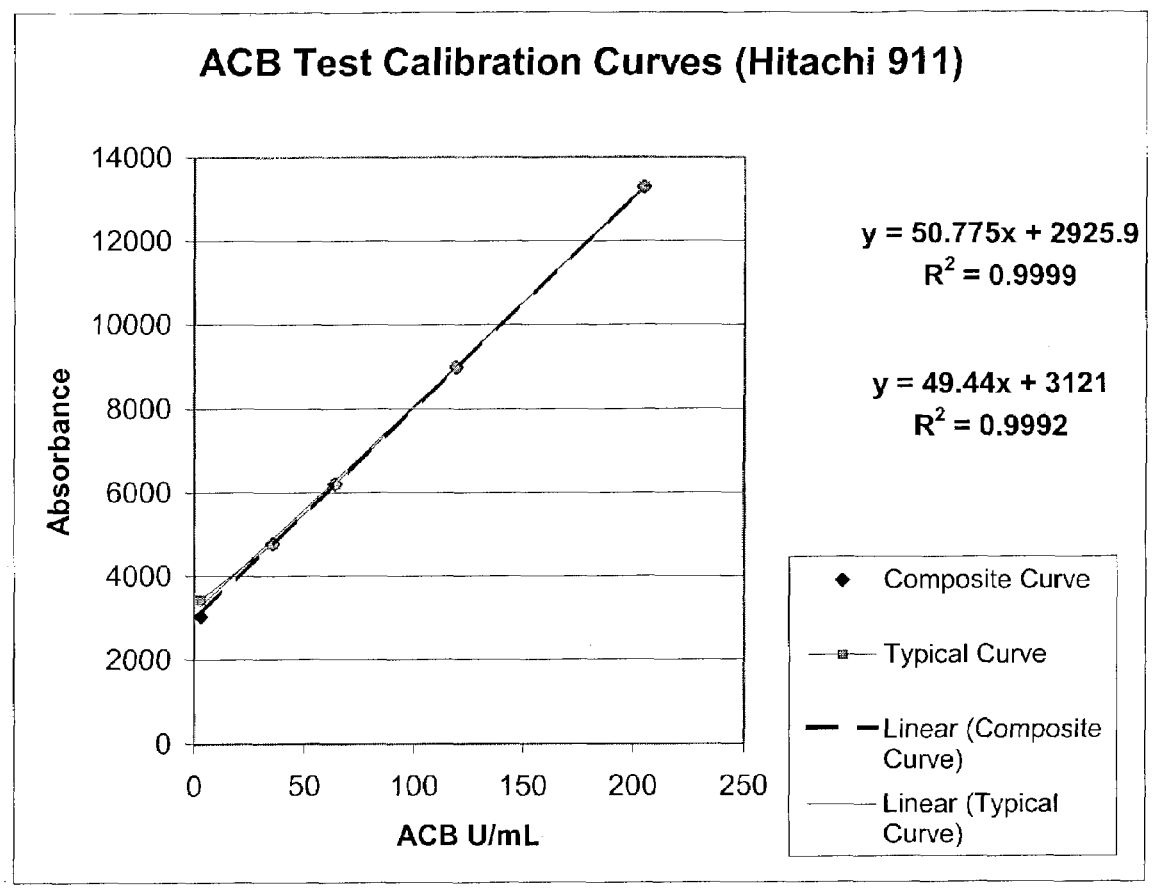
FIG. 23 plots EDTA calibrator absorbance data reported in Example 28 for the Roche Hitachi 911™ instrument.

FIG. 23 shows a typical EDTA calibrator calibration curve run on the Roche Hitachi 911™ clinical chemistry analyzer. EDTA calibrators are the same concentration used on the Cobas Mira instrument. Absorbance values are processed differently on the 911 instrument so typical calibration curve slopes are different. Linear regression analysis of the calibrator points gives an $R^2=0.9999$ with a slope of 50.775 and a y intercept of 2529.9 for a composite EDTA calibrator Hitachi Calibration Curve comprised of 20 calibration curves. Also depicted in the figure is one of the typical Hitachi 911 curves generated using EDTA calibrators. $R^2=0.9992$, slope 49.44, y intercept 3121.

Figure 24:
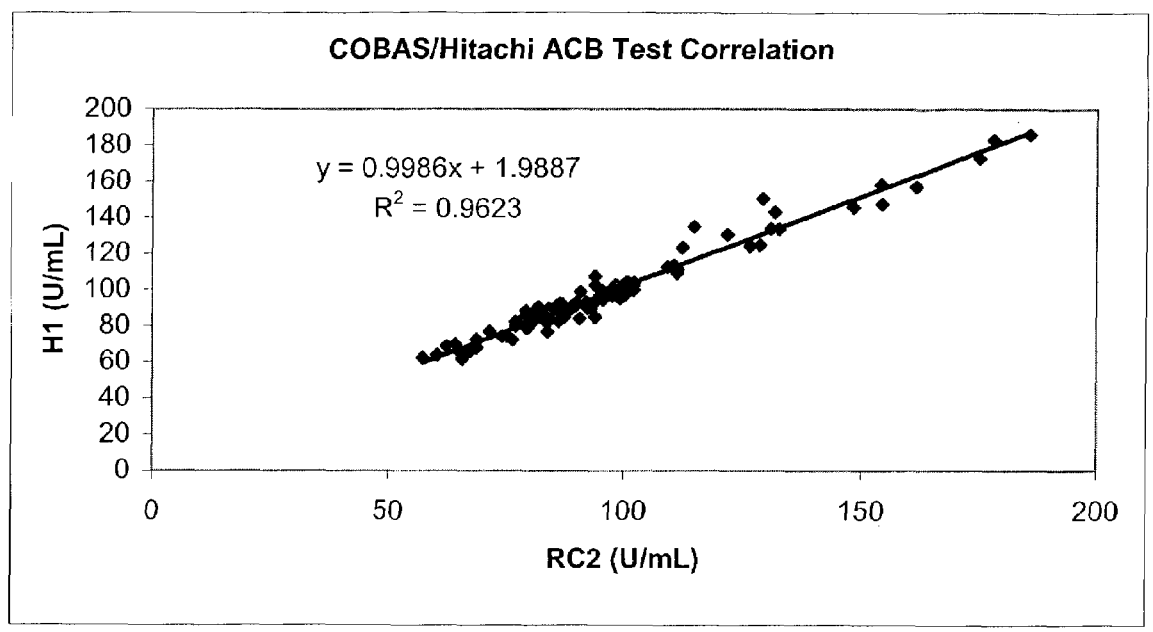
FIG. 24 illustrates the excellent correlation obtained in patient results for 100 samples run on two different instruments. (Roche Cobas Mira and Roche Hitachi 911) using EDTA calibrators.

FIG. 24 demonstrates proof of principle for using ACB Test EDTA calibrators. 100 patient serum samples were measured using the ACB Test run on the Roche Cobas Mira (RC2) instrument and the Roche Hitachi 911 (H1) instrument and a method comparison analysis was made. Calibration curves were generated on each instrument using the same EDTA calibrators. Patient sample reaction absorbance values, as measured on the Cobas Mira (RC2) and Hitachi 911 (H1), were fit off their respective calibration curves to yield an ACB dose value. Results of the method comparison study show excellent correlation ($R^2=0.9623$, slope 0.9986 and y intercept of 1.9887) of patient results measured on two instruments using EDTA calibrators.

Example 29

The NMR Spectra for the Complex of Ni and Albumin N-Terminal Amino Acids

Figure 4:
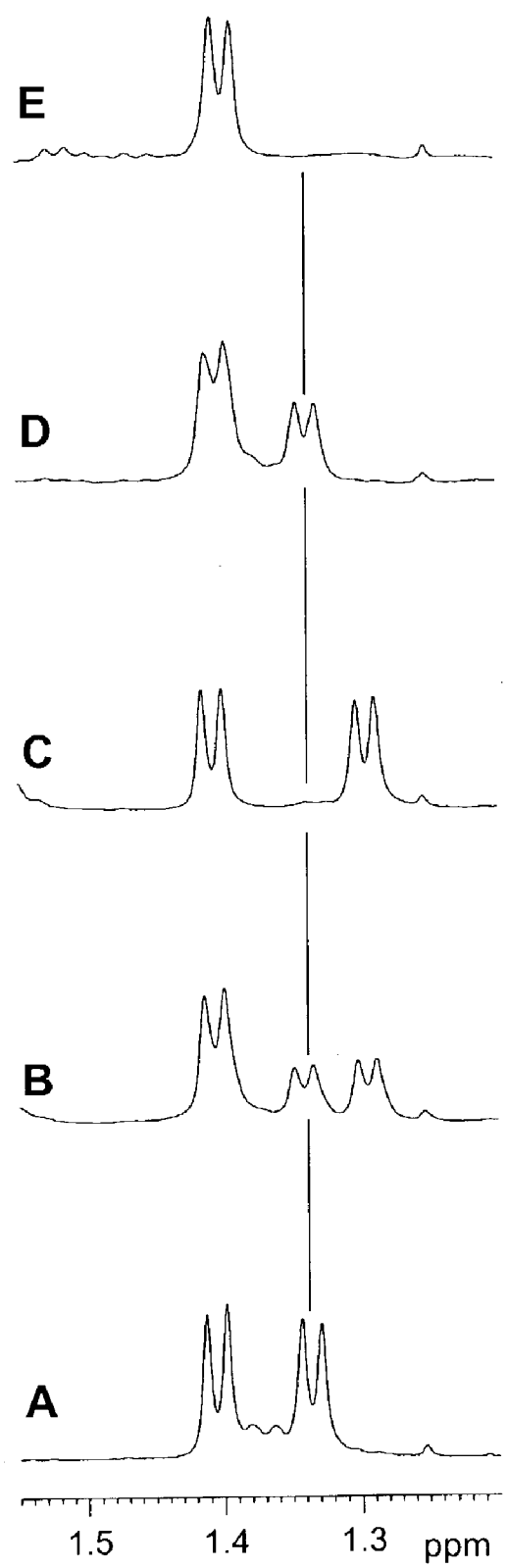
FIG. 4 shows selected regions of the $^1$H-NMR spectra (500 MHz, 10% $D_2O$ in $H_2O$, 300K) showing the Ala resonances (Ala-2 and Ala-8) of the octapeptide (Asp-Ala-His-Lys-Ser-Glu-Val-Ala, residues 1-8 SEQ. ID. NO. 1) (a) free of any metal, with a Lys-4 methylene resonance appearing between the doublets, (b) with 0.5 equiv. of $NiCl_2$ added, (c) with 1.0 equiv. of $NiCl_2$ added, (d) with 0.5 equiv. of $CoCl_2$ added, and (e) with 1.0 equiv. Of $CoCl_2$ added.

Addition of cobalt or nickel chloride to the synthetic albumin N-terminus octapeptide afforded changes in the appearance of the $^1$H-NMR spectrum for the resonances of the first three amino acid residues, with diagnostic changes of the Ala-2 methyl doublet at 1.35 ppm. Titration with $NiCl_2$ gave a sharp diamagnetic $^1$H-NMR spectrum, while addition of $CoCl_2$ induced paramagnetism at the binding site resulting in significant broadening to the resonances associated with the three residues bound around the metal sphere. FIG. 4 shows selected regions of the $^1$H-NMR spectra (500 MHz, 10% $D_2O$ in $H_2O$, 300K) showing the Ala resonances (Ala-2 and Ala-8) of the octapeptide (A) free of any metal, with a Lys-4 methylene resonance appearing between the doublets for Ala2 at about 1.35 ppm and for Ala8 at about 1.4, (B) with 0.5 equiv. of $NiCl_2$ added resulting in a shift of the Ni-bound Ala2 doublet to about 1.3, (C) with 1.0 equiv. of $NiCl_2$ added, (D) with 0.5 equiv. of $CoCl_2$ added, and (e) with 1.0 equiv. of $CoCl_2$ added. In all cases, the appearance and chemical shift of the resonances attributed to Ser-5, Glu-6, Val-7 and Ala-8 did not change significantly after metal addition (up to one equivalent). All these observations were conserved in metal titration experiments with the synthetic tetrapeptide (N-Asp-Ala-His-Lys).

Example 30

P U.V. Spectroscopic Evidence of Co Binding to Albumin Pep-12 Peptides

Figure 5A:
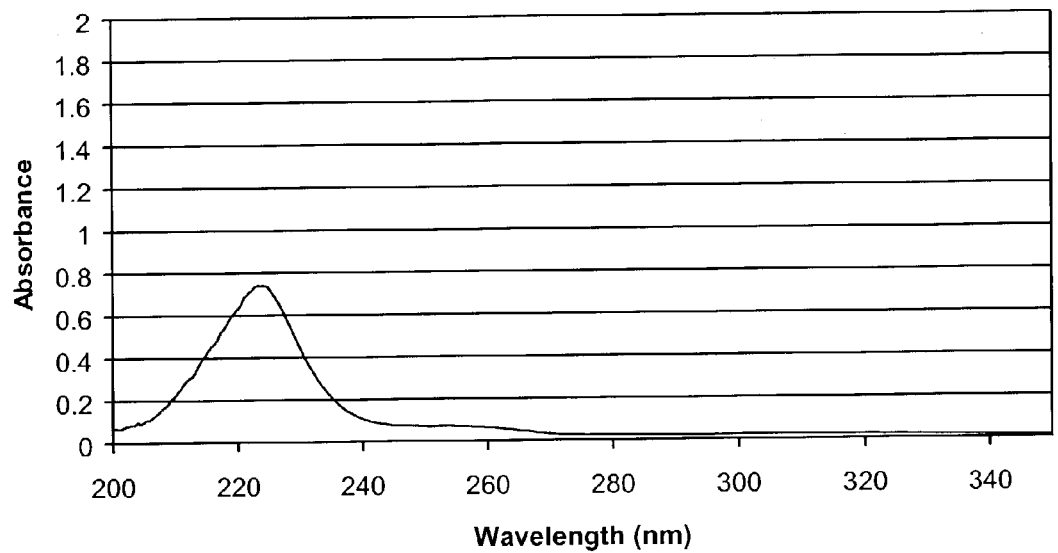
FIGS. 5A and 5B are ultraviolet spectra for non-acetylated Pep-12 (Asp-Ala-His-Lys-Ser-Glu-Val-Ala-His-Arg-Phe-Lys, residues 1-12 of SEQ. ID. NO. 1) and acetylated Pep-12, respectively.
Figure 5B:
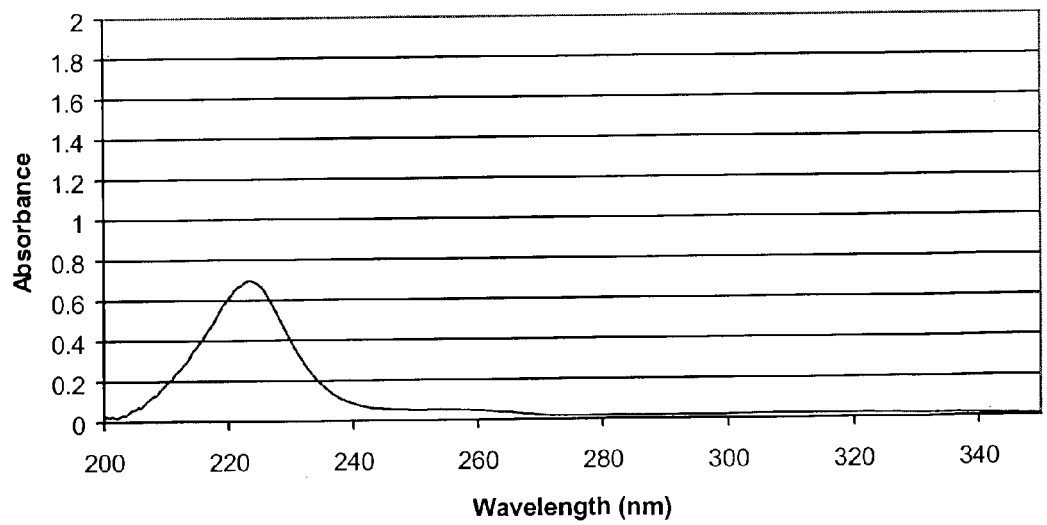
Figure 6A:
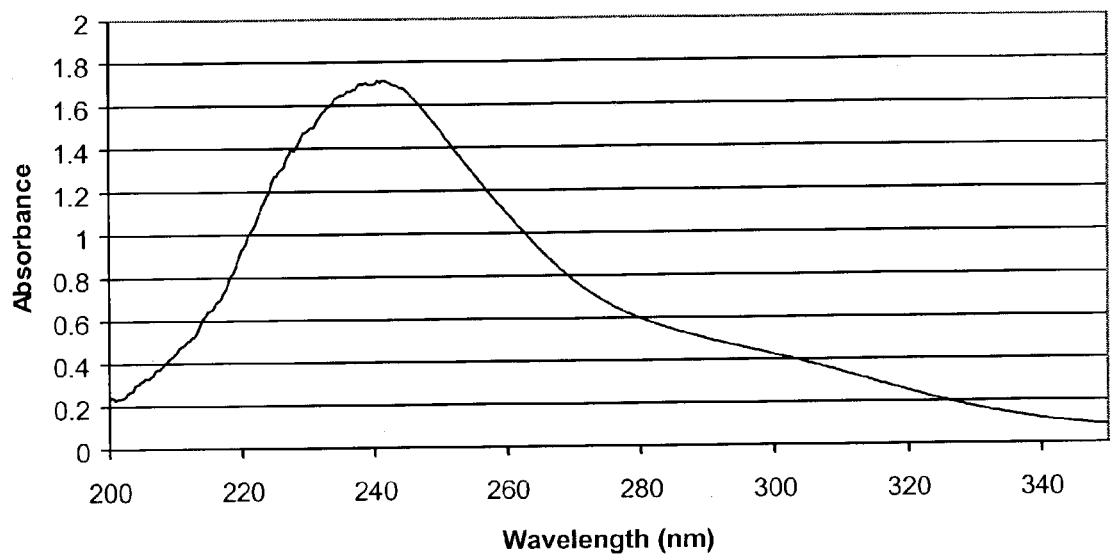
FIGS. 6A and 6B are ultraviolet spectra for non-acetylated Pep-12 and acetylated Pep-12 each with $CoCl_2$, respectively.
Figure 6B:
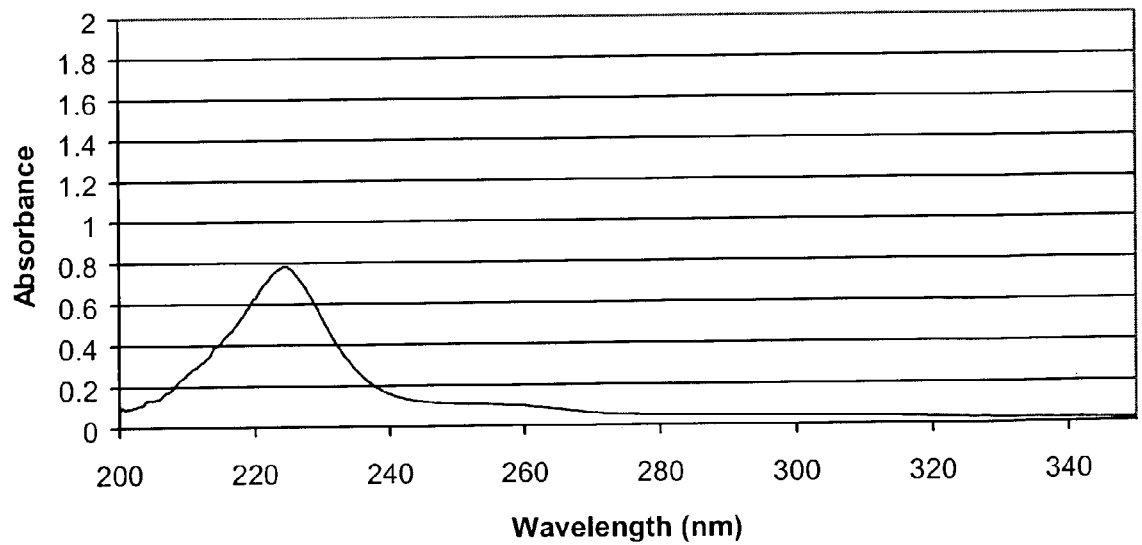

The albumin N-terminal peptide Asp-Ala-His-Lys-Ser-Glu-Val-Ala-His-Arg-Phe-Lys (Pep 12, residues 1-12 SEQ. ID. NO. 1), was synthesized by Quality Controlled Biochemicals, Inc. both in N-acetylated-Asp and free Asp forms, each with free C-terminus. Solutions of 1 mg/ml of the two peptides were made in Tris 50 mM 0.9% NaCl pH 7.2 and analyzed by UV spectroscopy (Ocean Optics SD 2000 and AIS Model DT 1000 as light source). U.V. spectra of Pep-12 and acetylated Pep-12 are set forth in FIGS. 5A and 5B, respectively. Addition of $CoCl_2.6H_2O$ 0.8% (20 µL of the peptide solution) shows a dramatic shift of the λ maximum of the peptide peak as well as a major increase in the extinction coefficient for the nonacetylated Pep-12 (FIG. 6A) and no change in the spectrum of the acetylated Pep-12 (FIG. 6B).

Solutions of Pep-12 and acetylated Pep-12 were made into solutions of 1 mg/ml in Tris 50 mM NaCl 0.9% pH 7.2. Five mixtures of the two starting peptides were made: 100% Pep-12, 75:25 Pep-12:AcPep-12, 50:50 Pep-12:AcPep-12, 25:75 Pep-12:AcPep-12 and 100% AcPep-12.

|  | 1 | 2 | 3 | 4 | 5 |
|---|---|---|---|---|---|
| Pep-12 1 mg/ml | 20 ml | 15 | 10 | 5 | 0 |
| AcPep-12 1 mg/ml | — | 5 | 10 | 15 | 20 |
| +/− $CoCl_2$ 0.08% | 20 | 20 | 20 | 20 | 20 |

Figure 7:
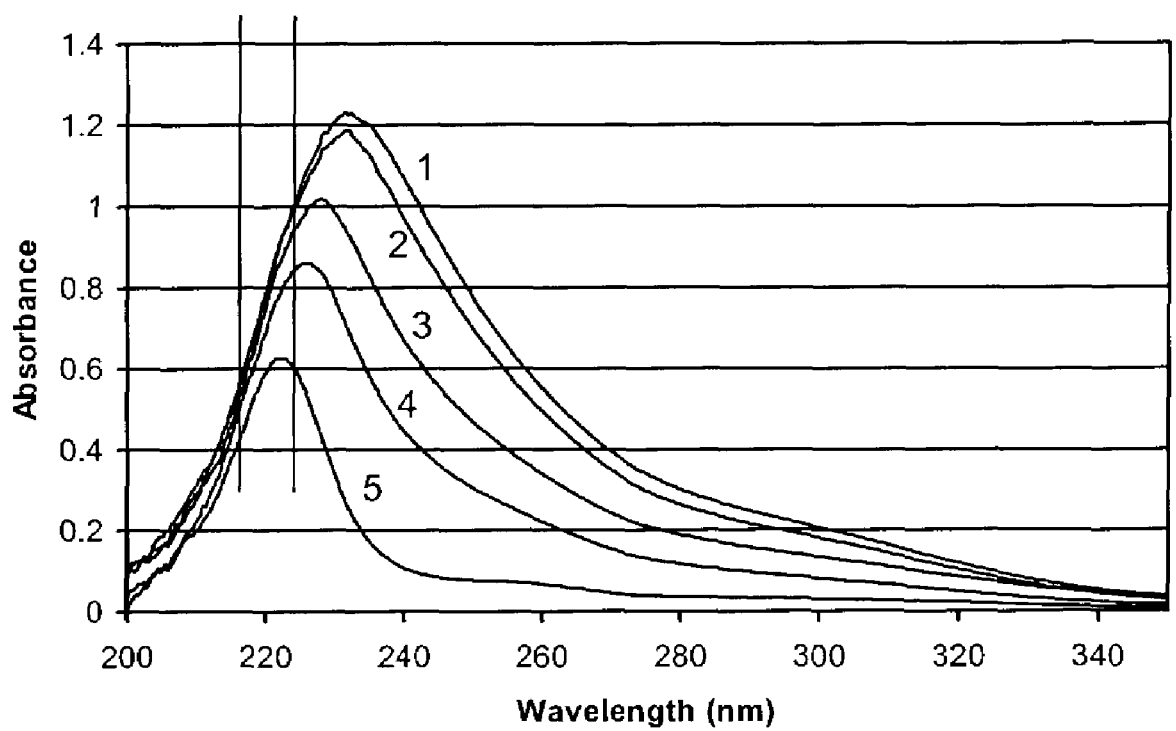
FIG. 7 provides spectral analysis of five solutions of increasing proportions of acetylated Pep-12 to non-acetylated Pep-12 with effect on cobalt binding as reflected by a shift in absorbance from 220 to 230.

Spectral analysis of solutions 1-5 is represented in FIG. 7, from which it can be seen that Pep-12 binds cobalt, AcPep-12 does not bind cobalt. Further, as acetylation increases, cobalt binding goes down.

Example 31

U.V. Spectroscopic Evidence of Co Binding to Albumin Pep-10

Pep-10 was made into 1 mg/ml solutions and incubated with $CoCl_2$ (0.08%). Spectral scans were obtained (data not shown). There was no apparent difference in the absorbance after addition of cobalt, indicating that Pep-10 does not bind cobalt.

Example 31

Copper/Cobalt Competition Binding for Albumin Pep-12

Figure 8A:
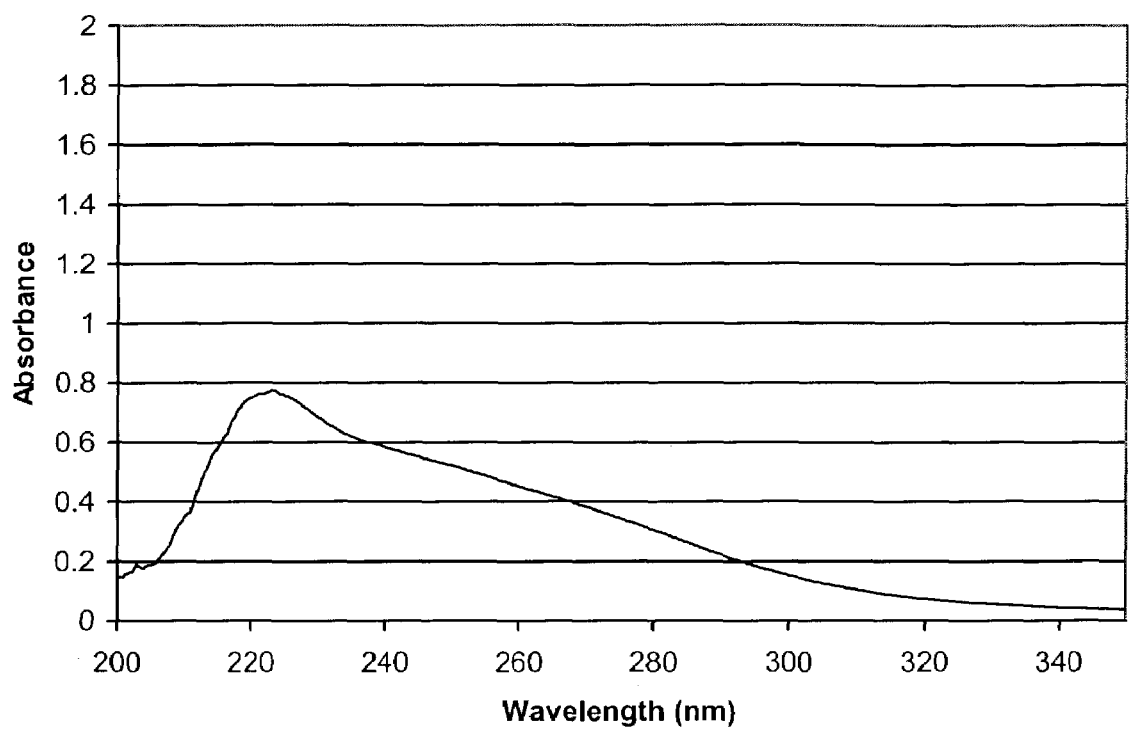
FIGS. 8A and 8B are U.V. spectra of Pep-12 and acetylated Pep-12, respectively, mixed first with $CuCl_2$ and then with $CoCl_2$.
Figure 8B:
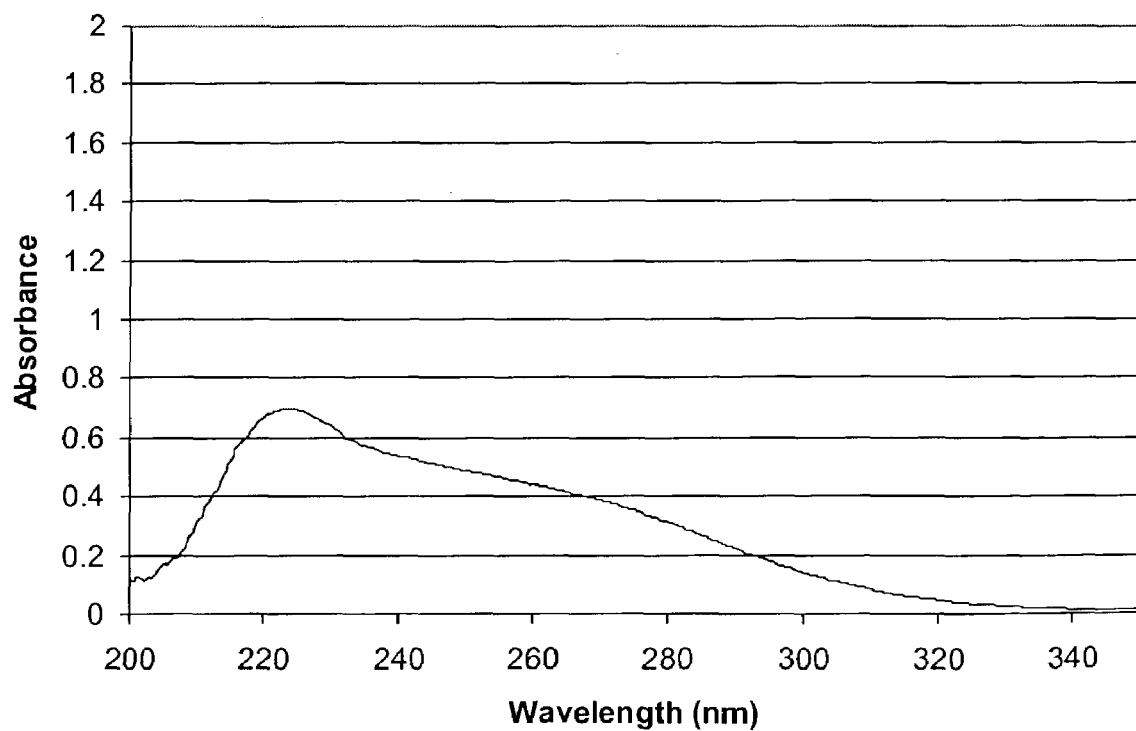

Pep-12 (20 µL of 1 mg/ml or 0.014 µMol) was mixed with 5 µL $CuCl_2$ (0.08% or 0.023 µMol) and 20 µL $CoCl_2$ 0.08% (0.067 µMol). The U.V. spectral curve is shown in FIG. 8A. AcPep-12 (20 µL of 1 mg/ml or 0.014 µMol) was also mixed with 5 µL $CuCl_2$ (0.08% or 0.023 µMol) and 20 µL $CoCl_2$ 0.08% (0.067 µMol). The U.V. spectral curve is shown in FIG. 8B. The $CuCl_2$ was added to Pep-12 and AcPep-12 before addition of $CoCl_2$. No shift or change occurred by this manipulation.

Pep-12 binds copper and cannot therefore display a shift and increase absorbance when cobalt is added. The tails appearing on the peaks in FIGS. 8A and 8B are due to absorbance of copper in the U.V. range.

Example 33

Enzymatic Acetylation of N-Terminal Pep-8 and Human Serum Albumin

Human serum albumin (Sigma A-1653) was incubated at 37° C. for 1 h with N-acetyl transferase and acetyl CoA, and spectral scans were obtained at various times (2-60 minutes). A steady increase at A235 was observed (assuming A235 reflects acetylation), reaching a plateau at about 40 minutes (data not shown).

Likewise, Pep-8 (Asp-Ala-His-Lys-Ser-Glu-Val-Ala, residues 1-8 of SEQ. ID. NO. 1), was acetylated according to the following conditions:

|  | 1 | 2 | 3 | 4 | 5 | 6 | 7 | 8 |
|---|---|---|---|---|---|---|---|---|
| Pep-8 | 250 µL | 250 µL | 250 µL | 250 µL |  |  |  |  |
| NAT | 50 µL |  |  | 50 µL |  | 50 µL |  | 50 µL |
| AcCoA | 25 µL | 25 µL |  |  | 25 µL |  |  | 25 µL |

-continued

| 1 | 2 | 3 | 4 | 5 | 6 | 7 | 8 |
|---|---|---|---|---|---|---|---|
| Buffer | 50 μL | 75 μL | 25 μL | 300 μL | 275 μL | 325 μL | 250 μL |
| CoCl₂ | +/− 50 μL | +/− 50 μL | +/− 50 μL | +/− 50 μL | +/− 50 μL | +/− 50 μL | +/− 50 μL | +/− 50 μL |

The Pep-8 was 1 mg/ml in a solution of Tris 50 mM, pH 7.5, 0.15 NaCl. The N-acetyl-transferase was 10 U/mL (Sigma A426). The acetyl CoA was 10 mg/ml in $H_2O$ (Sigma A2056). The Buffer was Tris 50 mM, pH 7.5, 0.15 NaCl. After completion of the reaction, test tubes were centrifuged using Centricon (3000 MW cutoff) to remove N-acetyl transferase and acetyl CoA which introduce interference in the U.V. range. The +/− in the final row refirs to the fact that the absorbance at 235 was measured with and without addition of $CoCl_2$. Addition of cobalt did not result in a shift of the peak, indicating that the acetylated Pep-8 did not bind cobalt.

Figure 9:
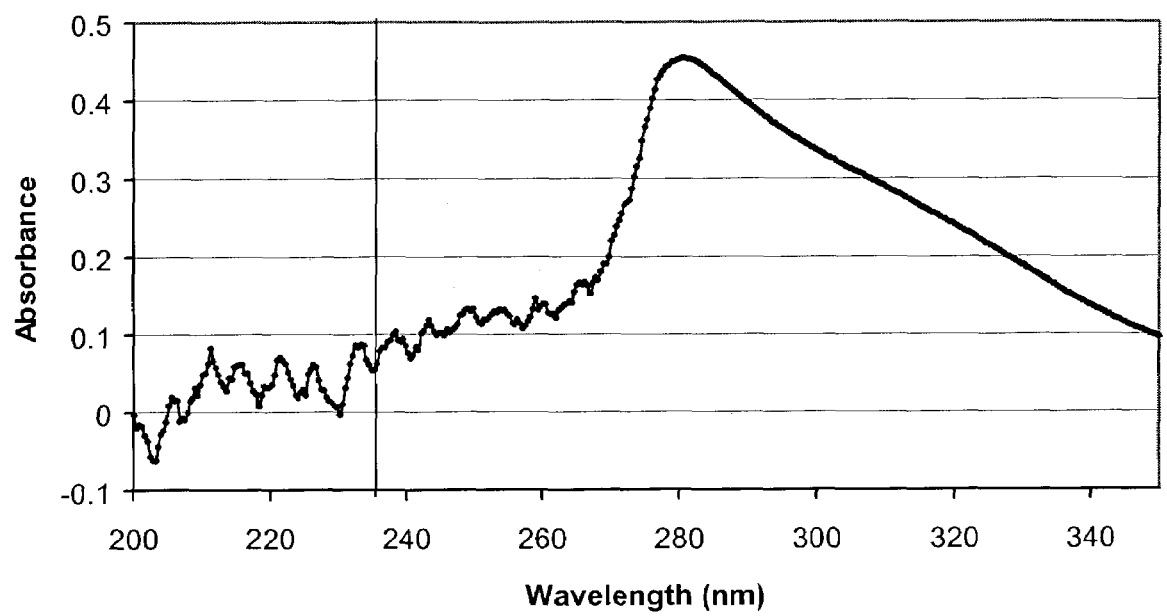
FIG. 9 is the U.V. spectra of acetylated Pep-8 (Asp-Ala-His-Lys-Ser-Glu-Val-Ala, residues 1-8 of SEQ. ID NO. 1) which did not shift upon addition of cobalt.

FIG. 9 is the subtracted scan of the centrifuged acetylated Pep-8, plus reaction mixture and cobalt, minus the reaction mixture without the cobalt, showing a peak at about 280 nm, presumably the acetylated Pep-8.

Example 34

Confirmation of Ni, Co and Co Binding to Modified Peptides by $^1$H-NMR (800 MHz)

Peptide 1: The N-terminal dodecapeptide, Asp-Ala-His-Lys-Ser-Glu-Val-Ala-His-Arg-Phe-Lys (residues 1-12 of SEQ. ID. NO. 1).

Figure 10:
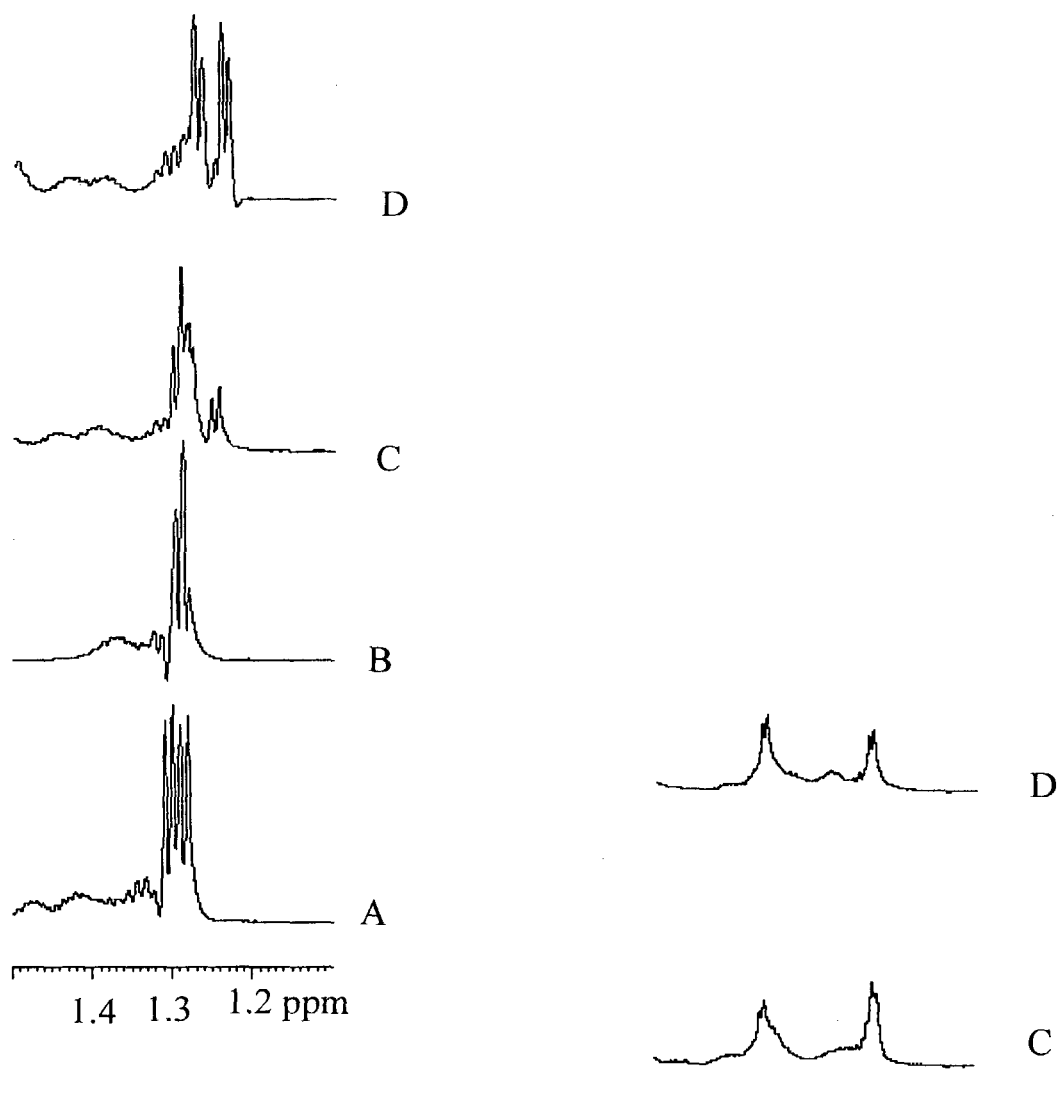
FIGS. 10A-D are the $^1$H-NMR spectra of Peptide 1 (Asp-Ala-His-Lys-Ser-Glu-Val-Ala-His-Arg-Phe-Lys, residues 1-12 SEQ. ID NO. 1) which shows the methyl signals of the two Ala residues at positions 2 and 8 as titrated by $NiCl_2$.

The N-terminal dodecapeptide was titrated with each of cobalt, copper and nickel. The methyl signals of the two Ala residues (positions 2 and 8) appear at the same resonance, namely 1.3 ppm. FIG. 10A is Peptide 1 at pH 2.55 with no metal. FIG. 10B is Peptide 1 at pH 7.33 with no metal. Titration with 0.3 equivalent $NiCl_2$ at pH 7.30 is characterized by the appearance of a set of peaks at 1.25 ppm which is characteristic of the methyl of Ala at position 2 (FIG. 10C). After the addition of one equivalent of $NiCl_2$ at pH 7.33, the methyl groups of Ala at positions 2 (1.3 ppm) and 8 (1.25 ppm) are equivalent, showing that the metal binds and that the binding is stoichiometric (FIG. 10D). FIG. 10 scans were conducted at 800 MHz, 10% $D_2O$/90%$H_2O$ (Ala-Me region).

Figure 11:
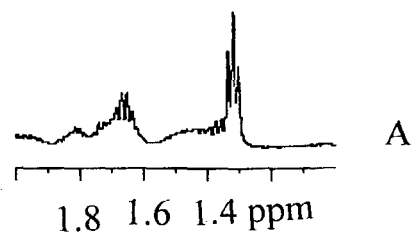
FIGS. 11A-D are the $^1$H-NMR spectra of Peptide 1 (Asp-Ala-His-Lys-Ser-Glu-Val-Ala-His-Arg-Phe-Lys, residues 1-12 of SEQ. ID NO. 1) which shows the methyl signals of the two Ala residues at positions 2 and 8 as titrated by $CoCl_2$.

The addition of $CoCl_2$ also shows binding but the peaks are broader with a shift in the methyl group Ala 2 to 1.7 ppm (FIG. 11). FIG. 11A shows Peptide 1's Ala2 and Ala8 methyl signals at 1.3 (pH 2.56). FIG. 1B shows Peptide 1 at pH 7.45. FIG. 11C shows widening of the 1.3 ppm peak as 0.5 equivalent $CoCl_2$ is added at pH 7.11. FIG. 11D shows a separate peak for Ala2-Me at 1.7 ppm with 1.0 equivalent $CoCl_2$ at pH 7.68. FIG. 11 scans were conducted at 500 MHz, 10% $D_2O$/90% $H_2O$ (Ala-Me region).

Figure 12:
FIGS. 12A-D are the $^1$H-NMR spectra of Peptide 1 (Asp-Ala-His-Lys-Ser-Glu-Val-Ala-His-Arg-Phe-Lys, residues 1-12 of SEQ. ID NO. 1) which shows the methyl signals of the two Ala residues at positions 2 and 8 as titrated by CuSO$_4$.
Figure 12:
Figure 12:
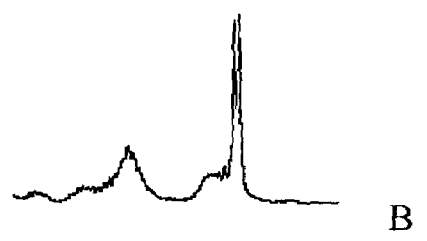
Figure 12:
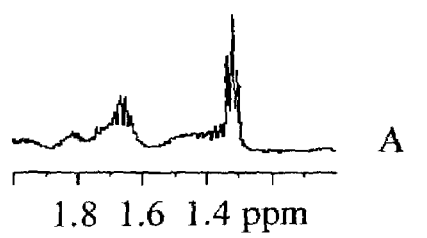

The addition of $CuSO_4$ causes even more broadening of both methyl groups at positions 2 and 8 to the point where, after addition of 1 equivalent of $CuSO_4$, both signals are lost (FIG. 12). FIG. 12A shows Peptide 1 at pH 2.56 with Ala2 and Ala8 methyl signals at 1.35 ppm. FIG. 12B shows Peptide 1 at pH 7.54. FIG. 12C shows Peptide 1 with a broadening of the signal at 1.35 ppm, due to about 0.5 equivalent $CuSO_4$ (pH 7.24). FIG. 12D shows Peptide 1 with about 1 equivalent $CuSO_4$ at pH 7.27. FIG. 12 scans were conducted at 500 MHz, 10% $D_2O$/90% $H_2O$ (Ala-Me region).

Peptide 2: The N-Terminal Dodecapeptide, Asp-Ala-His-Lys-Ser-Glu-Val-Ala-His-Arg-Phe-Lys (residues 1-12 of SEQ. ID. NO. 1), in which the Amino Group of the N-Terminal Asp has been Acetylated.

Figure 13:
FIGS. 13A-D are the $^1$H-NMR spectra of Peptide 2, which is the acetylated-Asp version of Peptide 1.
Figure 13:
Figure 13:
Figure 13:
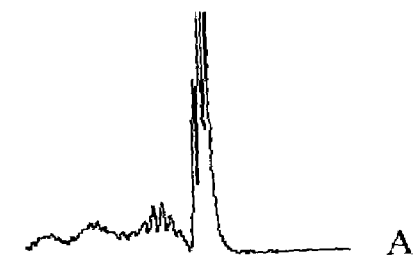

Addition of $NiCl_2$ to the acetylated derivative does not result in binding, i.e., there is no appearance of additional peaks (FIG. 13). However, addition of even one equivalent of $NiCl_2$ broadens the spectrum considerably due to the fact that the nickel is free in solution. FIG. 13A shows Peptide 2 at pH 2.63 with the Ala2 and Ala8 Me signals at about 1.28 ppm. FIG. 13B shows Peptide 2 at pH 7.36. FIG. 13C shows Peptide 2 with about 0.5 equivalent $NiCl_2$ at pH 7.09. FIG. 13D shows Peptide 2 with about 1 equivalent $NiCl_2$ at pH 7.20. FIG. 13 scans were conducted at 800 MHz, 10% $D_2O$/90% $H_2O$ (Ala-Me region).

Peptide 3: The N-Terminal Unodecapeptide, Ala-His-Lys-Ser-Glu-Val-Ala-His-Arg-Phe-Lys (residues 1-11 of SEQ. ID. NO. 1), in which the terminal Asp is missing.

Figure 14:
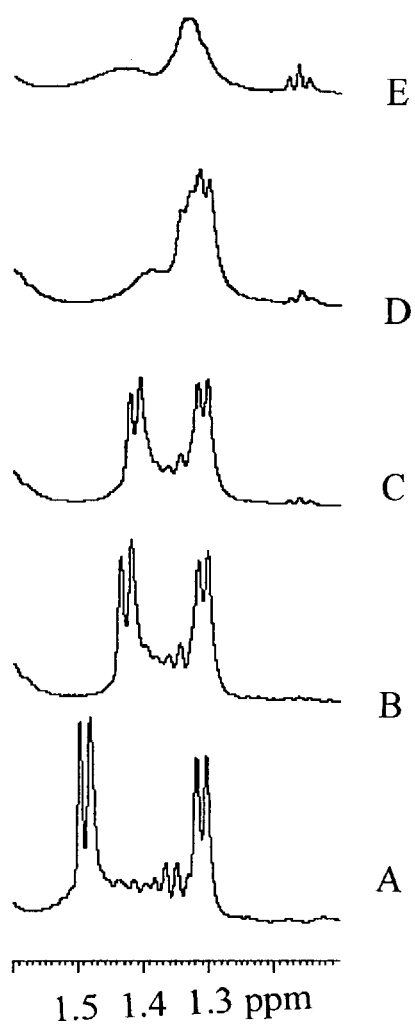
FIGS. 14A-E are the $^1$H-NMR spectra of Peptide 3 (Ala-His-Lys-Ser-Glu-Val-Ala-His-Arg-Phe-Lys, residues 1-12 of SEQ. ID NO. 1).

The N-terminal residue is Ala and consequently the position of the doublet from the methyl group is pH dependent (FIG. 14). Addition of $NiCl_2$ does not result in complex formation. FIG. 14A shows Peptide 3 at pH 2.83 with the Ala2 signal at 1.5 and the Ala8 signal at 1.3. FIG. 14B shows Peptide 3 at pH 7.15. FIG. 14C shows Peptide 3 with 0.13 equivalent $NiCl_2$ at pH 7.28. FIG. 14D shows Peptide 3 with about 0.25 equivalent $NiCl_2$ at pH 7.80. FIG. 14E shows Peptide 3 with 0.5 equivalent $NiCl_2$ at pH 8.30. FIG. 14 scans were conducted at 500 MHz, 10% $D_2O$/90% $H_2O$ (Ala-Me region).

Peptide 4: The N-terminal decapeptide, His-Lys-Ser-Glu-Val-Ala-His-Arg-Phe-Lys (residues 1-10 of SEQ. ID. NO. 1), in which Asp-Ala has been removed.

Figure 15:
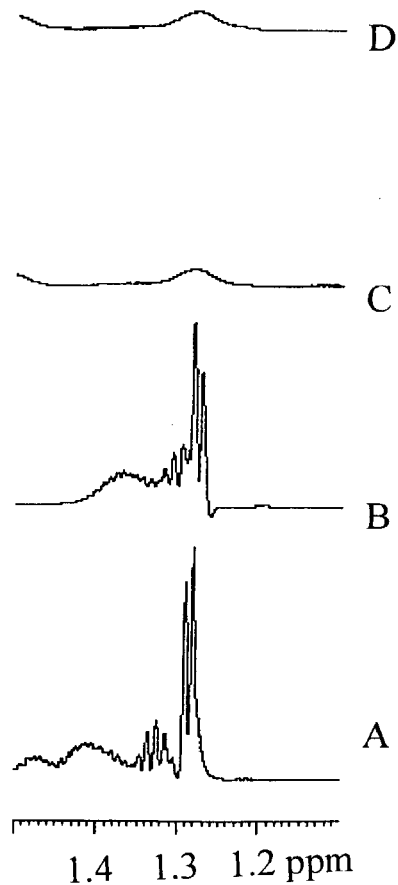
FIGS. 15A-D are the $^1$H-NMR spectra of Peptide 4 (His-Lys-Ser-Glu-Val-Ala-His-Arg-Phe-Lys, residues 3-12 SEQ. ID NO. 1).

Upon addition of $NiCl_2$ the spectrum broadens unrecognizably with no evidence of binding (FIG. 15). FIG. 15A shows Peptide 4 with an Ala8 signal at 1.8 ppm at pH 2.72. FIG. 15B shows Peptide 4 at pH 7.30. FIG. 15C shows Peptide 4 with 0.5 equivalent $NiCl_2$, pH 8.30. FIG. 15D shows Peptide 4 with about 1 equivalent $NiCl_2$ at pH 8.10. FIG. 15 scans were conducted at 800 MHz, 10% $D_2O$/90% $H_2O$ (Ala-Me region).

Peptide 5: The nonpeptide, Lys-Ser-Glu-Val-Ala-His-Arg-Phe-Lys (residues 1-9 of SEQ. ID. NO. 1), in which the tripeptide Asp-Ala-His is missing.

Figure 16:
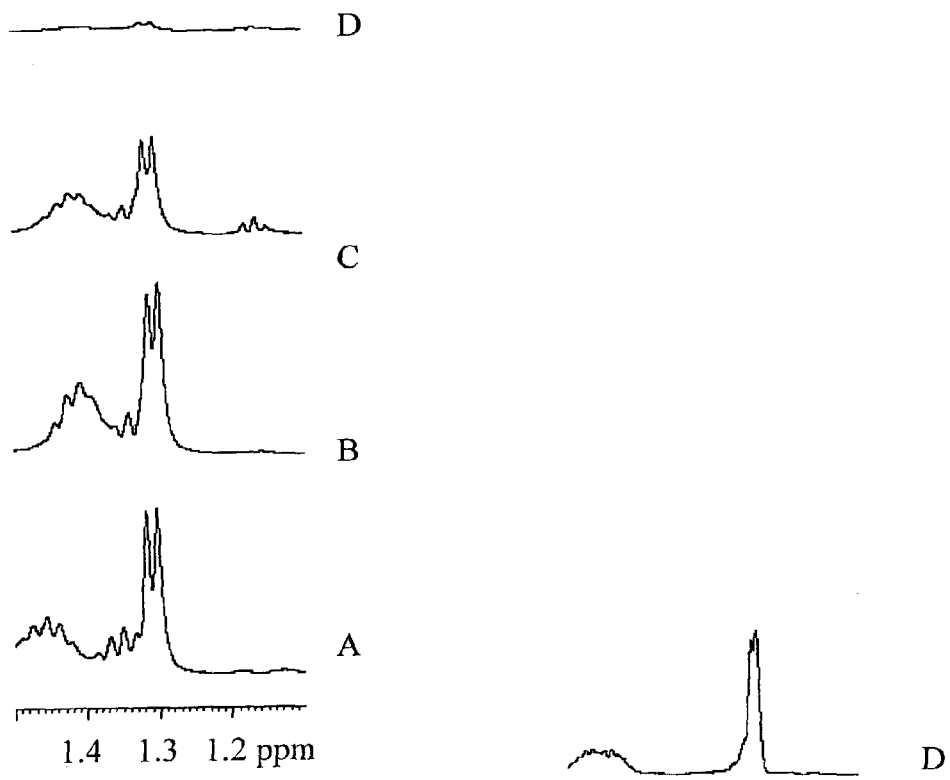
FIGS. 16A-D are the $^1$H-NMR spectra of Peptide 5 (Lys-Ser-Glu-Val-Ala-His-Arg-Phe-Lys, residues 4-12 of SEQ. ID NO. 1).

Again there is not much change in the spectrum after addition of 0.3 equivalents of $NiCl_2$ (FIG. 16C) except for the decrease in peak intensity and peak broadening upon addition of less than 1 equivalent of metal ions (FIG. 16D). There is no evidence of metal binding. FIG. 16A is Peptide 5 at pH 2.90 with the Ala8 signal at 1.3 ppm. FIG. 16B is Peptide 5 at pH 7.19. FIG. 16C is Peptide 5 with 0.3 equivalent $NiCl_2$, pH 7.02. FIG. 16D is Peptide 5 with about 0.6 equivalent $NiCl_2$ at pH 7.02. FIG. 16 scans were conducted at 500 MHz, 10% $D_2O$/90% $H_2O$ (Ala-Me region).

Peptide 6: The N-terminal tetrapeptide, Asp-Ala-His-Lys, residues 1-4 of SEQ. ID. NO. 1).

The addition of $NiCl_2$ (FIG. 17), $CoCl_2$ (FIG. 18) and $CuSO_4$ (FIG. 19) all gave diagnostic changes consistent with metal ion binding. The spectra resemble those obtained with the dodecapeptide (Peptide 1) and not those obtained with Peptides 2, 3, 4 and 5.

FIG. 17A is the N-terminal tetrapeptide at pH 2.49 with an Ala2 signal at 1.3 ppm. FIG. 17B is the tetrapeptide at pH 7.44. FIG. 17C is the tetrapeptide with about 0.8 equivalent $NiCl_2$ at pH 7.42. FIG. 17D is the tetrapeptide with about 1 equivalent $NiCl_2$ at pH 7.80.

FIG. 18A is the tetrapeptide at pH 7.44 with the Ala2 peak at 1.3 ppm. FIG. 18B is the tetrapeptide with about 0.3 equivalent $CoCl_2$ at pH 7.23. FIG. 18C is the tetrapeptide with about 0.8 equivalent $CoCl_2$ at pH 7.33.

FIG. 19A is the tetrapeptide at pH 7.31 with the Ala2 signal at 1.3 ppm. FIG. 19B is the tetrapeptide with about 0.5 equivalent $CuSO_4$ at pH 7.26. FIG. 19C is the tetrapeptide with about 1.0 equivalent $CuSO_4$ at pH 7.32.

Figure 17:
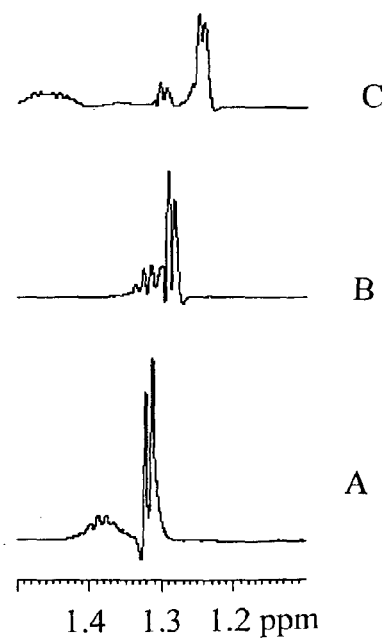
FIGS. 17A-D are $^1$H-NMR spectra of the N-terminal tetrapeptide, Asp-Ala-His-Lys, residues 1-4 of SEQ. ID NO. 1.
Figure 18:
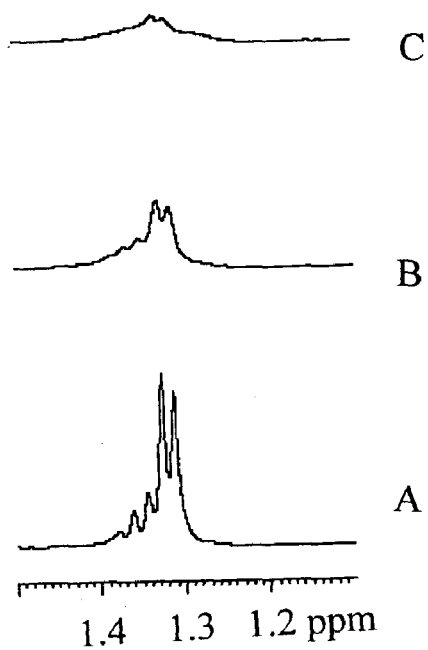
FIGS. 18A-C are $^1$H-NMR spectra of the N-terminal tetrapeptide with CoCl$_2$.
Figure 19:
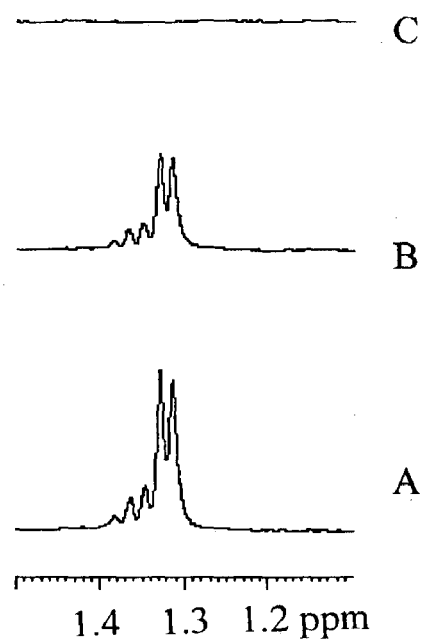
FIGS. 19A-C are $^1$H-NMR spectra of the N-terminal tetrapeptide with CuSO$_4$.

FIGS. 17-19 scans were conducted at 800 MHz, 10% $H_2O$/90% $D_2O$ (Ala-Me region).

The above description of the invention is intended to be illustrative and not limiting. Various changes or modification in the embodiments described may occur to those skilled in the art. These can be made without departing from the spirit or scope of the invention.

---

What is claimed is:

1. A method of detecting the occurrence or non-occurrence of an ischemic event in a patient comprising the steps of:
   (a) contacting a biological sample containing albumin from said patient with a predetermined excess quantity of a salt of a metal selected from the group consisting of V, As, Co, Cu, Sb, Cr, Mo, Mn, Ba, Zn, Ni, Hg, Cd, Fe, Pb, Au and Ag, to form a sample mixture containing metal ions bound to the albumin and unbound metal ions,
   (b) contacting said sample mixture with an aqueous color forming compound solution to form a colored sample mixture, wherein said compound forms color when bound to said unbound metal ion,
   (c) measuring color intensity of said colored sample mixture on an analyzer,
   (d) (i) providing one or more calibrators selected from the group consisting of: albumin N-terminal peptides and metal ions; full-length albumin, albumin N-terminal peptides and metal ions; chelating agents; and albumin N-terminal peptides;
      (ii) adding metal ions to said one or more calibrators thereby permitting formation of sequestered and in some cases, unbound metal ions,
      (iii) adding the coloring compound that binds to unbound metal ions, if any, and
      (iv) measuring color intensity of the product of step (d)(iii) on the analyzer and generating a standard curve, and
   (e) comparing the measured color intensity of the colored sample mixture to a known value on the standard curve to determine the occurrence or non-occurrence of an ischemic event.

2. The method of claim 1, wherein the calibrators comprise mixtures of albumin N-terminal peptides and metal ion in predetermined molar ratios.

3. The method of claim 2, wherein the predetermined molar ratios of albumin N-terminal peptides and metal ion in the calibrators extend over a range of albumin metal ion binding sites that includes normal and ischemic populations.

4. The method of claim 1, wherein the calibrators comprise mixtures of full-length albumin in predetermined concentrations.

5. The method of claim 1, wherein the calibrators comprise mixtures of albumin N-terminal peptides in predetermined concentrations.

6. The method of claim 1, wherein the calibrators comprise mixtures of chelators in predetermined molar concentrations.

7. The method of claim 6, wherein the chelator is EDTA.

8. The method of claim 1, wherein said aqueous color forming compound comprises the compound Asp-Ala-His-Lys-R, wherein R is any group capable of forming color when the compound is bound to the metal ion, and Asp-Ala-His-Lys is amino acids 1-4 of SEQ. ID. NO. 1.

9. The method of claim 1, wherein the sample is serum or plasma.

10. The method of claim 1, wherein the sample is purified albumin.

11. The method of claim 1, wherein the metal ion is cobalt.

12. A method of detecting stress-induced ischemia in a patient, comprising:
   conducting the method of claim 1 before, during and/or after a patient is subjected to an exercise stress test or a pharmacological stress test.

13. The method of claim 12, wherein said patient possesses one or more cardiac risk factors.

14. The method of claim 12, wherein the exercise test is a treadmill test.

15. The method of claim 12, wherein the pharmacological stress is dobutamine.

16. The method of claim 12, further comprising repetition of said method of claim 12 at additional designated times, and comparison of results obtained at each designated time.

17. The method of claim 16, wherein the designated times are three months, six months and one year.

18. A method of monitoring a patient's response to angioplasty, comprising:
(a) conducting the method of claim 1 prior to angioplasty;
(b) conducting the angioplasty; and
(c) repeating the method of claim 1 after the angioplasty, whereby the patient's response to the angioplasty is monitored.

19. The method of claim 6, wherein the chelator is citrate.

20. The method of claim 6, wherein the chelator is oxalate.

21. A method of detecting the occurrence or non-occurrence of an ischemic event in a patient comprising the steps of:
(a) contacting a biological sample containing albumin from said patient with a predetermined excess quantity of a salt of a metal selected from the group consisting of V, As, Co, Cu, Sb, Cr, Mo, Mn, Ba, Zn, Ni, Hg, Cd, Fe, Pb, Au and Ag, to form a sample mixture containing metal ions bound to the albumin and unbound metal ions,
(b) contacting said sample mixture with an aqueous color forming compound solution to form a colored sample mixture, wherein said compound forms color when bound to said unbound metal ion,
(c) measuring color intensity of said colored sample mixture on an analyzer,
(d) (i) providing one or more calibrators selected from the group consisting of full-length albumin and metal ions; and full-length albumin and albumin N-terminal derivatives,
   (ii) adding metal ions to said one or more calibrators thereby permitting formation of bound and, in some cases, unbound metal ions,
   (iii) adding the coloring compound that binds to unbound metal ions, if any, and
   (iv) measuring color intensity of the product of step (d)(iii) on the analyzer and generating a standard curve, and
(e) comparing the measured color intensity of the colored sample mixture to a known value on the standard curve to determine the occurrence or non-occurrence of an ischemic event.

22. The method of claim 21, wherein the calibrators comprise mixtures of full length albumin and metal ion in predetermined molar ratios.

23. The method of claim 22, wherein the predetermined molar ratios of albumin and metal ion in the calibrators extend over a range of albumin metal ion binding sites that includes normal and ischemic populations.

24. The method of claim 21, wherein the calibrators are mixtures of full-length albumin and albumin N-terminal derivatives in predetermined ratios that cover a range of albumin metal ion binding sites that include normal and ischemic populations.

25. The method of claim 21, wherein said aqueous color forming compound comprises the compound Asp-Ala-His-Lys-R, wherein R is any group capable of forming color when the compound is bound to the metal ion, and Asp-Ala-His-Lys is amino acids 1-4 of SEQ. ID. NO. 1.

26. The method of claim 21, wherein the sample is selected from the group consisting of serum, plasma and purified albumin.

27. The method of claim 21, wherein the metal ion is cobalt.

28. A method of detecting stress-induced ischemia in a patient, comprising:
conducting the method of claim 21 before, during and/or after a patient is subject to an exercise stress test or a pharmacological stress test.

* * * * *